United States Patent
Henry et al.

(10) Patent No.: US 11,739,154 B2
(45) Date of Patent: Aug. 29, 2023

(54) AXL-SPECIFIC ANTIBODIES AND USES THEREOF

(71) Applicant: National Research Council of Canada, Ottawa (CA)

(72) Inventors: Kevin Henry, Ottawa (CA); Maria Luz Jaramillo, Montreal (CA); Colin Roger Mackenzie, Ottawa (CA); Anne Marcil, Pierrefonds (CA)

(73) Assignee: NATIONAL RESEARCH COUNCIL OF CANADA, Ottawa (CA)

( * ) Notice: Subject to any disclaimer, the term of this patent is extended or adjusted under 35 U.S.C. 154(b) by 359 days.

(21) Appl. No.: 16/646,823

(22) PCT Filed: Sep. 10, 2018

(86) PCT No.: PCT/CA2018/051108
§ 371 (c)(1),
(2) Date: Mar. 12, 2020

(87) PCT Pub. No.: WO2019/051586
PCT Pub. Date: Mar. 21, 2019

(65) Prior Publication Data
US 2020/0277386 A1 Sep. 3, 2020

Related U.S. Application Data

(60) Provisional application No. 62/557,870, filed on Sep. 13, 2017.

(51) Int. Cl.
| | | |
|---|---|---|
| C07K 16/28 | (2006.01) | |
| A61K 47/68 | (2017.01) | |
| A61P 35/00 | (2006.01) | |
| A61K 49/00 | (2006.01) | |
| C12N 5/16 | (2006.01) | |
| A61K 39/00 | (2006.01) | |

(52) U.S. Cl.
CPC ...... C07K 16/2863 (2013.01); A61K 47/6803 (2017.08); A61K 49/00 (2013.01); A61P 35/00 (2018.01); C12N 5/16 (2013.01); *A61K 2039/505* (2013.01); *C07K 2317/24* (2013.01); *C07K 2317/33* (2013.01); *C07K 2317/565* (2013.01); *C07K 2317/567* (2013.01); *C07K 2317/77* (2013.01); *C07K 2317/92* (2013.01); *C07K 2319/00* (2013.01)

(58) Field of Classification Search
CPC ............ C07K 16/2863; C07K 2317/24; C07K 2317/33; C07K 2317/565; C07K 2317/567; C07K 2317/77; C07K 2317/92; C07K 2319/00; A61K 47/6803; A61K 2039/505; A61P 35/00
See application file for complete search history.

(56) References Cited

U.S. PATENT DOCUMENTS

2014/0227283 A1   8/2014 Robert et al.

FOREIGN PATENT DOCUMENTS

| WO | WO-2012175691 A1 * | 12/2012 | .............. A61P 31/00 |
|---|---|---|---|
| WO | 2016005593 A1 | 1/2016 | |
| WO | 2016187354 A1 | 11/2016 | |
| WO | 2017009258 A1 | 1/2017 | |

OTHER PUBLICATIONS

Asiedu et al., "AXL Induces Epithelial-to-mesenchymal Transition and Regulates the Function of Breast Cancer Stem Cells," Oncogene, 2014, vol. 33(10), pp. 1316-1324.
Baral et al., "Single-domain Antibodies and Their Utility," Current Protocols in Immunology, Nov. 2013, vol. 2.17, pp. 1-2.17.57.
Feneyrolles et al., "Axl Kinase as a Key Target for Oncology: Focus on Small Molecule Inhibitors," Molecular Cancer Therapeutics, Sep. 2014, vol. 13(9), pp. 2141-2148.
Gjerdrum et al., "Axl is an Essential Epithelial-to-Mesenchymal Transition-induced Regulator of Breast Cancer Metastasis and Patient Survival," Proceedings of the National Academy of Sciences of the United States of America, Jan. 2010 , vol. 107(3), pp. 1124-1129.
Gonzales et al., "Minimizing the Immunogenicity of Antibodies for Clinical Application," Tumor Biology, 2005, vol. 26(1), pp. 31-43.
Henry et al., "Isolation of TGF-β-neutralizing Single-domain Antibodies of Predetermined Epitope Specificity Using Next-generation DNA Sequencing," Protein Engineering Design & Selection, Sep. 2016, vol. 29(10), pp. 439-443.
Holland et al., "Multiple Roles for the Receptor Tyrosine Kinase Axl in Tumor Formation," Cancer Research, Oct. 2005, vol. 65(20), pp. 9294-9303.
Holland et al., "R428, A Selective Small Molecule Inhibitor of Axl Kinase, Blocks Tumor Spread and Prolongs Survival in Models of Metastatic Breast Cancer," Cancer Research, Feb. 2015, vol. 70(4), pp. 1544-1554.
International Patent Application No. PCT/CA2018/051108, International Preliminary Report on Patentability dated Mar. 17, 2020.
International Patent Application No. PCT/CA2018/051108, International Search Report and Written Opinion dated Dec. 3, 2018.
Jones et al., "Replacing the Complementarity-determining Regions in a Human Antibody With Those From a Mouse," Nature, May 1986, vol. 321(6069), pp. 522-525.
Kitagawa et al., "Activity-based Kinase Profiling of Approved Tyrosine Kinase Inhibitors," Genes Cells, 2013, vol. 18(2), pp. 110-122.
Leconet et al., "Preclinical Validation of AXL Receptor as a Target for Antibody-based Pancreatic Cancer Immunotherapy," Oncogene, 2014, vol. 33, pp. 5405-5414.

(Continued)

*Primary Examiner* — Ruixiang Li
(74) *Attorney, Agent, or Firm* — Kathleen Marsman; Borden Ladner Gervais LLP

(57) ABSTRACT

AXL-specific antibodies and uses therefor are described, including monoclonal and single domain antibodies. Such antibodies bind to cell surface expressed human AXL at an epitope in an immunoglobulin-like (IgL) domain of the AXL ectodomain. The antibody may be used in an antibody-drug conjugate (ADC), for example in the treatment, detection or staging of cancer. The antibody may be biparatopic.

23 Claims, 19 Drawing Sheets

Specification includes a Sequence Listing.

(56) References Cited

OTHER PUBLICATIONS

Lee et al., "GAS6/Axl Pathway Promotes Tumor Invasion Through the Transcriptional Activation of Slug in Hepatocellular Carcinoma," Carcinogenesis, 2013, vol. 35, pp. 769-775.

Li et al., "A Biparatopic Her2-targeting Antibody-drug Conjugate Induces Tumor Regression in Primary Models Refractory to or Ineligible for Her2-targeted Therapy," Cancer Cell, 2016, vol. 29(1), pp. 117-129.

Li et al., "Axl as a Potential Therapeutic Target in Cancer: Role of Axl in Tumor Growth, Metastasis and Angiogenesis," Oncogene, 2009, vol. 28, pp. 3442-3455.

Linger et al., "Tam Receptor Tyrosine Kinases: Biologic Functions, Signaling, and Potential Therapeutic Targeting in Human Cancer," Advances in Cancer Research, 2008, vol. 100, pp. 35-83.

Meyer et al., "The Receptor AXL Diversifies EGFR Signaling and Limits the Response to EGFR-targeted Inhibitors in Triple-negative Breast Cancer Cells," Science Signaling, 2013, vol. 6(287), pp. ra66.

O'Bryan et al., "Axl, A Transforming Gene Isolated From Primary Human Myeloid Leukemia Cells, Encodes a Novel Receptor Tyrosine Kinase," Molecular and Cellular Biology, Oct. 1991, vol. 11(10), pp. 5016-5031.

Paccez et al., "The Receptor Tyrosine Kinase Axl in Cancer: Biological Functions and Therapeutic Implications," International Journal of Cancer, 2014, vol. 134(5), pp. 1024-1033.

Padlan et al., "A Possible Procedure for Reducing the Immunogenicity of Antibody Variable Domains While Preserving Their Ligand-binding Properties," Molecular Immunology, 1991, vol. 28(4-5), pp. 489-498.

Queen et al., "A Humanized Antibody That Binds to the Interleukin 2 Receptor," Proceedings of the National Academy of Sciences of the United States of America, Dec. 1989, vol. 86, pp. 10029-10033.

Rankin et al., "Direct Regulation of Gas6/AXLSignaling by HIF Promotes Renal Metastasis Through SRCand MET," Proceedings of the National Academy of Sciences of the United States of America, Sep. 2014, vol. 111(37), pp. 13373-13378.

Raymond et al., "Production of α2,6-Sialylated IgG1 in CHO cells," Mabs, May/Jun. 2015, vol. 7(3), pp. 571-583.

Riechmann et al., "Reshaping Human Antibodies for Therapy," Nature, Mar. 1988, vol. 332, pp. 323-327.

Strop et al., "Generating Bispecific Human Igg1 and Igg2 Antibodies From Any Antibody Pair," Journal of Molecular Biology, 2012, vol. 420(3), pp. 204-219.

Tempest et al., "Reshaping a Human Monoclonal Antibody to Inhibit Human Respiratory Syncytial Virus Infection in Vivo," Biotechnology, Mar. 1991, vol. 9(3), pp. 266-271.

Thomson et al., "A Systems View of Epithelial-mesenchymal Transition Signaling States," Clinical & Experimental Metastasis, 2011, vol. 28(2), pp. 137-155.

Tsurushita et al., "Design of Humanized Antibodies: From Anti-tac to Zenapax," Methods, 2005, vol. 36(1), pp. 69-83.

Vincke et al., "General Strategy to Humanize a Camelid Single-domain Antibody and Identification of a Universal Humanized Nanobody Scaffold," Journal of Biological Chemistry, Jan. 2009, vol. 284(5), pp. 3273-3284.

Yakes et al., "Cabozantinib (XL184), a Novel MET and VEGFR2 Inhibitor, Simultaneously Suppresses Metastasis, Angiogenesis, and Tumor Growth," Molecular Cancer Therapeutics, Dec. 2011, vol. 10(12), pp. 2298-2308.

Zhang et al., "Transient Expression and Purification of Chimeric Heavy Chain Antibodies," Protein Expression and Purification, 2009, vol. 65(1), pp. 77-82.

Zhou et al., "Internalizing Cancer Antibodies From Phage Libraries Selected on Tumor Cells and Yeast-displayed Tumor Antigens," Journal of Molecular Biology, 2010, vol. 404, pp. 88-99.

European Patent Application No. 118855793.8, Extended European Search Report dated May 7, 2021.

Okimoto, et al., "AXL Receptor Tyrosine Kinase as a Therapeutic Target in NSCLC, "Lung Cancer (Auckland, N.Z.), 2015, vol. 6, pp. 27-34.

* cited by examiner

AXL protein ectodomain

| AXL fragment # | AXL amino acids | AXL domain | F107-8D12-2 | F107-7H5-2 | F107-10G1-3 | F111-3C8-2 | F111-5E9-2 | F138-9H4-2 | F138-9G4-2 |
|---|---|---|---|---|---|---|---|---|---|
| 1 | 135-226 | IgL2 | - | - | - | ++ | + | - | + |
| 2 | 321-429 | FN III-2 | - | - | - | - | - | - | - |
| 3 | 26-138 | IgL1 | +++ | +++ | +++ | - | - | ++ | - |
| 4 | 219-335 | FN III-1 | - | - | - | - | - | - | - |
| 5 | 321-450 | FN III-2+ | - | - | - | - | - | - | - |
| 6 | 26-226 | IgL1+IgL2 | ++++ | ++++ | +++ | ++ | + | +++ | + |
| 7 | 135-335 | IgL2+FN III-1 | - | - | - | +++ | ++ | - | + |
| 8 | 219-450 | FN III-1+FN III-2+ | - | - | - | - | - | - | - |
| 9 | 26-429 | IgL1+IgL2+FN III-1+FN III-2 | ++++ | +++ | ++ | +++ | ++ | ++ | + |
| 10 | 26-450 | IgL1+IgL2+FN III-1+FN III-2+ | ++++ | ++++ | +++ | ++++ | ++ | +++ | + |
| None | ----- | ----- | - | - | - | - | - | - | - |

>F107.10G1(heavy)>EVNLVESGGGVVKPGASLKLSCEASGFTFSNYGMSWVRQTSDKRLEWVASISGGGGRTYYLD
NVKGRFIISRENAKNTLYLQMSSLKSEDTALFYCARGARASYFAMDYWGQGSSVTVSS (SEQ ID:47, 77-79, 35-37)

>F107.10G1(kappa)>VIVMTQSHKFMSTSVGDRVSITCKASQDVTTAVAWYQQKPGQSPKLLIYWASTRHTGVPDR
FTGSGSGTDYSLTISNVQTEDLAFYYCQQHFTTPLTFGAGTKLELK (SEQ ID NO:46, NO:80-82 and NO:32-34)

>F111.5E9(heavy)>QIQLVQSGPELKKPGETVKISCKASGYTFTKYGMNWVKQAPGKGLKWMGWINTYTGEPTYAD
DFKGRFAFSLETSASTAYLQINNLTTEDMVTYFCAKGGYYSNPIYPMDYWGQGTSVTVSS (SEQ:45, 83-85, 23-25)

>F111.5E9(kappa)>DIQMTQTTSSLSASLGDRVTISCRASQDINNYLNWYQQKPDGTVKLLIYYISRLHSGVPSRFSGS
GSGTDYSLTISNLELEDVATYFCQQGNTLPFTFGSGTKLEIK (SEQ ID NO:44, NO: 86-88 and NO:20-22)

>F107.8D12(heavy)>QVQLQQPGAELVKPGASVQLSCKASGYTFISFWINWVKQRPGQGLEWMGNIFPGSSSTNYN
EKFKSKATLTVDKSSSTAYMQLSSLTSEDSAVYFCARDYYGGSPDYWGQGTTLTVSS (SEQ ID NO:41, 89-91, 17-19)

>F107.8D12(kappa)>DIVMSQSPSSLAVSAGERVTMSCKSSQSLLNTRTRKNYLAWYQQKPGQSPKLLIYWASTRES
GVPDRFTGSGSGTDFTLTISSVQAEDLAVYYCKQSYNLWTFGGGTKLEIK (SEQ ID NO:40, NO: 92-94, 15,16,11)

>F107.7H5(heavy)>QVQLQQPGAELVKPGASVKLSCKASGYTFTSYWINWVKQRPGQGLEWIGNIYPDSSSTNYNEK
FKSKATLTVDKSSTTAYIQFSSLTSEDSAVYYCTRDTYGGSPDYWGQGTTLTVSS (SEQ ID NO:39, 95-97, 12-14)

>F107.7H5(kappa)DIVMSQSPSSLAVSAGEKVTMSCKSSQSLLNSRTRKIYLAWYQQKPGQSPKLLIYWASTRQSGVP
DRFTGSGSGTDFTLTISSVQAEDLAVYYCKQSYNLWTFGGGTKLEIK (SEQ ID NO:38, NO: 98-100, 9-11)

>F155.3C7(heavy)>QVQLQQPGTELVKPGASVKLSCKASGYIFTNFWINWVKQRPGQGLEWIGNIFPGSNSSNYNEK
FKNKATLTVDKSSSTAYMHLSSLTSEDSAVYYCVRDYYGGSPDYWGQGTTLTVSS (SEQ NO:73, 101-103, 151-153)

>F155.3C7(kappa)>DIVMSQSPSSLAVSAGEKVTMSCKSSQSLLNSKTRKNYLAWYQQKPGQSPKLLIYWASTRESGV
PARFTGSGSGTDFTLTISSVQAEDLAIYYCKHSYNLWTFGGGTKLEIR (SEQ:74, 104-106, 154-156)

>F111.3C8(heavy)>QVQLQQPGAELGKPGTSVKLSCKASGYTFTSYWMHWVKRVPGQGLEWIGNINPNSTSADYN
EKFKRKATLTVDKSSSTAYMQLSTLTSEDSAVYYCTRPLMGPYWYFDVWGTGTTVTVSS (SEQ:43, 107-109, 29-31)

>F111.3C8(kappa)>QIVLTQSPAIMSASPGEKVTISCSASSSVSYMYWYQQKPGSSPKPWIYRTSNLASGVPARFSGSG
SGTSYSLTISSMEAEDAATYYCQQYHNYPPTFGGGTKLEIK (SEQ ID NO:42, 110-112, and 26-28)

>F149.4G4(heavy)>QIQLVQSGPELKKPGETVKISCKTSGYTFTYYGINWVKQAPGKGLEWMGWINTYLGEPTYADD
FKGRFAFSLETSASTAYLQINNLRDEDMATYFCTRGTMSYSFDYWGQGTALTVSS (SEQ:75, 113-115, 157-159)

>F149.4G4(kappa)>QNVLTQSPAIMSASPGEEVTMTCRASSSVSSSYLHWYQQKSGASPKLWIYSTSKLASGVPARFS
GSGSGTSYSLTISSVEAEDAATYYCHQYSGDPLTFGSGTKLEVK (SEQ ID NO:76, NO: 116-118, 160-162)

FIG. 7

>NRC-sdAb001
QVKLEESGGGLVQAGGSLRLSCTASASISSFDIMGWYRQAPGKQRELVAAITTLDIANYRDSVKGRFTISRDNAKNTVY
LQMDSLKPEDTARYHCAAFQSDQNYWGQGTQVTVSS (SEQ ID NO: 119, NO: 127-129, 163-165)

>NRC-sdAb002
QVQLVDSGGGLVQAGGSLRLSCATSTRTVSSAVMAWFRQAPEKVRDFVGFITNSGNILYDDSVKGRFTISRDNAQNT
VYLQMNSLKPEDTAVYYCAAKWSFSSGYGDLRRAAMYDYWGQGTQVTVSS (SEQ NO:120, 130-132, 166-168)

>NRC-sdAb003
QVQLVESGGGLVQAGGSLRLSCAASGVTLDYTAIGWFRQAPGKERELVAAITSGGNTDYAESAKGRFRISRDNSKNTIY
LQMNSLKPEDTGVYYCAARRGGARGEYDYWDQGTQVTVSS (SEQ ID NO:121, NO: 133-135, 169-171)

>NRC-sdAb004
QVQLVESGGGVVQAGGSLRLSCAFSRGAFDTYEIGWFRQAPGKEREFVAAVTRNGDSVVYADSLKARFTASRNNAVN
TAYLHMNILQPEDTATYYCAANWRPLRTSSGADDYADWGQGTQVTVSS (SEQ ID NO:122, 136-138, 172-174)

>NRC-sdAb005
QVKLEESGGGLAQAGGSLRLSCAASGSISSINTIGWFRQAPGKQRELVAASDSGANRNYADSVKGRFTISRDNAKNTV
YLQMNNLKPEDTAIYYCRAWGTGTISTMYWGQGTQVTVSS (SEQ ID NO:123, NO:139-141, and 175-177)

>NRC-sdAb006
QVKLEESGGGLVQAGASLRLSCVASESIFGFNTMGWYRQAPGNERELVASISNSKRTMYADSVKGRFTISRDNAKNTV
NLQMNNLKPEDTAVYYCRAWGIITSATVYWGQGTQVTVSS (SEQ ID NO:124, NO: 142-144, 178-180)

>NRC-sdAb007
QVKLEESGGGLVQAGGSLRLSCATSTRTVSSAVMAWFRQAPEKERDFVGFISNSGSVYYDDSVKGRFTISRDNAQNTV
YLQMNSLKPEDTAVYYCAIIWRTSDLTGRFNTWGQGTQVTVSS (SEQ ID NO:125, NO:145-147, 181-183)

>NRC-sdAb008
QVKLEESGGGLVQAGGSLRLSCAASGSSGMINTMGWYRQAPGKQRELVARRSTGGTTNYADSVKGRFTISRDDANN
TVYLQMNSLKPEDTAVYYCAIIWRTSDLTGRFNTWGQGTQVTVSS (SEQ ID NO:126, NO:148-150, 184-186)

FIG. 8

SEQUENCE LISTING

<160> NUMBER OF SEQ ID NOS: 188

<210> SEQ ID NO 1
<211> LENGTH: 17
<212> TYPE: PRT
<213> ORGANISM: Artificial Sequence

```
<220> FEATURE:
<223> OTHER INFORMATION: CDR L1-B consensus
<220> FEATURE:
<221> NAME/KEY: misc_feature
<222> LOCATION: (9)..(9)
<223> OTHER INFORMATION: Xaa = S or T
<220> FEATURE:
<221> NAME/KEY: misc_feature
<222> LOCATION: (14)..(14)
<223> OTHER INFORMATION: Xaa = I or N

<400> SEQUENCE: 1

Lys Ser Ser Gln Ser Leu Leu Asn Xaa Arg Thr Arg Lys Xaa Tyr Leu
1               5                   10                  15

Ala

<210> SEQ ID NO 2
<211> LENGTH: 7
<212> TYPE: PRT
<213> ORGANISM: Artificial Sequence
<220> FEATURE:
<223> OTHER INFORMATION: CDR L2-B consensus
<220> FEATURE:
<221> NAME/KEY: MISC_FEATURE
<222> LOCATION: (6)..(6)
<223> OTHER INFORMATION: Xaa is E, H or Q
<220> FEATURE:
<221> NAME/KEY: MISC_FEATURE
<222> LOCATION: (7)..(7)
<223> OTHER INFORMATION: Xaa is S or T

<400> SEQUENCE: 2

Trp Ala Ser Thr Arg Xaa Xaa
1               5

<210> SEQ ID NO 3
<211> LENGTH: 10
<212> TYPE: PRT
<213> ORGANISM: Artificial Sequence
<220> FEATURE:
<223> OTHER INFORMATION: CDR H1-B consensus
<220> FEATURE:
<221> NAME/KEY: MISC_FEATURE
<222> LOCATION: (2)..(2)
<223> OTHER INFORMATION: Xaa is F or Y
<220> FEATURE:
<221> NAME/KEY: MISC_FEATURE
<222> LOCATION: (5)..(5)
<223> OTHER INFORMATION: Xaa is I, S, or T
<220> FEATURE:
<221> NAME/KEY: MISC_FEATURE
<222> LOCATION: (6)..(6)
<223> OTHER INFORMATION: Xaa is S, N, or K
<220> FEATURE:
<221> NAME/KEY: MISC_FEATURE
<222> LOCATION: (7)..(7)
<223> OTHER INFORMATION: Xaa is F or Y
<220> FEATURE:
<221> NAME/KEY: MISC_FEATURE
<222> LOCATION: (8)..(8)
<223> OTHER INFORMATION: Xaa is G or W
<220> FEATURE:
<221> NAME/KEY: MISC_FEATURE
<222> LOCATION: (9)..(9)
<223> OTHER INFORMATION: Xaa is i or M
<220> FEATURE:
<221> NAME/KEY: MISC_FEATURE
<222> LOCATION: (10)..(10)
<223> OTHER INFORMATION: Xaa is N, S, or H

<400> SEQUENCE: 3

Gly Xaa Thr Phe Xaa Xaa Xaa Xaa Xaa Xaa
1               5                   10
```

```
<210> SEQ ID NO 4
<211> LENGTH: 17
<212> TYPE: PRT
<213> ORGANISM: Artificial Sequence
<220> FEATURE:
<223> OTHER INFORMATION: CDR H2-B consensus
<220> FEATURE:
<221> NAME/KEY: MISC_FEATURE
<222> LOCATION: (3)..(3)
<223> OTHER INFORMATION: Xaa is F, N, or Y
<220> FEATURE:
<221> NAME/KEY: MISC_FEATURE
<222> LOCATION: (5)..(5)
<223> OTHER INFORMATION: Xaa is G, N, or D
<220> FEATURE:
<221> NAME/KEY: MISC_FEATURE
<222> LOCATION: (7)..(7)
<223> OTHER INFORMATION: Xaa is S or T
<220> FEATURE:
<221> NAME/KEY: MISC_FEATURE
<222> LOCATION: (9)..(9)
<223> OTHER INFORMATION: Xaa is A or T
<220> FEATURE:
<221> NAME/KEY: MISC_FEATURE
<222> LOCATION: (10)..(10)
<223> OTHER INFORMATION: Xaa is N or D
<220> FEATURE:
<221> NAME/KEY: MISC_FEATURE
<222> LOCATION: (17)..(17)
<223> OTHER INFORMATION: Xaa is S or R

<400> SEQUENCE: 4

Asn Ile Xaa Pro Xaa Ser Xaa Ser Xaa Xaa Tyr Asn Glu Lys Phe Lys
1               5                   10                  15

Xaa

<210> SEQ ID NO 5
<211> LENGTH: 9
<212> TYPE: PRT
<213> ORGANISM: Artificial Sequence
<220> FEATURE:
<223> OTHER INFORMATION: CDR H3-B consensus
<220> FEATURE:
<221> NAME/KEY: misc_feature
<222> LOCATION: (2)..(2)
<223> OTHER INFORMATION: Xaa is T or Y

<400> SEQUENCE: 5

Asp Xaa Tyr Gly Gly Ser Pro Asp Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: CDR L2-B consensus (2)
<220> FEATURE:
<221> NAME/KEY: misc_feature
<222> LOCATION: (6)..(6)
<223> OTHER INFORMATION: Xaa is E or Q

<400> SEQUENCE: 6

Trp Ala Ser Thr Arg Xaa Ser
1               5

<210> SEQ ID NO 7
<211> LENGTH: 10
<212> TYPE: PRT
<213> ORGANISM: Artificial Sequence
<220> FEATURE:
<223> OTHER INFORMATION: CDR H1-B consensus (2)
```

```
<220> FEATURE:
<221> NAME/KEY: MISC_FEATURE
<222> LOCATION: (7)..(7)
<223> OTHER INFORMATION: Xaa is F or Y

<400> SEQUENCE: 7

Gly Tyr Thr Phe Thr Ser Xaa Trp Ile Asn
1               5                   10

<210> SEQ ID NO 8
<211> LENGTH: 17
<212> TYPE: PRT
<213> ORGANISM: Artificial Sequence
<220> FEATURE:
<223> OTHER INFORMATION: CDR H2-B consensus (2)
<220> FEATURE:
<221> NAME/KEY: MISC_FEATURE
<222> LOCATION: (3)..(3)
<223> OTHER INFORMATION: Xaa is F or Y
<220> FEATURE:
<221> NAME/KEY: MISC_FEATURE
<222> LOCATION: (5)..(5)
<223> OTHER INFORMATION: Xaa is G or D

<400> SEQUENCE: 8

Asn Ile Xaa Pro Xaa Ser Ser Thr Asn Tyr Asn Glu Lys Phe Lys
1               5                   10                  15

Ser

<210> SEQ ID NO 9
<211> LENGTH: 17
<212> TYPE: PRT
<213> ORGANISM: Artificial Sequence
<220> FEATURE:
<223> OTHER INFORMATION: F107-7H5 CDR L1-B

<400> SEQUENCE: 9

Lys Ser Ser Gln Ser Leu Leu Asn Ser Arg Thr Arg Lys Ile Tyr Leu
1               5                   10                  15

Ala

<210> SEQ ID NO 10
<211> LENGTH: 7
<212> TYPE: PRT
<213> ORGANISM: Artificial Sequence
<220> FEATURE:
<223> OTHER INFORMATION: F107-7H5 CDR L2-B

<400> SEQUENCE: 10

Trp Ala Ser Thr Arg Gln Ser
1               5

<210> SEQ ID NO 11
<211> LENGTH: 8
<212> TYPE: PRT
<213> ORGANISM: Artificial Sequence
<220> FEATURE:
<223> OTHER INFORMATION: F107-7H5/F107 & 8D12 CDR L3-B

<400> SEQUENCE: 11

Lys Gln Ser Tyr Asn Leu Trp Thr
1               5

<210> SEQ ID NO 12
<211> LENGTH: 10
<212> TYPE: PRT
<213> ORGANISM: Artificial Sequence
```

<220> FEATURE:
<223> OTHER INFORMATION: F107-7H5 CDR H1-B

<400> SEQUENCE: 12

Gly Tyr Thr Phe Thr Ser Tyr Trp Ile Asn
1               5                   10

<210> SEQ ID NO 13
<211> LENGTH: 17
<212> TYPE: PRT
<213> ORGANISM: Artificial Sequence
<220> FEATURE:
<223> OTHER INFORMATION: F107-7H5 CDR H2-B

<400> SEQUENCE: 13

Asn Ile Tyr Pro Asp Ser Ser Thr Asn Tyr Asn Glu Lys Phe Lys
1               5                   10                  15

Ser

<210> SEQ ID NO 14
<211> LENGTH: 9
<212> TYPE: PRT
<213> ORGANISM: Artificial Sequence
<220> FEATURE:
<223> OTHER INFORMATION: F107-7H5 CDR H3-B

<400> SEQUENCE: 14

Asp Thr Tyr Gly Gly Ser Pro Asp Tyr
1               5

<210> SEQ ID NO 15
<211> LENGTH: 17
<212> TYPE: PRT
<213> ORGANISM: Artificial Sequence
<220> FEATURE:
<223> OTHER INFORMATION: F107-8D12 CDR L1-B

<400> SEQUENCE: 15

Lys Ser Ser Gln Ser Leu Leu Asn Thr Arg Thr Arg Lys Asn Tyr Leu
1               5                   10                  15

Ala

<210> SEQ ID NO 16
<211> LENGTH: 7
<212> TYPE: PRT
<213> ORGANISM: Artificial Sequence
<220> FEATURE:
<223> OTHER INFORMATION: F107-8D12 CDR L2-B

<400> SEQUENCE: 16

Trp Ala Ser Thr Arg Glu Ser
1               5

<210> SEQ ID NO 17
<211> LENGTH: 10
<212> TYPE: PRT
<213> ORGANISM: Artificial Sequence
<220> FEATURE:
<223> OTHER INFORMATION: F107-8D12 CDR H1-B

<400> SEQUENCE: 17

Gly Tyr Thr Phe Ile Ser Phe Trp Ile Asn
1               5                   10

<210> SEQ ID NO 18
<211> LENGTH: 17
<212> TYPE: PRT
<213> ORGANISM: Artificial Sequence
<220> FEATURE:
<223> OTHER INFORMATION: F107-8D12 CDR H2-B

<400> SEQUENCE: 18

```
Asn Ile Phe Pro Gly Ser Ser Ser Thr Asn Tyr Asn Glu Lys Phe Lys
1               5                   10                  15
Ser
```

<210> SEQ ID NO 19
<211> LENGTH: 9
<212> TYPE: PRT
<213> ORGANISM: Artificial Sequence
<220> FEATURE:
<223> OTHER INFORMATION: F107-8D12 CDR H3-B

<400> SEQUENCE: 19

```
Asp Tyr Tyr Gly Gly Ser Pro Asp Tyr
1               5
```

<210> SEQ ID NO 20
<211> LENGTH: 11
<212> TYPE: PRT
<213> ORGANISM: Artificial Sequence
<220> FEATURE:
<223> OTHER INFORMATION: F111-5E9 CDR L1-B

<400> SEQUENCE: 20

```
Arg Ala Ser Gln Asp Ile Asn Asn Tyr Leu Asn
1               5                   10
```

<210> SEQ ID NO 21
<211> LENGTH: 7
<212> TYPE: PRT
<213> ORGANISM: Artificial Sequence
<220> FEATURE:
<223> OTHER INFORMATION: F111-5E9 CDR L2-B

<400> SEQUENCE: 21

```
Tyr Ile Ser Arg Leu His Ser
1               5
```

<210> SEQ ID NO 22
<211> LENGTH: 9
<212> TYPE: PRT
<213> ORGANISM: Artificial Sequence
<220> FEATURE:
<223> OTHER INFORMATION: F111-5E9  CDR L3-B

<400> SEQUENCE: 22

```
Gln Gln Gly Asn Thr Leu Pro Phe Thr
1               5
```

<210> SEQ ID NO 23
<211> LENGTH: 5
<212> TYPE: PRT
<213> ORGANISM: Artificial Sequence
<220> FEATURE:
<223> OTHER INFORMATION: F111-5E9 CDR H1-B

<400> SEQUENCE: 23

```
Lys Tyr Gly Met Asn
1               5
```

```
<210> SEQ ID NO 24
<211> LENGTH: 17
<212> TYPE: PRT
<213> ORGANISM: Artificial Sequence
<220> FEATURE:
<223> OTHER INFORMATION: F111-5E9 CDR H2-B

<400> SEQUENCE: 24

Trp Ile Asn Thr Tyr Thr Gly Glu Pro Thr Tyr Ala Asp Asp Phe Lys
1               5                   10                  15
Gly

<210> SEQ ID NO 25
<211> LENGTH: 13
<212> TYPE: PRT
<213> ORGANISM: Artificial Sequence
<220> FEATURE:
<223> OTHER INFORMATION: F111-5E9 CDR H3-B

<400> SEQUENCE: 25

Gly Gly Tyr Tyr Ser Asn Pro Ile Tyr Pro Met Asp Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: F111-3C8 CDR L1-B

<400> SEQUENCE: 26

Ser Ala Ser Ser Ser Val Ser Tyr Met Tyr
1               5                   10

<210> SEQ ID NO 27
<211> LENGTH: 7
<212> TYPE: PRT
<213> ORGANISM: Artificial Sequence
<220> FEATURE:
<223> OTHER INFORMATION: F111-3C8 CDR L2-B

<400> SEQUENCE: 27

Arg Thr Ser Asn Leu Ala Ser
1               5

<210> SEQ ID NO 28
<211> LENGTH: 9
<212> TYPE: PRT
<213> ORGANISM: Artificial Sequence
<220> FEATURE:
<223> OTHER INFORMATION: F111-3C8 CDR L3-B

<400> SEQUENCE: 28

Gln Gln Tyr His Asn Tyr Pro Pro Thr
1               5

<210> SEQ ID NO 29
<211> LENGTH: 10
<212> TYPE: PRT
<213> ORGANISM: Artificial Sequence
<220> FEATURE:
<223> OTHER INFORMATION: F111-3C8 CDR H1-B

<400> SEQUENCE: 29

Gly Tyr Thr Phe Thr Ser Tyr Trp Met His
1               5                   10
```

```
<210> SEQ ID NO 30
<211> LENGTH: 17
<212> TYPE: PRT
<213> ORGANISM: Artificial Sequence
<220> FEATURE:
<223> OTHER INFORMATION: F111-3C8 CDR H2-B

<400> SEQUENCE: 30

Asn Ile Asn Pro Asn Ser Thr Ser Ala Asp Tyr Asn Glu Lys Phe Lys
1               5                   10                  15
Arg

<210> SEQ ID NO 31
<211> LENGTH: 11
<212> TYPE: PRT
<213> ORGANISM: Artificial Sequence
<220> FEATURE:
<223> OTHER INFORMATION: F111-3C8 CDR H3-B

<400> SEQUENCE: 31

Pro Leu Met Gly Pro Tyr Trp Tyr Phe Asp Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: F107-10G1 CDR L1-B

<400> SEQUENCE: 32

Lys Ala Ser Gln Asp Val Thr Thr Ala Val Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: F107-10G1 CDR L2-B

<400> SEQUENCE: 33

Trp Ala Ser Thr Arg His Thr
1               5

<210> SEQ ID NO 34
<211> LENGTH: 9
<212> TYPE: PRT
<213> ORGANISM: Artificial Sequence
<220> FEATURE:
<223> OTHER INFORMATION: F107-10G1 CDR L3-B

<400> SEQUENCE: 34

Gln Gln His Phe Thr Thr Pro Leu Thr
1               5

<210> SEQ ID NO 35
<211> LENGTH: 5
<212> TYPE: PRT
<213> ORGANISM: Artificial Sequence
<220> FEATURE:
<223> OTHER INFORMATION: F107-10G1 CDR H1-B

<400> SEQUENCE: 35

Asn Tyr Gly Met Ser
1               5
```

```
<210> SEQ ID NO 36
<211> LENGTH: 17
<212> TYPE: PRT
<213> ORGANISM: Artificial Sequence
<220> FEATURE:
<223> OTHER INFORMATION: F107-10G1 CDR H2-B

<400> SEQUENCE: 36

Ser Ile Ser Gly Gly Gly Gly Arg Thr Tyr Tyr Leu Asp Asn Val Lys
1               5                   10                  15

Gly

<210> SEQ ID NO 37
<211> LENGTH: 11
<212> TYPE: PRT
<213> ORGANISM: Artificial Sequence
<220> FEATURE:
<223> OTHER INFORMATION: F107-10G1 CDR H3-B

<400> SEQUENCE: 37

Gly Ala Arg Ala Ser Tyr Phe Ala Met Asp Tyr
1               5                   10

<210> SEQ ID NO 38
<211> LENGTH: 112
<212> TYPE: PRT
<213> ORGANISM: Artificial Sequence
<220> FEATURE:
<223> OTHER INFORMATION: F107-7H5 VL

<400> SEQUENCE: 38

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Ile Tyr Leu Ala Trp Tyr Gln Gln Lys Pro Gly Gln
        35                  40                  45

Ser Pro Lys Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

<210> SEQ ID NO 39
<211> LENGTH: 118
<212> TYPE: PRT
<213> ORGANISM: Artificial Sequence
<220> FEATURE:
<223> OTHER INFORMATION: F107-7H5 VH

<400> SEQUENCE: 39

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Asp Ser Ser Thr Asn Tyr Asn Glu Lys Phe
    50                  55                  60
```

```
Lys Ser Lys Ala Thr Leu Thr Val Asp Lys Ser Ser Thr Thr Ala Tyr
 65                  70                  75                  80

Ile Gln Phe Ser Ser Leu Thr Ser Glu Asp Ser Ala Val Tyr Tyr Cys
                 85                  90                  95

Thr Arg Asp Thr Tyr Gly Gly Ser Pro Asp Tyr Trp Gly Gln Gly Thr
            100                 105                 110

Thr Leu Thr Val Ser Ser
            115
```

<210> SEQ ID NO 40
<211> LENGTH: 112
<212> TYPE: PRT
<213> ORGANISM: Artificial Sequence
<220> FEATURE:
<223> OTHER INFORMATION: F107-8D12 VL

<400> SEQUENCE: 40

```
Asp Ile Val Met Ser Gln Ser Pro Ser Ser Leu Ala Val Ser Ala Gly
  1               5                  10                  15

Glu Arg Val Thr Met Ser Cys Lys Ser Ser Gln Ser Leu Leu Asn Thr
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Leu Trp Thr Phe Gly Gly Gly Thr Lys Leu Glu Ile Lys
            100                 105                 110
```

<210> SEQ ID NO 41
<211> LENGTH: 118
<212> TYPE: PRT
<213> ORGANISM: Artificial Sequence
<220> FEATURE:
<223> OTHER INFORMATION: F107-8D12 VH

<400> SEQUENCE: 41

```
Gln Val Gln Leu Gln Gln Pro Gly Ala Glu Leu Val Lys Pro Gly Ala
  1               5                  10                  15

Ser Val Gln Leu Ser Cys Lys Ala Ser Gly Tyr Thr Phe Ile Ser Phe
                 20                  25                  30

Trp Ile Asn Trp Val Lys Gln Arg Pro Gly Gln Gly Leu Glu Trp Met
             35                  40                  45

Gly Asn Ile Phe Pro Gly Ser Ser Thr Asn Tyr Asn Glu Lys Phe
 50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Asp Tyr Tyr Gly Gly Ser Pro Asp Tyr Trp Gly Gln Gly Thr
            100                 105                 110

Thr Leu Thr Val Ser Ser
            115
```

```
<210> SEQ ID NO 42
<211> LENGTH: 106
<212> TYPE: PRT
<213> ORGANISM: Artificial Sequence
<220> FEATURE:
<223> OTHER INFORMATION: F111-3C8 VL

<400> SEQUENCE: 42

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Asn Tyr Pro Pro Thr
                85                  90                  95

Phe Gly Gly Gly Thr Lys Leu Glu Ile Lys
            100                 105

<210> SEQ ID NO 43
<211> LENGTH: 120
<212> TYPE: PRT
<213> ORGANISM: Artificial Sequence
<220> FEATURE:
<223> OTHER INFORMATION: F111-3C8 VH

<400> SEQUENCE: 43

Gln Val Gln Leu Gln Gln Pro Gly Ala Glu Leu Gly Lys Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Arg Val Pro Gly Gln Gly Leu Glu Trp Ile
        35                  40                  45

Gly Asn Ile Asn Pro Asn Ser Thr Ser Ala Asp Tyr Asn Glu Lys Phe
    50                  55                  60

Lys Arg Lys Ala Thr Leu Thr Val Asp Lys Ser Ser Ser Thr Ala Tyr
65                  70                  75                  80

Met Gln Leu Ser Thr Leu Thr Ser Glu Asp Ser Ala Val Tyr Tyr Cys
                85                  90                  95

Thr Arg Pro Leu Met Gly Pro Tyr Trp Tyr Phe Asp Val Trp Gly Thr
            100                 105                 110

Gly Thr Thr Val Thr Val Ser Ser
        115                 120

<210> SEQ ID NO 44
<211> LENGTH: 107
<212> TYPE: PRT
<213> ORGANISM: Artificial Sequence
<220> FEATURE:
<223> OTHER INFORMATION: F111-5E9 VL

<400> SEQUENCE: 44

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30
```

```
Leu Asn Trp Tyr Gln Gln Lys Pro Asp Gly Thr Val Lys Leu Leu Ile
            35                  40                  45

Tyr Tyr Ile Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Leu
 65                  70                  75                  80

Glu Asp Val Ala Thr Tyr Phe Cys Gln Gln Gly Asn Thr Leu Pro Phe
                 85                  90                  95

Thr Phe Gly Ser Gly Thr Lys Leu Glu Ile Lys
            100                 105
```

<210> SEQ ID NO 45
<211> LENGTH: 122
<212> TYPE: PRT
<213> ORGANISM: Artificial Sequence
<220> FEATURE:
<223> OTHER INFORMATION: F111-5E9 VH

<400> SEQUENCE: 45

```
Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Lys Tyr
             20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Thr Thr Glu Asp Met Val Thr Tyr Phe Cys
                 85                  90                  95

Ala Lys Gly Gly Tyr Tyr Ser Asn Pro Ile Tyr Pro Met Asp Tyr Trp
            100                 105                 110

Gly Gln Gly Thr Ser Val Thr Val Ser Ser
            115                 120
```

<210> SEQ ID NO 46
<211> LENGTH: 107
<212> TYPE: PRT
<213> ORGANISM: Artificial Sequence
<220> FEATURE:
<223> OTHER INFORMATION: F107-10G1 VL

<400> SEQUENCE: 46

```
Val Ile Val Met Thr Gln Ser His Lys Phe Met Ser Thr Ser Val Gly
 1               5                  10                  15

Asp Arg Val Ser Ile Thr Cys Lys Ala Ser Gln Asp Val Thr Thr Ala
             20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
 50                  55                  60

Ser Gly Ser Gly Thr Asp Tyr Ser Leu Thr Ile Ser Asn Val Gln Thr
 65                  70                  75                  80

Glu Asp Leu Ala Phe Tyr Tyr Cys Gln Gln His Phe Thr Thr Pro Leu
                 85                  90                  95

Thr Phe Gly Ala Gly Thr Lys Leu Glu Leu Lys
            100                 105
```

```
<210> SEQ ID NO 47
<211> LENGTH: 120
<212> TYPE: PRT
<213> ORGANISM: Artificial Sequence
<220> FEATURE:
<223> OTHER INFORMATION: F107-10G1 VH

<400> SEQUENCE: 47

Glu Val Asn Leu Val Glu Ser Gly Gly Gly Val Val Lys Pro Gly Ala
1               5                   10                  15

Ser Leu Lys Leu Ser Cys Glu Ala Ser Gly Phe Thr Phe Ser Asn Tyr
            20                  25                  30

Gly Met Ser Trp Val Arg Gln Thr Ser Asp Lys Arg Leu Glu Trp Val
        35                  40                  45

Ala Ser Ile Ser Gly Gly Gly Arg Thr Tyr Tyr Leu Asp Asn Val
    50                  55                  60

Lys Gly Arg Phe Ile Ile Ser Arg Glu Asn Ala Lys Asn Thr Leu Tyr
65                  70                  75                  80

Leu Gln Met Ser Ser Leu Lys Ser Glu Asp Thr Ala Leu Phe Tyr Cys
                85                  90                  95

Ala Arg Gly Ala Arg Ala Ser Tyr Phe Ala Met Asp Tyr Trp Gly Gln
            100                 105                 110

Gly Ser Ser Val Thr Val Ser Ser
        115                 120

<210> SEQ ID NO 48
<211> LENGTH: 219
<212> TYPE: PRT
<213> ORGANISM: Artificial Sequence
<220> FEATURE:
<223> OTHER INFORMATION: Chimeric F107-7H5 light chain

<400> SEQUENCE: 48

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Ile Tyr Leu Ala Trp Tyr Gln Gln Lys Pro Gly Gln
        35                  40                  45

Ser Pro Lys Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 49
<211> LENGTH: 447
<212> TYPE: PRT
<213> ORGANISM: Artificial Sequence
<220> FEATURE:
<223> OTHER INFORMATION: Chimeric F107-7H5 heavy chain

<400> SEQUENCE: 49

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Asp Ser Ser Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Ile Gln Phe Ser Ser Leu Thr Ser Glu Asp Ser Ala Val Tyr Tyr Cys
                85                  90                  95

Thr Arg Asp Thr Tyr Gly Gly Ser Pro Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 50
<211> LENGTH: 219
<212> TYPE: PRT
<213> ORGANISM: Artificial Sequence
<220> FEATURE:
<223> OTHER INFORMATION: Chimeric F107-8D12 light chain

<400> SEQUENCE: 50

Asp Ile Val Met Ser Gln Ser Pro Ser Ser Leu Ala Val Ser Ala Gly
1               5                   10                  15

Glu Arg Val Thr Met Ser Cys Lys Ser Ser Gln Ser Leu Leu Asn Thr
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 51
<211> LENGTH: 447
<212> TYPE: PRT
<213> ORGANISM: Artificial Sequence
```

<220> FEATURE:
<223> OTHER INFORMATION: Chimeric F107-8D12 heavy chain

<400> SEQUENCE: 51

| | | | | | | | | | | | | | | | |
|---|---|---|---|---|---|---|---|---|---|---|---|---|---|---|---|
| Gln | Val | Gln | Leu | Gln | Gln | Pro | Gly | Ala | Glu | Leu | Val | Lys | Pro | Gly | Ala |
| 1 | | | | 5 | | | | | 10 | | | | | 15 | |
| Ser | Val | Gln | Leu | Ser | Cys | Lys | Ala | Ser | Gly | Tyr | Thr | Phe | Ile | Ser | Phe |
| | | | 20 | | | | | 25 | | | | | 30 | | |
| Trp | Ile | Asn | Trp | Val | Lys | Gln | Arg | Pro | Gly | Gln | Gly | Leu | Glu | Trp | Met |
| | | 35 | | | | | 40 | | | | | 45 | | | |
| Gly | Asn | Ile | Phe | Pro | Gly | Ser | Ser | Thr | Asn | Tyr | Asn | Glu | Lys | Phe |
| 50 | | | | | 55 | | | | | 60 | | | | |
| Lys | Ser | Lys | Ala | Thr | Leu | Thr | Val | Asp | Lys | Ser | Ser | Thr | Ala | Tyr |
| 65 | | | | | 70 | | | | | 75 | | | | 80 |
| Met | Gln | Leu | Ser | Ser | Leu | Thr | Ser | Glu | Asp | Ser | Ala | Val | Tyr | Phe | Cys |
| | | | | 85 | | | | | 90 | | | | | 95 | |
| Ala | Arg | Asp | Tyr | Tyr | Gly | Gly | Ser | Pro | Asp | Tyr | Trp | Gly | Gln | Gly | Thr |
| | | | | 100 | | | | | 105 | | | | | 110 | |
| Thr | Leu | Thr | Val | Ser | Ser | Ala | Ser | Thr | Lys | Gly | Pro | Ser | Val | Phe | Pro |
| | | | 115 | | | | | 120 | | | | | 125 | | |
| Leu | Ala | Pro | Ser | Ser | Lys | Ser | Thr | Ser | Gly | Gly | Thr | Ala | Ala | Leu | Gly |
| 130 | | | | | 135 | | | | | 140 | | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | | 195 | | | | | 200 | | | | | 205 | | |
| Asn | Thr | Lys | Val | Asp | Lys | Lys | Val | Glu | Pro | Lys | Ser | Cys | Asp | Lys | Thr |
| | | 210 | | | | | 215 | | | | | 220 | | | |
| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | | 275 | | | | | 280 | | | | | 285 | | |
| Lys | Thr | Lys | Pro | Arg | Glu | Glu | Gln | Tyr | Asn | Ser | Thr | Tyr | Arg | Val | Val |
| | | 290 | | | | | 295 | | | | | 300 | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Arg | Asp | Glu | Leu | Thr | Lys | Asn | Gln | Val | Ser | Leu | Thr | Cys |
| | | | 355 | | | | | 360 | | | | | 365 | | |
| Leu | Val | Lys | Gly | Phe | Tyr | Pro | Ser | Asp | Ile | Ala | Val | Glu | Trp | Glu | Ser |
| | | 370 | | | | | 375 | | | | | 380 | | | |
| Asn | Gly | Gln | Pro | Glu | Asn | Asn | Tyr | Lys | Thr | Thr | Pro | Pro | Val | Leu | Asp |
| 385 | | | | | 390 | | | | | 395 | | | | | 400 |

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
            435                 440                 445

<210> SEQ ID NO 52
<211> LENGTH: 213
<212> TYPE: PRT
<213> ORGANISM: Artificial Sequence
<220> FEATURE:
<223> OTHER INFORMATION: Chimeric F111-3C8 light chain

<400> SEQUENCE: 52

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Asn Tyr Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 53
<211> LENGTH: 449
<212> TYPE: PRT
<213> ORGANISM: Artificial Sequence
<220> FEATURE:
<223> OTHER INFORMATION: Chimeric F111-3C8 heavy chain

<400> SEQUENCE: 53

Gln Val Gln Leu Gln Gln Pro Gly Ala Glu Leu Gly Lys Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Arg Val Pro Gly Gln Gly Leu Glu Trp Ile
        35                  40                  45
```

```
Gly Asn Ile Asn Pro Asn Ser Thr Ser Ala Asp Tyr Asn Glu Lys Phe
 50                  55                  60
Lys Arg Lys Ala Thr Leu Thr Val Asp Lys Ser Ser Thr Ala Tyr
 65                  70                  75                  80
Met Gln Leu Ser Thr Leu Thr Ser Glu Asp Ser Ala Val Tyr Tyr Cys
                 85                  90                  95
Thr Arg Pro Leu Met Gly Pro Tyr Trp Tyr Phe Asp Val Trp Gly Thr
                100                 105                 110
Gly Thr Thr Val Thr Val Ser Ser Ala Ser Thr Lys Gly Pro Ser Val
             115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly
```

```
<210> SEQ ID NO 54
<211> LENGTH: 214
<212> TYPE: PRT
<213> ORGANISM: Artificial Sequence
<220> FEATURE:
<223> OTHER INFORMATION: Chimeric F111-5E9 light chain

<400> SEQUENCE: 54

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Ile Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Leu
65                  70                  75                  80

Glu Asp Val Ala Thr Tyr Phe Cys Gln Gln Gly Asn Thr Leu Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 55
<211> LENGTH: 451
<212> TYPE: PRT
<213> ORGANISM: Artificial Sequence
<220> FEATURE:
<223> OTHER INFORMATION: Chimeric F111-5E9 heavy chain

<400> SEQUENCE: 55

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Thr Thr Glu Asp Met Val Thr Tyr Phe Cys
                85                  90                  95
```

```
Ala Lys Gly Gly Tyr Tyr Ser Asn Pro Ile Tyr Pro Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 56
<211> LENGTH: 214
<212> TYPE: PRT
<213> ORGANISM: Artificial Sequence
<220> FEATURE:
<223> OTHER INFORMATION: Chimeric F107-10G1 light chain
```

-continued

<400> SEQUENCE: 56

Val Ile Val Met Thr Gln Ser His Lys Phe Met Ser Thr Ser Val Gly
1               5                   10                  15

Asp Arg Val Ser Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Ser Leu Thr Ile Ser Asn Val Gln Thr
65                  70                  75                  80

Glu Asp Leu Ala Phe Tyr Tyr Cys Gln Gln His Phe Thr Thr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 57
<211> LENGTH: 449
<212> TYPE: PRT
<213> ORGANISM: Artificial Sequence
<220> FEATURE:
<223> OTHER INFORMATION: Chimeric F107-10G1 heavy chain

<400> SEQUENCE: 57

Glu Val Asn Leu Val Glu Ser Gly Gly Gly Val Val Lys Pro Gly Ala
1               5                   10                  15

Ser Leu Lys Leu Ser Cys Glu Ala Ser Gly Phe Thr Phe Ser Asn Tyr
            20                  25                  30

Gly Met Ser Trp Val Arg Gln Thr Ser Asp Lys Arg Leu Glu Trp Val
        35                  40                  45

Ala Ser Ile Ser Gly Gly Gly Arg Thr Tyr Tyr Leu Asp Asn Val
    50                  55                  60

Lys Gly Arg Phe Ile Ile Ser Arg Glu Asn Ala Lys Asn Thr Leu Tyr
65                  70                  75                  80

Leu Gln Met Ser Ser Leu Lys Ser Glu Asp Thr Ala Leu Phe Tyr Cys
                85                  90                  95

Ala Arg Gly Ala Arg Ala Ser Tyr Phe Ala Met Asp Tyr Trp Gly Gln
            100                 105                 110

Gly Ser Ser Val Thr Val Ser Ser Ala Ser Thr Lys Gly Pro Ser Val
        115                 120                 125

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 58
<211> LENGTH: 460
<212> TYPE: PRT
<213> ORGANISM: Artificial Sequence
<220> FEATURE:
<223> OTHER INFORMATION: rhAXL-ECD

<400> SEQUENCE: 58

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30
```

-continued

```
Glu Glu Ser Pro Phe Val Gly Asn Pro Gly Asn Ile Thr Gly Ala Arg
             35                  40                  45
Gly Leu Thr Gly Thr Leu Arg Cys Gln Leu Gln Val Gln Gly Glu Pro
         50                  55                  60
Pro Glu Val His Trp Leu Arg Asp Gly Gln Ile Leu Glu Leu Ala Asp
 65                  70                  75                  80
Ser Thr Gln Thr Gln Val Pro Leu Gly Glu Asp Glu Gln Asp Asp Trp
                 85                  90                  95
Ile Val Val Ser Gln Leu Arg Ile Thr Ser Leu Gln Leu Ser Asp Thr
            100                 105                 110
Gly Gln Tyr Gln Cys Leu Val Phe Leu Gly His Gln Thr Phe Val Ser
        115                 120                 125
Gln Pro Gly Tyr Val Gly Leu Glu Gly Leu Pro Tyr Phe Leu Glu Glu
    130                 135                 140
Pro Glu Asp Arg Thr Val Ala Ala Asn Thr Pro Phe Asn Leu Ser Cys
145                 150                 155                 160
Gln Ala Gln Gly Pro Pro Glu Pro Val Asp Leu Leu Trp Leu Gln Asp
                165                 170                 175
Ala Val Pro Leu Ala Thr Ala Pro Gly His Gly Pro Gln Arg Ser Leu
            180                 185                 190
His Val Pro Gly Leu Asn Lys Thr Ser Ser Phe Ser Cys Glu Ala His
        195                 200                 205
Asn Ala Lys Gly Val Thr Thr Ser Arg Thr Ala Thr Ile Thr Val Leu
    210                 215                 220
Pro Gln Gln Pro Arg Asn Leu His Leu Val Ser Arg Gln Pro Thr Glu
225                 230                 235                 240
Leu Glu Val Ala Trp Thr Pro Gly Leu Ser Gly Ile Tyr Pro Leu Thr
                245                 250                 255
His Cys Thr Leu Gln Ala Val Leu Ser Asp Asp Gly Met Gly Ile Gln
            260                 265                 270
Ala Gly Glu Pro Asp Pro Pro Glu Glu Pro Leu Thr Ser Gln Ala Ser
        275                 280                 285
Val Pro Pro His Gln Leu Arg Leu Gly Ser Leu His Pro His Thr Pro
    290                 295                 300
Tyr His Ile Arg Val Ala Cys Thr Ser Ser Gln Gly Pro Ser Ser Trp
305                 310                 315                 320
Thr His Trp Leu Pro Val Glu Thr Pro Glu Gly Val Pro Leu Gly Pro
                325                 330                 335
Pro Glu Asn Ile Ser Ala Thr Arg Asn Gly Ser Gln Ala Phe Val His
            340                 345                 350
Trp Gln Glu Pro Arg Ala Pro Leu Gln Gly Thr Leu Leu Gly Tyr Arg
        355                 360                 365
Leu Ala Tyr Gln Gly Gln Asp Thr Pro Glu Val Leu Met Asp Ile Gly
    370                 375                 380
Leu Arg Gln Glu Val Thr Leu Glu Leu Gln Gly Asp Gly Ser Val Ser
385                 390                 395                 400
Asn Leu Thr Val Cys Val Ala Ala Tyr Thr Ala Ala Gly Asp Gly Pro
                405                 410                 415
Trp Ser Leu Pro Val Pro Leu Glu Ala Trp Arg Pro Gly Gln Ala Gln
            420                 425                 430
```

```
Pro Val His Gln Leu Val Lys Glu Pro Ser Thr Pro Ala Phe Ser Trp
            435                 440                 445

Pro Trp Trp Gly Ser Gly Gly Gly Ser Ser Thr Gly
    450                 455                 460

<210> SEQ ID NO 59
<211> LENGTH: 20
<212> TYPE: PRT
<213> ORGANISM: Artificial Sequence
<220> FEATURE:
<223> OTHER INFORMATION: Light chain signal sequence

<400> SEQUENCE: 59

Met Val Leu Gln Thr Gln Val Phe Ile Ser Leu Leu Trp Ile Ser
1               5                   10                  15

Gly Ala Tyr Gly
            20

<210> SEQ ID NO 60
<211> LENGTH: 19
<212> TYPE: PRT
<213> ORGANISM: Artificial Sequence
<220> FEATURE:
<223> OTHER INFORMATION: Heavy chain signal sequence

<400> SEQUENCE: 60

Met Asp Trp Thr Trp Arg Ile Leu Phe Leu Val Ala Ala Ala Thr Gly
1               5                   10                  15

Thr His Ala

<210> SEQ ID NO 61
<211> LENGTH: 339
<212> TYPE: DNA
<213> ORGANISM: Artificial Sequence
<220> FEATURE:
<223> OTHER INFORMATION: F107-7H5 VL sequence

<400> SEQUENCE: 61
gacattgtga tgtcacagtc tccatcctcc ctggctgtgt cagcaggaga gaaggtcact      60
atgagctgca atccagtca gagtctgctc aacagtagaa cccgaaagat ctacttggct     120
tggtaccagc agaaaccagg tcagtctcct aaactgctga tctattggc atccactagg     180 caatctgggg tccctgatcg cttcacaggc agtggatctg ggacagattt cactctcacc     240
atcagcagtg tgcaggctga agacctggca gtttattact gcaagcaatc ttataatctg     300
tggacgttcg gtggaggcac caagctggaa atcaaacgg                            339

<210> SEQ ID NO 62
<211> LENGTH: 354
<212> TYPE: DNA
<213> ORGANISM: Artificial Sequence
<220> FEATURE:
<223> OTHER INFORMATION: F107-7H5 VH sequence

<400> SEQUENCE: 62
caggtccaac tgcagcagcc tggggctgag cttgtgaagc ctggggcttc agtgaaactg      60
tcctgcaagg cttctggcta cactttcacc agctactgga taaactgggt gaagcagagg     120
cctggacaag ccttgagtg gattggaaat atttatcctg atagtagtag tactaactac     180
aatgagaagt tcaagagcaa ggccacactg actgtagaca gtcctccac cacagcctac     240
```

```
atacagttca gcagcctgac atctgaggac tctgcggtct attattgtac aagagatacc    300
tatggtggta gccctgacta ctggggccaa ggcaccactc tcacagtctc ctca          354
```

<210> SEQ ID NO 63
<211> LENGTH: 336
<212> TYPE: DNA
<213> ORGANISM: Artificial Sequence
<220> FEATURE:
<223> OTHER INFORMATION: F107-8D12 VL sequence

<400> SEQUENCE: 63

```
gacattgtga tgtcacagtc tccatcctcc ctggctgtgt cagcaggaga gagggtcact    60
atgagctgca aatccagtca gagtctgctc aacactagaa cccgaaagaa ctacttggct    120
tggtaccagc agaaaccagg gcagtctcct aaactgctga tctactgggc atccactagg    180
gaatctgggg tccctgatcg cttcacaggc agtggatctg gacagatttt cactctcacc    240
atcagcagtg tgcaggctga agacctggca gtttattact gcaagcaatc ttataatctg    300
tggacgttcg gtggaggcac caagctggaa atcaaa                              336
```

<210> SEQ ID NO 64
<211> LENGTH: 354
<212> TYPE: DNA
<213> ORGANISM: Artificial Sequence
<220> FEATURE:
<223> OTHER INFORMATION: F107-8D12 VH sequence

<400> SEQUENCE: 64

```
caggtccaac tgcagcagcc tggggctgag cttgtgaagc ctggggcttc agtgcagctg    60
tcctgcaagg cttctggcta cactttcatc agcttctgga taaactgggt gaagcagagg    120
cctggacaag gccttgagtg gatgggaaat attttttcctg gtagtagtag tacgaactac    180
aatgagaagt tcaagagcaa ggccacactg actgtagaca atcctccag cacagcctac     240 atgcagctca gcagcctgac atctgaggac tctgcggtct atttttgtgc aagagattac    300
tatggtggta gccctgacta ctggggccaa ggcaccactc tcacagtytc ctca          354
```

<210> SEQ ID NO 65
<211> LENGTH: 321
<212> TYPE: DNA
<213> ORGANISM: Artificial Sequence
<220> FEATURE:
<223> OTHER INFORMATION: F111-5E9 VL sequence

<400> SEQUENCE: 65

```
gatatccaga tgacacagac tacatcctcc ctgtctgcct ctctgggaga cagagtcacc    60
atcagttgca gggcaagtca ggacattaac aattatttaa actggtatca gcagaaacca    120
gatggaactg ttaaactcct gatctactac atatcaagat tacactcagg agtcccatca    180
aggttcagtg gcagtgggtc tggaacagat tattctctca ccattagcaa cctggagcta    240
gaagatgttg ccacttactt ttgccaacag ggtaatacgc ttccattcac gttcggctcg    300
gggacaaagt tggaaataaa a                                              321
```

<210> SEQ ID NO 66
<211> LENGTH: 366
<212> TYPE: DNA
<213> ORGANISM: Artificial Sequence
<220> FEATURE:
<223> OTHER INFORMATION: F111-5E9 VH sequence

<400> SEQUENCE: 66

```
cagatccagt tggtgcagtc tggacctgag ctgaagaagc ctggagagac agtcaagatc    60
tcctgcaagg cttctgggta taccttcaca aatatggaa tgaactgggt aaagcaggct   120
ccaggaaagg gtttaaagtg gatgggctgg ataaacacct acactggaga gccaacatat   180
gctgatgact tcaagggacg gtttgccttc tctttggaaa cctctgccag cactgcctat   240
ttgcagatca caacctcac aactgaggac atggtcacat atttctgtgc aaaggggg    300
tattatagta accctatcta tcctatggac tactgggtc aaggaacctc agtcaccgtc   360
tcctca                                                              366
```

<210> SEQ ID NO 67
<211> LENGTH: 321
<212> TYPE: DNA
<213> ORGANISM: Artificial Sequence
<220> FEATURE:
<223> OTHER INFORMATION: F111-3C8 VL sequence

<400> SEQUENCE: 67

```
caaattgttc tcacccagtc tccagcaatc atgtctgcat ctccagggga aaggtcacc    60
atatcctgca gtgccagctc aagtgtaagt tacatgtatt ggtaccagca gaagccagga   120
tcctccccca aaccctggat ttatcgcaca tccaacctgg cttctggagt ccctgctcgc   180
ttcagtggca gtgggtctgg gacctcttac tctctcacaa tcagcagcat ggaggctgaa   240
gatgctgcca cttattactg ccagcagtat cataattacc acccacgtt cggagggggg   300
accaagctgg aaataaaacg g                                             321
```

<210> SEQ ID NO 68
<211> LENGTH: 360
<212> TYPE: DNA
<213> ORGANISM: Artificial Sequence
<220> FEATURE:
<223> OTHER INFORMATION: F111-3C8 VH sequence

<400> SEQUENCE: 68

```
caggtccaac tgcagcagcc tggggctgaa ctggcaagc ctgggacatc agtgaagctg    60
tcctgcaagg cttctggcta caccttcacc agctattgga tgcactgggt gaagcgggtg   120
cctggacaag gccttgagtg gattggaaat attaatccta atagtactag tgctgactac   180
aatgagaagt tcaagaggaa ggccacattg actgtagaca atcctccag cacagcctac   240
atgcagctca gcaccctgac atctgaggac tctgcggtct actactgtac aagacccta   300
atgggtcctt actggtactt cgatgtctgg ggcacaggga ccacggtcac cgtctcctca   360
```

<210> SEQ ID NO 69
<211> LENGTH: 321
<212> TYPE: DNA
<213> ORGANISM: Artificial Sequence
<220> FEATURE:
<223> OTHER INFORMATION: F107-10G1 VL sequence

<400> SEQUENCE: 69

```
gtcattgtga tgacccagtc tcacaaattc atgtccacat cagtaggaga cagggtcagt    60
atcacctgca aggccagtca ggatgtgact actgctgtag cctggtatca acaaaaacca   120
gggcaatctc ctaaaactact gatttactgg gcatccaccc ggcacactgg agtccctgat   180
cgcttcacag gcagtggatc tgggacagat tattctctca ccatcagcaa tgtgcagact   240
```

-continued gaagacctgg cattttatta ctgtcagcaa cattttacca ctcctctcac gttcggtgct    300
gggaccaagt tggagctgaa a    321

<210> SEQ ID NO 70
<211> LENGTH: 360
<212> TYPE: DNA
<213> ORGANISM: Artificial Sequence
<220> FEATURE:
<223> OTHER INFORMATION: F107-10G1 VH sequence

<400> SEQUENCE: 70
gaagtgaacc tggtggagtc tgggggaggc gtagtgaagc ctggagcgtc tctgaaactc    60
tcctgtgaag cctctggatt cactttcagt aactatggca tgtcttgggt tcgccagact    120
tcagacaaga ggctggagtg ggtcgcatcc attagtggtg gtggtggtag aacctactat    180
ctagacaatg taaagggccg attcatcatc tccagagaga atgccaagaa caccctgtac    240
ctgcaaatga gtagtctgaa gtctgaggac acggccttgt tttactgtgc aagaggagct    300
cgggcctctt actttgctat ggactactgg ggtcaaggaa gttcagtcac cgtctcctca    360

<210> SEQ ID NO 71
<211> LENGTH: 469
<212> TYPE: PRT
<213> ORGANISM: Artificial Sequence
<220> FEATURE:
<223> OTHER INFORMATION: (rh)AXL-ECD His8

<400> SEQUENCE: 71

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

```
Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp Gly Ser Gly Gly Ser Ser Thr Gly His His His
    450                 455                 460

His His His His Gly
465

<210> SEQ ID NO 72
<211> LENGTH: 909
<212> TYPE: PRT
<213> ORGANISM: Artificial Sequence
<220> FEATURE:
<223> OTHER INFORMATION: AXL - full length His6

<400> SEQUENCE: 72

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110
```

-continued

```
Gly Gln Tyr Gln Cys Leu Val Phe Leu Gly His Gln Thr Phe Val Ser
            115                 120                 125
Gln Pro Gly Tyr Val Gly Leu Glu Gly Leu Pro Tyr Phe Leu Glu Glu
        130                 135                 140
Pro Glu Asp Arg Thr Val Ala Ala Asn Thr Pro Phe Asn Leu Ser Cys
145                 150                 155                 160
Gln Ala Gln Gly Pro Pro Glu Pro Val Asp Leu Leu Trp Leu Gln Asp
                165                 170                 175
Ala Val Pro Leu Ala Thr Ala Pro Gly His Gly Pro Gln Arg Ser Leu
            180                 185                 190
His Val Pro Gly Leu Asn Lys Thr Ser Ser Phe Ser Cys Glu Ala His
        195                 200                 205
Asn Ala Lys Gly Val Thr Thr Ser Arg Thr Ala Thr Ile Thr Val Leu
210                 215                 220
Pro Gln Gln Pro Arg Asn Leu His Leu Val Ser Arg Gln Pro Thr Glu
225                 230                 235                 240
Leu Glu Val Ala Trp Thr Pro Gly Leu Ser Gly Ile Tyr Pro Leu Thr
                245                 250                 255
His Cys Thr Leu Gln Ala Val Leu Ser Asp Asp Gly Met Gly Ile Gln
            260                 265                 270
Ala Gly Glu Pro Asp Pro Pro Glu Glu Pro Leu Thr Ser Gln Ala Ser
        275                 280                 285
Val Pro Pro His Gln Leu Arg Leu Gly Ser Leu His Pro His Thr Pro
    290                 295                 300
Tyr His Ile Arg Val Ala Cys Thr Ser Ser Gln Gly Pro Ser Ser Trp
305                 310                 315                 320
Thr His Trp Leu Pro Val Glu Thr Pro Glu Gly Val Pro Leu Gly Pro
                325                 330                 335
Pro Glu Asn Ile Ser Ala Thr Arg Asn Gly Ser Gln Ala Phe Val His
            340                 345                 350
Trp Gln Glu Pro Arg Ala Pro Leu Gln Gly Thr Leu Leu Gly Tyr Arg
        355                 360                 365
Leu Ala Tyr Gln Gly Gln Asp Thr Pro Glu Val Leu Met Asp Ile Gly
    370                 375                 380
Leu Arg Gln Glu Val Thr Leu Glu Leu Gln Gly Asp Gly Ser Val Ser
385                 390                 395                 400
Asn Leu Thr Val Cys Val Ala Ala Tyr Thr Ala Ala Gly Asp Gly Pro
                405                 410                 415
Trp Ser Leu Pro Val Pro Leu Glu Ala Trp Arg Pro Gly Gln Ala Gln
            420                 425                 430
Pro Val His Gln Leu Val Lys Glu Pro Ser Thr Pro Ala Phe Ser Trp
        435                 440                 445
Pro Trp Trp Tyr Val Leu Leu Gly Ala Val Ala Ala Ala Cys Val
    450                 455                 460
Leu Ile Leu Ala Leu Phe Leu Val His Arg Arg Lys Lys Glu Thr Arg
465                 470                 475                 480
Tyr Gly Glu Val Phe Glu Pro Thr Val Glu Arg Gly Glu Leu Val Val
                485                 490                 495
Arg Tyr Arg Val Arg Lys Ser Tyr Ser Arg Arg Thr Thr Glu Ala Thr
            500                 505                 510
Leu Asn Ser Leu Gly Ile Ser Glu Glu Leu Lys Glu Lys Leu Arg Asp
        515                 520                 525
```

Val Met Val Asp Arg His Lys Val Ala Leu Gly Lys Thr Leu Gly Glu
            530                 535                 540
Gly Glu Phe Gly Ala Val Met Glu Gly Gln Leu Asn Gln Asp Ser
545                 550                 555                 560
Ile Leu Lys Val Ala Val Lys Thr Met Lys Ile Ala Ile Cys Thr Arg
                565                 570                 575
Ser Glu Leu Glu Asp Phe Leu Ser Glu Ala Val Cys Met Lys Glu Phe
            580                 585                 590
Asp His Pro Asn Val Met Arg Leu Ile Gly Val Cys Phe Gln Gly Ser
            595                 600                 605
Glu Arg Glu Ser Phe Pro Ala Pro Val Val Ile Leu Pro Phe Met Lys
610                 615                 620
His Gly Asp Leu His Ser Phe Leu Leu Tyr Ser Arg Leu Gly Asp Gln
625                 630                 635                 640
Pro Val Tyr Leu Pro Thr Gln Met Leu Val Lys Phe Met Ala Asp Ile
                645                 650                 655
Ala Ser Gly Met Glu Tyr Leu Ser Thr Lys Arg Phe Ile His Arg Asp
            660                 665                 670
Leu Ala Ala Arg Asn Cys Met Leu Asn Glu Asn Met Ser Val Cys Val
            675                 680                 685
Ala Asp Phe Gly Leu Ser Lys Lys Ile Tyr Asn Gly Asp Tyr Tyr Arg
            690                 695                 700
Gln Gly Arg Ile Ala Lys Met Pro Val Lys Trp Ile Ala Ile Glu Ser
705                 710                 715                 720
Leu Ala Asp Arg Val Tyr Thr Ser Lys Ser Asp Val Trp Ser Phe Gly
                725                 730                 735
Val Thr Met Trp Glu Ile Ala Thr Arg Gly Gln Thr Pro Tyr Pro Gly
            740                 745                 750
Val Glu Asn Ser Glu Ile Tyr Asp Tyr Leu Arg Arg Gly Asn Arg Leu
            755                 760                 765
Lys Gln Pro Ala Asp Cys Leu Asp Gly Leu Tyr Ala Leu Met Ser Arg
            770                 775                 780
Cys Trp Glu Leu Asn Pro Gln Asp Arg Pro Ser Phe Thr Glu Leu Arg
785                 790                 795                 800
Glu Asp Leu Glu Asn Thr Leu Lys Ala Leu Pro Pro Ala Gln Glu Pro
                805                 810                 815
Asp Glu Ile Leu Tyr Val Asn Met Asp Glu Gly Gly Gly Tyr Pro Glu
            820                 825                 830
Pro Pro Gly Ala Ala Gly Gly Ala Asp Pro Pro Thr Gln Pro Asp Pro
            835                 840                 845
Lys Asp Ser Cys Ser Cys Leu Thr Ala Ala Glu Val His Pro Ala Gly
            850                 855                 860
Arg Tyr Val Leu Cys Pro Ser Thr Thr Pro Ser Pro Ala Gln Pro Ala
865                 870                 875                 880
Asp Arg Gly Ser Pro Ala Ala Pro Gly Gln Glu Asp Gly Ala Tyr Leu
                885                 890                 895
Glu Cys Gly Arg Tyr Ala Ser His His His His His
            900                 905

<210> SEQ ID NO 73
<211> LENGTH: 118
<212> TYPE: PRT
<213> ORGANISM: Artificial Sequence
<220> FEATURE:
<223> OTHER INFORMATION: F155-3C7 VH

<400> SEQUENCE: 73

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Ile Phe Thr Asn Phe
            20                  25                  30

Trp Ile Asn Trp Val Lys Gln Arg Pro Gly Gln Gly Leu Glu Trp Ile
        35                  40                  45

Gly Asn Ile Phe Pro Gly Ser Asn Ser Ser Tyr Asn Glu Lys Phe
    50                  55                  60

Lys Asn Lys Ala Thr Leu Thr Val Asp Lys Ser Ser Thr Ala Tyr
65                  70                  75                  80

Met His Leu Ser Ser Leu Thr Ser Glu Asp Ser Ala Val Tyr Tyr Cys
            85                  90                  95

Val Arg Asp Tyr Tyr Gly Gly Ser Pro Asp Tyr Trp Gly Gln Gly Thr
            100                 105                 110

Thr Leu Thr Val Ser Ser
        115

<210> SEQ ID NO 74
<211> LENGTH: 112
<212> TYPE: PRT
<213> ORGANISM: Artificial Sequence
<220> FEATURE:
<223> OTHER INFORMATION: F155-3C7 VL

<400> SEQUENCE: 74

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Lys Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Ala Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Lys His
            85                  90                  95

Ser Tyr Asn Leu Trp Thr Phe Gly Gly Gly Thr Lys Leu Glu Ile Arg
            100                 105                 110

<210> SEQ ID NO 75
<211> LENGTH: 118
<212> TYPE: PRT
<213> ORGANISM: Artificial Sequence
<220> FEATURE:
<223> OTHER INFORMATION: F149-4G4 VH

<400> SEQUENCE: 75

Gln Ile Gln Leu Val Gln Ser Gly Pro Glu Leu Lys Lys Pro Gly Glu
1               5                   10                  15

Thr Val Lys Ile Ser Cys Lys Thr Ser Gly Tyr Thr Phe Thr Tyr Tyr
            20                  25                  30

Gly Ile Asn Trp Val Lys Gln Ala Pro Gly Lys Gly Leu Glu Trp Met
        35                  40                  45

Gly Trp Ile Asn Thr Tyr Leu Gly Glu Pro Thr Tyr Ala Asp Asp Phe
    50                  55                  60

```
Lys Gly Arg Phe Ala Phe Ser Leu Glu Thr Ser Ala Ser Thr Ala Tyr
 65                  70                  75                  80

Leu Gln Ile Asn Asn Leu Arg Asp Glu Asp Met Ala Thr Tyr Phe Cys
                 85                  90                  95

Thr Arg Gly Thr Met Ser Tyr Ser Phe Asp Tyr Trp Gly Gln Gly Thr
            100                 105                 110

Ala Leu Thr Val Ser Ser
            115
```

<210> SEQ ID NO 76
<211> LENGTH: 108
<212> TYPE: PRT
<213> ORGANISM: Artificial Sequence
<220> FEATURE:
<223> OTHER INFORMATION: F149-4G4 VL

<400> SEQUENCE: 76

```
Gln Asn Val Leu Thr Gln Ser Pro Ala Ile Met Ser Ala Ser Pro Gly
 1               5                  10                  15

Glu Glu Val Thr Met Thr Cys Arg Ala Ser Ser Ser Val Ser Ser Ser
             20                  25                  30

Tyr Leu His Trp Tyr Gln Gln Lys Ser Gly Ala Ser Pro Lys Leu Trp
         35                  40                  45

Ile Tyr Ser Thr Ser Lys Leu Ala Ser Gly Val Pro Ala Arg Phe Ser
     50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys His Gln Tyr Ser Gly Asp Pro
                 85                  90                  95

Leu Thr Phe Gly Ser Gly Thr Lys Leu Glu Val Lys
            100                 105
```

<210> SEQ ID NO 77
<211> LENGTH: 8
<212> TYPE: PRT
<213> ORGANISM: Artificial Sequence
<220> FEATURE:
<223> OTHER INFORMATION: F107-10G1 CDR H1-A

<400> SEQUENCE: 77

```
Gly Phe Thr Phe Ser Asn Tyr Gly
 1               5
```

<210> SEQ ID NO 78
<211> LENGTH: 8
<212> TYPE: PRT
<213> ORGANISM: Artificial Sequence
<220> FEATURE:
<223> OTHER INFORMATION: F107-10G1 CDR H2-A

<400> SEQUENCE: 78

```
Ile Ser Gly Gly Gly Gly Arg Thr
 1               5
```

<210> SEQ ID NO 79
<211> LENGTH: 13
<212> TYPE: PRT
<213> ORGANISM: Artificial Sequence
<220> FEATURE:
<223> OTHER INFORMATION: F107-10G1 CDR H3-A

```
<400> SEQUENCE: 79

Ala Arg Gly Ala Arg Ala Ser Tyr Phe Ala Met Asp Tyr
1               5                   10

<210> SEQ ID NO 80
<211> LENGTH: 6
<212> TYPE: PRT
<213> ORGANISM: Artificial Sequence
<220> FEATURE:
<223> OTHER INFORMATION: F107-10G1 CDR L1-A

<400> SEQUENCE: 80

Gln Asp Val Thr Thr Ala
1               5

<210> SEQ ID NO 81
<211> LENGTH: 4
<212> TYPE: PRT
<213> ORGANISM: Artificial Sequence
<220> FEATURE:
<223> OTHER INFORMATION: F107-10G1 CDR L2-A

<400> SEQUENCE: 81

Trp Ala Ser Thr
1

<210> SEQ ID NO 82
<211> LENGTH: 9
<212> TYPE: PRT
<213> ORGANISM: Artificial Sequence
<220> FEATURE:
<223> OTHER INFORMATION: F107-10G1 CDR L3-A

<400> SEQUENCE: 82

Gln Gln His Phe Thr Thr Pro Leu Thr
1               5

<210> SEQ ID NO 83
<211> LENGTH: 8
<212> TYPE: PRT
<213> ORGANISM: Artificial Sequence
<220> FEATURE:
<223> OTHER INFORMATION: F111-5E9 CDR H1-A

<400> SEQUENCE: 83

Gly Tyr Thr Phe Thr Lys Tyr Gly
1               5

<210> SEQ ID NO 84
<211> LENGTH: 8
<212> TYPE: PRT
<213> ORGANISM: Artificial Sequence
<220> FEATURE:
<223> OTHER INFORMATION: F111-5E9 CDR H2-A

<400> SEQUENCE: 84

Ile Asn Thr Tyr Thr Gly Glu Pro
1               5

<210> SEQ ID NO 85
<211> LENGTH: 15
<212> TYPE: PRT
<213> ORGANISM: Artificial Sequence
<220> FEATURE:
<223> OTHER INFORMATION: F111-5E9 CDR H3-A
```

```
<400> SEQUENCE: 85

Ala Lys Gly Gly Tyr Tyr Ser Asn Pro Ile Tyr Pro Met Asp Tyr
1               5                   10                  15

<210> SEQ ID NO 86
<211> LENGTH: 6
<212> TYPE: PRT
<213> ORGANISM: Artificial Sequence
<220> FEATURE:
<223> OTHER INFORMATION: F111-5E9 CDR L1-A

<400> SEQUENCE: 86

Gln Asp Ile Asn Asn Tyr
1               5

<210> SEQ ID NO 87
<211> LENGTH: 4
<212> TYPE: PRT
<213> ORGANISM: Artificial Sequence
<220> FEATURE:
<223> OTHER INFORMATION: F111-5E9 CDR L2-A

<400> SEQUENCE: 87

Tyr Ile Ser Arg
1

<210> SEQ ID NO 88
<211> LENGTH: 9
<212> TYPE: PRT
<213> ORGANISM: Artificial Sequence
<220> FEATURE:
<223> OTHER INFORMATION: F111-5E9 CDR L3-A

<400> SEQUENCE: 88

Gln Gln Gly Asn Thr Leu Pro Phe Thr
1               5

<210> SEQ ID NO 89
<211> LENGTH: 8
<212> TYPE: PRT
<213> ORGANISM: Artificial Sequence
<220> FEATURE:
<223> OTHER INFORMATION: F107-8D12 CDR H1-A

<400> SEQUENCE: 89

Gly Tyr Thr Phe Ile Ser Phe Trp
1               5

<210> SEQ ID NO 90
<211> LENGTH: 8
<212> TYPE: PRT
<213> ORGANISM: Artificial Sequence
<220> FEATURE:
<223> OTHER INFORMATION: F107-8D12 CDR H2-A

<400> SEQUENCE: 90

Ile Phe Pro Gly Ser Ser Ser Thr
1               5

<210> SEQ ID NO 91
<211> LENGTH: 11
<212> TYPE: PRT
<213> ORGANISM: Artificial Sequence
<220> FEATURE:
<223> OTHER INFORMATION: F107-8D12 CDR H3-A
```

<400> SEQUENCE: 91

Ala Arg Asp Tyr Tyr Gly Gly Ser Pro Asp Tyr
1               5                   10

<210> SEQ ID NO 92
<211> LENGTH: 12
<212> TYPE: PRT
<213> ORGANISM: Artificial Sequence
<220> FEATURE:
<223> OTHER INFORMATION: F107-8D12 CDR L1-A

<400> SEQUENCE: 92

Gln Ser Leu Leu Asn Thr Arg Thr Arg Lys Asn Tyr
1               5                   10

<210> SEQ ID NO 93
<211> LENGTH: 4
<212> TYPE: PRT
<213> ORGANISM: Artificial Sequence
<220> FEATURE:
<223> OTHER INFORMATION: F107-8D12 CDR L2-A

<400> SEQUENCE: 93

Trp Ala Ser Thr
1

<210> SEQ ID NO 94
<211> LENGTH: 8
<212> TYPE: PRT
<213> ORGANISM: Artificial Sequence
<220> FEATURE:
<223> OTHER INFORMATION: F107-8D12 CDR L3-A

<400> SEQUENCE: 94

Lys Gln Ser Tyr Asn Leu Trp Thr
1               5

<210> SEQ ID NO 95
<211> LENGTH: 8
<212> TYPE: PRT
<213> ORGANISM: Artificial Sequence
<220> FEATURE:
<223> OTHER INFORMATION: F107-7H5 CDR H1-A

<400> SEQUENCE: 95

Gly Tyr Thr Phe Thr Ser Tyr Trp
1               5

<210> SEQ ID NO 96
<211> LENGTH: 8
<212> TYPE: PRT
<213> ORGANISM: Artificial Sequence
<220> FEATURE:
<223> OTHER INFORMATION: F107-7H5 CDR H2-A

<400> SEQUENCE: 96

Ile Tyr Pro Asp Ser Ser Ser Thr
1               5

<210> SEQ ID NO 97
<211> LENGTH: 11
<212> TYPE: PRT
<213> ORGANISM: Artificial Sequence
<220> FEATURE:
<223> OTHER INFORMATION: F107-7H5 CDR H3-A

<400> SEQUENCE: 97

Thr Arg Asp Thr Tyr Gly Gly Ser Pro Asp Tyr
1               5                   10

<210> SEQ ID NO 98
<211> LENGTH: 12
<212> TYPE: PRT
<213> ORGANISM: Artificial Sequence
<220> FEATURE:
<223> OTHER INFORMATION: F107-7H5 CDR L1-A

<400> SEQUENCE: 98

Gln Ser Leu Leu Asn Ser Arg Thr Arg Lys Ile Tyr
1               5                   10

<210> SEQ ID NO 99
<211> LENGTH: 4
<212> TYPE: PRT
<213> ORGANISM: Artificial Sequence
<220> FEATURE:
<223> OTHER INFORMATION: F107-7H5 CDR L2-A

<400> SEQUENCE: 99

Trp Ala Ser Thr
1

<210> SEQ ID NO 100
<211> LENGTH: 8
<212> TYPE: PRT
<213> ORGANISM: Artificial Sequence
<220> FEATURE:
<223> OTHER INFORMATION: F107-7H5 CDR L3-A

<400> SEQUENCE: 100

Lys Gln Ser Tyr Asn Leu Trp Thr
1               5

<210> SEQ ID NO 101
<211> LENGTH: 8
<212> TYPE: PRT
<213> ORGANISM: Artificial Sequence
<220> FEATURE:
<223> OTHER INFORMATION: F155-3C7 CDR H1-A

<400> SEQUENCE: 101

Gly Tyr Ile Phe Thr Asn Phe Trp
1               5

<210> SEQ ID NO 102
<211> LENGTH: 8
<212> TYPE: PRT
<213> ORGANISM: Artificial Sequence
<220> FEATURE:
<223> OTHER INFORMATION: F155-3C7 CDR H2-A

<400> SEQUENCE: 102

Ile Phe Pro Gly Ser Asn Ser Ser
1               5

<210> SEQ ID NO 103
<211> LENGTH: 11
<212> TYPE: PRT
<213> ORGANISM: Artificial Sequence
<220> FEATURE:
<223> OTHER INFORMATION: F155-3C7 CDR H3-A

<400> SEQUENCE: 103

Val Arg Asp Tyr Tyr Gly Gly Ser Pro Asp Tyr
1               5                   10

<210> SEQ ID NO 104
<211> LENGTH: 12
<212> TYPE: PRT
<213> ORGANISM: Artificial Sequence
<220> FEATURE:
<223> OTHER INFORMATION: F155-3C7 CDR L1-A

<400> SEQUENCE: 104

Gln Ser Leu Leu Asn Ser Lys Thr Arg Lys Asn Tyr
1               5                   10

<210> SEQ ID NO 105
<211> LENGTH: 4
<212> TYPE: PRT
<213> ORGANISM: Artificial Sequence
<220> FEATURE:
<223> OTHER INFORMATION: F155-3C7 CDR L2-A

<400> SEQUENCE: 105

Trp Ala Ser Thr
1

<210> SEQ ID NO 106
<211> LENGTH: 8
<212> TYPE: PRT
<213> ORGANISM: Artificial Sequence
<220> FEATURE:
<223> OTHER INFORMATION: F155-3C7 CDR L3-A

<400> SEQUENCE: 106

Lys His Ser Tyr Asn Leu Trp Thr
1               5

<210> SEQ ID NO 107
<211> LENGTH: 8
<212> TYPE: PRT
<213> ORGANISM: Artificial Sequence
<220> FEATURE:
<223> OTHER INFORMATION: F111-3C8 CDR H1-A

<400> SEQUENCE: 107

Gly Tyr Thr Phe Thr Ser Tyr Trp
1               5

<210> SEQ ID NO 108
<211> LENGTH: 8
<212> TYPE: PRT
<213> ORGANISM: Artificial Sequence
<220> FEATURE:
<223> OTHER INFORMATION: F111-3C8 CDR H2-A

<400> SEQUENCE: 108

Ile Asn Pro Asn Ser Thr Ser Ala
1               5

<210> SEQ ID NO 109
<211> LENGTH: 13
<212> TYPE: PRT
<213> ORGANISM: Artificial Sequence
<220> FEATURE:
<223> OTHER INFORMATION: F111-3C8 CDR H3-A

```
<400> SEQUENCE: 109

Thr Arg Pro Leu Met Gly Pro Tyr Trp Tyr Phe Asp Val
1               5                   10

<210> SEQ ID NO 110
<211> LENGTH: 5
<212> TYPE: PRT
<213> ORGANISM: Artificial Sequence
<220> FEATURE:
<223> OTHER INFORMATION: F111-3C8 CDR L1-A

<400> SEQUENCE: 110

Ser Ser Val Ser Tyr
1               5

<210> SEQ ID NO 111
<211> LENGTH: 4
<212> TYPE: PRT
<213> ORGANISM: Artificial Sequence
<220> FEATURE:
<223> OTHER INFORMATION: F111-3C8 CDR L2-A

<400> SEQUENCE: 111

Arg Thr Ser Asn
1

<210> SEQ ID NO 112
<211> LENGTH: 9
<212> TYPE: PRT
<213> ORGANISM: Artificial Sequence
<220> FEATURE:
<223> OTHER INFORMATION: F111-3C8 CDR L3-A

<400> SEQUENCE: 112

Gln Gln Tyr His Asn Tyr Pro Pro Thr
1               5

<210> SEQ ID NO 113
<211> LENGTH: 8
<212> TYPE: PRT
<213> ORGANISM: Artificial Sequence
<220> FEATURE:
<223> OTHER INFORMATION: F149-4G4 CDR H1-A

<400> SEQUENCE: 113

Gly Tyr Thr Phe Thr Tyr Tyr Gly
1               5

<210> SEQ ID NO 114
<211> LENGTH: 8
<212> TYPE: PRT
<213> ORGANISM: Artificial Sequence
<220> FEATURE:
<223> OTHER INFORMATION: F149-4G4 CDR H2-A

<400> SEQUENCE: 114

Ile Asn Thr Tyr Leu Gly Glu Pro
1               5

<210> SEQ ID NO 115
<211> LENGTH: 11
<212> TYPE: PRT
<213> ORGANISM: Artificial Sequence
<220> FEATURE:
<223> OTHER INFORMATION: F149-4G4 CDR H3-A
```

```
<400> SEQUENCE: 115

Thr Arg Gly Thr Met Ser Tyr Ser Phe Asp Tyr
1               5                  10

<210> SEQ ID NO 116
<211> LENGTH: 8
<212> TYPE: PRT
<213> ORGANISM: Artificial Sequence
<220> FEATURE:
<223> OTHER INFORMATION: F149-4G4 CDR L1-A

<400> SEQUENCE: 116

Ser Ser Ser Val Ser Ser Ser Tyr
1               5

<210> SEQ ID NO 117
<211> LENGTH: 4
<212> TYPE: PRT
<213> ORGANISM: Artificial Sequence
<220> FEATURE:
<223> OTHER INFORMATION: F149-4G4 CDR L2-A

<400> SEQUENCE: 117

Ser Thr Ser Lys
1

<210> SEQ ID NO 118
<211> LENGTH: 9
<212> TYPE: PRT
<213> ORGANISM: Artificial Sequence
<220> FEATURE:
<223> OTHER INFORMATION: F149-4G4 CDR L3-A

<400> SEQUENCE: 118

His Gln Tyr Ser Gly Asp Pro Leu Thr
1               5

<210> SEQ ID NO 119
<211> LENGTH: 115
<212> TYPE: PRT
<213> ORGANISM: Artificial Sequence
<220> FEATURE:
<223> OTHER INFORMATION: NRC-sdAb001

<400> SEQUENCE: 119

Gln Val Lys Leu Glu Glu Ser Gly Gly Gly Leu Val Gln Ala Gly Gly
1               5                   10                  15

Ser Leu Arg Leu Ser Cys Thr Ala Ser Ala Ser Ile Ser Ser Phe Asp
            20                  25                  30

Ile Met Gly Trp Tyr Arg Gln Ala Pro Gly Lys Gln Arg Glu Leu Val
        35                  40                  45

Ala Ala Ile Thr Thr Leu Asp Ile Ala Asn Tyr Arg Asp Ser Val Lys
    50                  55                  60

Gly Arg Phe Thr Ile Ser Arg Asp Asn Ala Lys Asn Thr Val Tyr Leu
65                  70                  75                  80

Gln Met Asp Ser Leu Lys Pro Glu Asp Thr Ala Arg Tyr His Cys Ala
                85                  90                  95

Ala Phe Gln Ser Asp Gln Asn Tyr Trp Gly Gln Gly Thr Gln Val Thr
            100                 105                 110

Val Ser Ser
        115
```

```
<210> SEQ ID NO 120
<211> LENGTH: 127
<212> TYPE: PRT
<213> ORGANISM: Artificial Sequence
<220> FEATURE:
<223> OTHER INFORMATION: NRC-sdAb002

<400> SEQUENCE: 120

Gln Val Gln Leu Val Asp Ser Gly Gly Gly Leu Val Gln Ala Gly Gly
1               5                   10                  15

Ser Leu Arg Leu Ser Cys Ala Thr Ser Thr Arg Thr Val Ser Ser Ala
            20                  25                  30

Val Met Ala Trp Phe Arg Gln Ala Pro Glu Lys Val Arg Asp Phe Val
        35                  40                  45

Gly Phe Ile Thr Asn Ser Gly Asn Ile Leu Tyr Asp Asp Ser Val Lys
    50                  55                  60

Gly Arg Phe Thr Ile Ser Arg Asp Asn Ala Gln Asn Thr Val Tyr Leu
65                  70                  75                  80

Gln Met Asn Ser Leu Lys Pro Glu Asp Thr Ala Val Tyr Tyr Cys Ala
                85                  90                  95

Ala Lys Trp Ser Phe Ser Ser Gly Tyr Gly Asp Leu Arg Arg Ala Ala
            100                 105                 110

Met Tyr Asp Tyr Trp Gly Gln Gly Thr Gln Val Thr Val Ser Ser
        115                 120                 125

<210> SEQ ID NO 121
<211> LENGTH: 119
<212> TYPE: PRT
<213> ORGANISM: Artificial Sequence
<220> FEATURE:
<223> OTHER INFORMATION: NRC-sdAb003

<400> SEQUENCE: 121

Gln Val Gln Leu Val Glu Ser Gly Gly Gly Leu Val Gln Ala Gly Gly
1               5                   10                  15

Ser Leu Arg Leu Ser Cys Ala Ala Ser Gly Val Thr Leu Asp Tyr Thr
            20                  25                  30

Ala Ile Gly Trp Phe Arg Gln Ala Pro Gly Lys Glu Arg Glu Leu Val
        35                  40                  45

Ala Ala Ile Thr Ser Gly Gly Asn Thr Asp Tyr Ala Glu Ser Ala Lys
    50                  55                  60

Gly Arg Phe Arg Ile Ser Arg Asp Asn Ser Lys Asn Thr Ile Tyr Leu
65                  70                  75                  80

Gln Met Asn Ser Leu Lys Pro Glu Asp Thr Gly Val Tyr Tyr Cys Ala
                85                  90                  95

Ala Arg Arg Gly Gly Ala Arg Gly Glu Tyr Asp Tyr Trp Asp Gln Gly
            100                 105                 110

Thr Gln Val Thr Val Ser Ser
        115

<210> SEQ ID NO 122
<211> LENGTH: 125
<212> TYPE: PRT
<213> ORGANISM: Artificial Sequence
<220> FEATURE:
<223> OTHER INFORMATION: NRC-sdAb004
```

<400> SEQUENCE: 122

```
Gln Val Gln Leu Val Glu Ser Gly Gly Gly Val Val Gln Ala Gly Gly
1               5                   10                  15

Ser Leu Arg Leu Ser Cys Ala Phe Ser Arg Gly Ala Phe Asp Thr Tyr
            20                  25                  30

Glu Ile Gly Trp Phe Arg Gln Ala Pro Gly Lys Glu Arg Glu Phe Val
        35                  40                  45

Ala Ala Val Thr Arg Asn Gly Asp Ser Val Val Tyr Ala Asp Ser Leu
    50                  55                  60

Lys Ala Arg Phe Thr Ala Ser Arg Asn Asn Ala Val Asn Thr Ala Tyr
65                  70                  75                  80

Leu His Met Asn Ile Leu Gln Pro Glu Asp Thr Ala Thr Tyr Tyr Cys
                85                  90                  95

Ala Ala Asn Trp Arg Pro Leu Arg Thr Ser Ser Gly Ala Asp Asp Tyr
            100                 105                 110

Ala Asp Trp Gly Gln Gly Thr Gln Val Thr Val Ser Ser
        115                 120                 125
```

<210> SEQ ID NO 123
<211> LENGTH: 118
<212> TYPE: PRT
<213> ORGANISM: Artificial Sequence
<220> FEATURE:
<223> OTHER INFORMATION: NRC-sdAb005

<400> SEQUENCE: 123

```
Gln Val Lys Leu Glu Glu Ser Gly Gly Gly Leu Ala Gln Ala Gly Gly
1               5                   10                  15

Ser Leu Arg Leu Ser Cys Ala Ala Ser Gly Ser Ile Ser Ser Ile Asn
            20                  25                  30

Thr Ile Gly Trp Phe Arg Gln Ala Pro Gly Lys Gln Arg Glu Leu Val
        35                  40                  45

Ala Ala Ser Asp Ser Gly Ala Asn Arg Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Ile Tyr Tyr Cys Arg
                85                  90                  95

Ala Trp Gly Thr Gly Thr Ile Ser Thr Met Tyr Trp Gly Gln Gly Thr
            100                 105                 110

Gln Val Thr Val Ser Ser
        115
```

<210> SEQ ID NO 124
<211> LENGTH: 118
<212> TYPE: PRT
<213> ORGANISM: Artificial Sequence
<220> FEATURE:
<223> OTHER INFORMATION: NRC-sdAb006

<400> SEQUENCE: 124

```
Gln Val Lys Leu Glu Glu Ser Gly Gly Gly Leu Val Gln Ala Gly Ala
1               5                   10                  15

Ser Leu Arg Leu Ser Cys Val Ala Ser Glu Ser Ile Phe Gly Phe Asn
            20                  25                  30

Thr Met Gly Trp Tyr Arg Gln Ala Pro Gly Asn Glu Arg Glu Leu Val
        35                  40                  45
```

```
Ala Ser Ile Ser Asn Ser Lys Arg Thr Met Tyr Ala Asp Ser Val Lys
        50                  55                  60

Gly Arg Phe Thr Ile Ser Arg Asp Asn Ala Lys Asn Thr Val Asn Leu
 65                  70                  75                  80

Gln Met Asn Asn Leu Lys Pro Glu Asp Thr Ala Val Tyr Tyr Cys Arg
                85                  90                  95

Ala Trp Gly Ile Ile Thr Ser Ala Thr Val Tyr Trp Gly Gln Gly Thr
            100                 105                 110

Gln Val Thr Val Ser Ser
            115
```

<210> SEQ ID NO 125
<211> LENGTH: 121
<212> TYPE: PRT
<213> ORGANISM: Artificial Sequence
<220> FEATURE:
<223> OTHER INFORMATION: NRC-sdAb007

<400> SEQUENCE: 125

```
Gln Val Lys Leu Glu Glu Ser Gly Gly Gly Leu Val Gln Ala Gly Gly
 1               5                   10                  15

Ser Leu Arg Leu Ser Cys Ala Thr Ser Thr Arg Thr Val Ser Ser Ala
                20                  25                  30

Val Met Ala Trp Phe Arg Gln Ala Pro Glu Lys Glu Arg Asp Phe Val
            35                  40                  45

Gly Phe Ile Ser Asn Ser Gly Ser Val Tyr Tyr Asp Asp Ser Val Lys
        50                  55                  60

Gly Arg Phe Thr Ile Ser Arg Asp Asn Ala Gln Asn Thr Val Tyr Leu
 65                  70                  75                  80

Gln Met Asn Ser Leu Lys Pro Glu Asp Thr Ala Val Tyr Tyr Cys Ala
                85                  90                  95

Ile Ile Trp Arg Thr Ser Asp Leu Thr Gly Arg Phe Asn Thr Trp Gly
            100                 105                 110

Gln Gly Thr Gln Val Thr Val Ser Ser
        115                 120
```

<210> SEQ ID NO 126
<211> LENGTH: 121
<212> TYPE: PRT
<213> ORGANISM: Artificial Sequence
<220> FEATURE:
<223> OTHER INFORMATION: NRC-sdAb008

<400> SEQUENCE: 126

```
Gln Val Lys Leu Glu Glu Ser Gly Gly Gly Leu Val Gln Ala Gly Gly
 1               5                   10                  15

Ser Leu Arg Leu Ser Cys Ala Ser Gly Ser Ser Gly Met Ile Asn
                20                  25                  30

Thr Met Gly Trp Tyr Arg Gln Ala Pro Gly Lys Gln Arg Glu Leu Val
            35                  40                  45

Ala Arg Arg Ser Thr Gly Gly Thr Thr Asn Tyr Ala Asp Ser Val Lys
        50                  55                  60

Gly Arg Phe Thr Ile Ser Arg Asp Asp Ala Asn Asn Thr Val Tyr Leu
 65                  70                  75                  80

Gln Met Asn Ser Leu Lys Pro Glu Asp Thr Ala Val Tyr Tyr Cys Ala
                85                  90                  95
```

Ile Ile Trp Arg Thr Ser Asp Leu Thr Gly Arg Phe Asn Thr Trp Gly
                100                 105                 110

Gln Gly Thr Gln Val Thr Val Ser Ser
        115                 120

<210> SEQ ID NO 127
<211> LENGTH: 8
<212> TYPE: PRT
<213> ORGANISM: Artificial Sequence
<220> FEATURE:
<223> OTHER INFORMATION: NRC-sdAb001 CDR1-A

<400> SEQUENCE: 127

Ala Ser Ile Ser Ser Phe Asp Ile
1               5

<210> SEQ ID NO 128
<211> LENGTH: 7
<212> TYPE: PRT
<213> ORGANISM: Artificial Sequence
<220> FEATURE:
<223> OTHER INFORMATION: NRC-sdAb001 CDR2-A

<400> SEQUENCE: 128

Ile Thr Thr Leu Asp Ile Ala
1               5

<210> SEQ ID NO 129
<211> LENGTH: 9
<212> TYPE: PRT
<213> ORGANISM: Artificial Sequence
<220> FEATURE:
<223> OTHER INFORMATION: NRC-sdAb001 CDR3-A

<400> SEQUENCE: 129

Ala Ala Phe Gln Ser Asp Gln Asn Tyr
1               5

<210> SEQ ID NO 130
<211> LENGTH: 8
<212> TYPE: PRT
<213> ORGANISM: Artificial Sequence
<220> FEATURE:
<223> OTHER INFORMATION: NRC-sdAb002 CDR1-A

<400> SEQUENCE: 130

Thr Arg Thr Val Ser Ser Ala Val
1               5

<210> SEQ ID NO 131
<211> LENGTH: 7
<212> TYPE: PRT
<213> ORGANISM: Artificial Sequence
<220> FEATURE:
<223> OTHER INFORMATION: NRC-sdAb002 CDR2-A

<400> SEQUENCE: 131

Ile Thr Asn Ser Gly Asn Ile
1               5

<210> SEQ ID NO 132
<211> LENGTH: 21
<212> TYPE: PRT
<213> ORGANISM: Artificial Sequence
<220> FEATURE:
<223> OTHER INFORMATION: NRC-sdAb002 CDR3-A

```
<400> SEQUENCE: 132

Ala Ala Lys Trp Ser Phe Ser Ser Gly Tyr Gly Asp Leu Arg Arg Ala
1               5                   10                  15
Ala Met Tyr Asp Tyr
            20

<210> SEQ ID NO 133
<211> LENGTH: 8
<212> TYPE: PRT
<213> ORGANISM: Artificial Sequence
<220> FEATURE:
<223> OTHER INFORMATION: NRC-sdAb003 CDR1-A

<400> SEQUENCE: 133

Gly Val Thr Leu Asp Tyr Thr Ala
1               5

<210> SEQ ID NO 134
<211> LENGTH: 7
<212> TYPE: PRT
<213> ORGANISM: Artificial Sequence
<220> FEATURE:
<223> OTHER INFORMATION: NRC-sdAb003 CDR2-A

<400> SEQUENCE: 134

Ile Thr Ser Gly Gly Asn Thr
1               5

<210> SEQ ID NO 135
<211> LENGTH: 13
<212> TYPE: PRT
<213> ORGANISM: Artificial Sequence
<220> FEATURE:
<223> OTHER INFORMATION: NRC-sdAb003 CDR3-A

<400> SEQUENCE: 135

Ala Ala Arg Arg Gly Gly Ala Arg Gly Glu Tyr Asp Tyr
1               5                   10

<210> SEQ ID NO 136
<211> LENGTH: 8
<212> TYPE: PRT
<213> ORGANISM: Artificial Sequence
<220> FEATURE:
<223> OTHER INFORMATION: NRC-sdAb004 CDR1-A

<400> SEQUENCE: 136

Arg Gly Ala Phe Asp Thr Tyr Glu
1               5

<210> SEQ ID NO 137
<211> LENGTH: 8
<212> TYPE: PRT
<213> ORGANISM: Artificial Sequence
<220> FEATURE:
<223> OTHER INFORMATION: NRC-sdAb004 CDR2-A

<400> SEQUENCE: 137

Val Thr Arg Asn Gly Asp Ser Val
1               5

<210> SEQ ID NO 138
<211> LENGTH: 18
<212> TYPE: PRT
<213> ORGANISM: Artificial Sequence
```

<220> FEATURE:
<223> OTHER INFORMATION: NRC-sdAb004 CDR3-A

<400> SEQUENCE: 138

Ala Ala Asn Trp Arg Pro Leu Arg Thr Ser Ser Gly Ala Asp Asp Tyr
1               5                   10                  15
Ala Asp

<210> SEQ ID NO 139
<211> LENGTH: 8
<212> TYPE: PRT
<213> ORGANISM: Artificial Sequence
<220> FEATURE:
<223> OTHER INFORMATION: NRC-sdAb005 CDR1-A

<400> SEQUENCE: 139

Gly Ser Ile Ser Ser Ile Asn Thr
1               5

<210> SEQ ID NO 140
<211> LENGTH: 7
<212> TYPE: PRT
<213> ORGANISM: Artificial Sequence
<220> FEATURE:
<223> OTHER INFORMATION: NRC-sdAb005 CDR2-A

<400> SEQUENCE: 140

Ser Asp Ser Gly Ala Asn Arg
1               5

<210> SEQ ID NO 141
<211> LENGTH: 12
<212> TYPE: PRT
<213> ORGANISM: Artificial Sequence
<220> FEATURE:
<223> OTHER INFORMATION: NRC-sdAb005 CDR3-A

<400> SEQUENCE: 141

Arg Ala Trp Gly Thr Gly Thr Ile Ser Thr Met Tyr
1               5                   10

<210> SEQ ID NO 142
<211> LENGTH: 8
<212> TYPE: PRT
<213> ORGANISM: Artificial Sequence
<220> FEATURE:
<223> OTHER INFORMATION: NRC-sdAb006 CDR1-A

<400> SEQUENCE: 142

Glu Ser Ile Phe Gly Phe Asn Thr
1               5

<210> SEQ ID NO 143
<211> LENGTH: 7
<212> TYPE: PRT
<213> ORGANISM: Artificial Sequence
<220> FEATURE:
<223> OTHER INFORMATION: NRC-sdAb006 CDR2-A

<400> SEQUENCE: 143

Ile Ser Asn Ser Lys Arg Thr
1               5

-continued

<210> SEQ ID NO 144
<211> LENGTH: 12
<212> TYPE: PRT
<213> ORGANISM: Artificial Sequence
<220> FEATURE:
<223> OTHER INFORMATION: NRC-sdAb006 CDR3-A

<400> SEQUENCE: 144

Arg Ala Trp Gly Ile Ile Thr Ser Ala Thr Val Tyr
1               5                   10

<210> SEQ ID NO 145
<211> LENGTH: 8
<212> TYPE: PRT
<213> ORGANISM: Artificial Sequence
<220> FEATURE:
<223> OTHER INFORMATION: NRC-sdAb007 CDR1-A

<400> SEQUENCE: 145

Thr Arg Thr Val Ser Ser Ala Val
1               5

<210> SEQ ID NO 146
<211> LENGTH: 7
<212> TYPE: PRT
<213> ORGANISM: Artificial Sequence
<220> FEATURE:
<223> OTHER INFORMATION: NRC-sdAb007 CDR2-A

<400> SEQUENCE: 146

Ile Ser Asn Ser Gly Ser Val
1               5

<210> SEQ ID NO 147
<211> LENGTH: 15
<212> TYPE: PRT
<213> ORGANISM: Artificial Sequence
<220> FEATURE:
<223> OTHER INFORMATION: NRC-sdAb007 CDR3-A

<400> SEQUENCE: 147

Ala Ile Ile Trp Arg Thr Ser Asp Leu Thr Gly Arg Phe Asn Thr
1               5                   10                  15

<210> SEQ ID NO 148
<211> LENGTH: 8
<212> TYPE: PRT
<213> ORGANISM: Artificial Sequence
<220> FEATURE:
<223> OTHER INFORMATION: NRC-sdAb008 CDR1-A

<400> SEQUENCE: 148

Gly Ser Ser Gly Met Ile Asn Thr
1               5

<210> SEQ ID NO 149
<211> LENGTH: 7
<212> TYPE: PRT
<213> ORGANISM: Artificial Sequence
<220> FEATURE:
<223> OTHER INFORMATION: NRC-sdAb008 CDR2-A

<400> SEQUENCE: 149

Arg Ser Thr Gly Gly Thr Thr
1               5

```
<210> SEQ ID NO 150
<211> LENGTH: 15
<212> TYPE: PRT
<213> ORGANISM: Artificial Sequence
<220> FEATURE:
<223> OTHER INFORMATION: NRC-sdAb008 CDR3-A

<400> SEQUENCE: 150

Ala Ile Ile Trp Arg Thr Ser Asp Leu Thr Gly Arg Phe Asn Thr
1               5                   10                  15

<210> SEQ ID NO 151
<211> LENGTH: 5
<212> TYPE: PRT
<213> ORGANISM: Artificial Sequence
<220> FEATURE:
<223> OTHER INFORMATION: F155-3C7 CDR H1-B

<400> SEQUENCE: 151

Asn Phe Trp Ile Asn
1               5

<210> SEQ ID NO 152
<211> LENGTH: 17
<212> TYPE: PRT
<213> ORGANISM: Artificial Sequence
<220> FEATURE:
<223> OTHER INFORMATION: F155-3C7 CDR H2-B

<400> SEQUENCE: 152

Asn Ile Phe Pro Gly Ser Asn Ser Ser Asn Tyr Asn Glu Lys Phe Lys
1               5                   10                  15

Asn

<210> SEQ ID NO 153
<211> LENGTH: 9
<212> TYPE: PRT
<213> ORGANISM: Artificial Sequence
<220> FEATURE:
<223> OTHER INFORMATION: F155-3C7 CDR H3-B

<400> SEQUENCE: 153

Asp Tyr Tyr Gly Gly Ser Pro Asp Tyr
1               5

<210> SEQ ID NO 154
<211> LENGTH: 17
<212> TYPE: PRT
<213> ORGANISM: Artificial Sequence
<220> FEATURE:
<223> OTHER INFORMATION: F155-3C7 CDR L1-B

<400> SEQUENCE: 154

Lys Ser Ser Gln Ser Leu Leu Asn Ser Lys Thr Arg Lys Asn Tyr Leu
1               5                   10                  15

Ala

<210> SEQ ID NO 155
<211> LENGTH: 7
<212> TYPE: PRT
<213> ORGANISM: Artificial Sequence
<220> FEATURE:
<223> OTHER INFORMATION: F155-3C7 CDR L2-B
```

```
<400> SEQUENCE: 155

Trp Ala Ser Thr Arg Glu Ser
1               5

<210> SEQ ID NO 156
<211> LENGTH: 8
<212> TYPE: PRT
<213> ORGANISM: Artificial Sequence
<220> FEATURE:
<223> OTHER INFORMATION: F155-3C7 CDR L3-B

<400> SEQUENCE: 156

Lys His Ser Tyr Asn Leu Trp Thr
1               5

<210> SEQ ID NO 157
<211> LENGTH: 5
<212> TYPE: PRT
<213> ORGANISM: Artificial Sequence
<220> FEATURE:
<223> OTHER INFORMATION: F149-4G4 CDR H1-B

<400> SEQUENCE: 157

Tyr Tyr Gly Ile Asn
1               5

<210> SEQ ID NO 158
<211> LENGTH: 17
<212> TYPE: PRT
<213> ORGANISM: Artificial Sequence
<220> FEATURE:
<223> OTHER INFORMATION: F149-4G4 CDR H2-B

<400> SEQUENCE: 158

Trp Ile Asn Thr Tyr Leu Gly Glu Pro Thr Tyr Ala Asp Asp Phe Lys
1               5                   10                  15

Gly

<210> SEQ ID NO 159
<211> LENGTH: 9
<212> TYPE: PRT
<213> ORGANISM: Artificial Sequence
<220> FEATURE:
<223> OTHER INFORMATION: F149-4G4 CDR H3-B

<400> SEQUENCE: 159

Gly Thr Met Ser Tyr Ser Phe Asp Tyr
1               5

<210> SEQ ID NO 160
<211> LENGTH: 12
<212> TYPE: PRT
<213> ORGANISM: Artificial Sequence
<220> FEATURE:
<223> OTHER INFORMATION: F149-4G4 CDR L1-B

<400> SEQUENCE: 160

Arg Ala Ser Ser Ser Val Ser Ser Ser Tyr Leu His
1               5                   10

<210> SEQ ID NO 161
<211> LENGTH: 7
<212> TYPE: PRT
<213> ORGANISM: Artificial Sequence
<220> FEATURE:
<223> OTHER INFORMATION: F149-4G4 CDR L2-B
```

-continued

```
<400> SEQUENCE: 161

Ser Thr Ser Lys Leu Ala Ser
1               5

<210> SEQ ID NO 162
<211> LENGTH: 9
<212> TYPE: PRT
<213> ORGANISM: Artificial Sequence
<220> FEATURE:
<223> OTHER INFORMATION: F149-4G4 CDR L3-B

<400> SEQUENCE: 162

His Gln Tyr Ser Gly Asp Pro Leu Thr
1               5

<210> SEQ ID NO 163
<211> LENGTH: 5
<212> TYPE: PRT
<213> ORGANISM: Artificial Sequence
<220> FEATURE:
<223> OTHER INFORMATION: NRC-sdAb001 CDR1-B

<400> SEQUENCE: 163

Phe Asp Ile Met Gly
1               5

<210> SEQ ID NO 164
<211> LENGTH: 16
<212> TYPE: PRT
<213> ORGANISM: Artificial Sequence
<220> FEATURE:
<223> OTHER INFORMATION: NRC-sdAb001 CDR2-B

<400> SEQUENCE: 164

Ala Ile Thr Thr Leu Asp Ile Ala Asn Tyr Arg Asp Ser Val Lys Gly
1               5                   10                  15

<210> SEQ ID NO 165
<211> LENGTH: 7
<212> TYPE: PRT
<213> ORGANISM: Artificial Sequence
<220> FEATURE:
<223> OTHER INFORMATION: NRC-sdAb001 CDR3-B

<400> SEQUENCE: 165

Phe Gln Ser Asp Gln Asn Tyr
1               5

<210> SEQ ID NO 166
<211> LENGTH: 5
<212> TYPE: PRT
<213> ORGANISM: Artificial Sequence
<220> FEATURE:
<223> OTHER INFORMATION: NRC-sdAb002 CDR1-B

<400> SEQUENCE: 166

Ser Ala Val Met Ala
1               5

<210> SEQ ID NO 167
<211> LENGTH: 16
<212> TYPE: PRT
<213> ORGANISM: Artificial Sequence
<220> FEATURE:
<223> OTHER INFORMATION: NRC-sdAb002 CDR2-B
```

```
<400> SEQUENCE: 167

Phe Ile Thr Asn Ser Gly Asn Ile Leu Tyr Asp Asp Ser Val Lys Gly
1               5                   10                  15

<210> SEQ ID NO 168
<211> LENGTH: 19
<212> TYPE: PRT
<213> ORGANISM: Artificial Sequence
<220> FEATURE:
<223> OTHER INFORMATION: NRC-sdAb002 CDR3-B

<400> SEQUENCE: 168

Lys Trp Ser Phe Ser Ser Gly Tyr Gly Asp Leu Arg Arg Ala Ala Met
1               5                   10                  15

Tyr Asp Tyr

<210> SEQ ID NO 169
<211> LENGTH: 5
<212> TYPE: PRT
<213> ORGANISM: Artificial Sequence
<220> FEATURE:
<223> OTHER INFORMATION: NRC-sdAb003 CDR1-B

<400> SEQUENCE: 169

Tyr Thr Ala Ile Gly
1               5

<210> SEQ ID NO 170
<211> LENGTH: 16
<212> TYPE: PRT
<213> ORGANISM: Artificial Sequence
<220> FEATURE:
<223> OTHER INFORMATION: NRC-sdAb003 CDR2-B

<400> SEQUENCE: 170

Ala Ile Thr Ser Gly Gly Asn Thr Asp Tyr Ala Glu Ser Ala Lys Gly
1               5                   10                  15

<210> SEQ ID NO 171
<211> LENGTH: 11
<212> TYPE: PRT
<213> ORGANISM: Artificial Sequence
<220> FEATURE:
<223> OTHER INFORMATION: NRC-sdAb003 CDR3-B

<400> SEQUENCE: 171

Arg Arg Gly Gly Ala Arg Gly Glu Tyr Asp Tyr
1               5                   10

<210> SEQ ID NO 172
<211> LENGTH: 5
<212> TYPE: PRT
<213> ORGANISM: Artificial Sequence
<220> FEATURE:
<223> OTHER INFORMATION: NRC-sdAb004 CDR1-B

<400> SEQUENCE: 172

Thr Tyr Glu Ile Gly
1               5

<210> SEQ ID NO 173
<211> LENGTH: 17
<212> TYPE: PRT
<213> ORGANISM: Artificial Sequence
<220> FEATURE:
<223> OTHER INFORMATION: NRC-sdAb004 CDR2-B
```

```
<400> SEQUENCE: 173

Ala Val Thr Arg Asn Gly Asp Ser Val Val Tyr Ala Asp Ser Leu Lys
1               5                   10                  15
Ala

<210> SEQ ID NO 174
<211> LENGTH: 16
<212> TYPE: PRT
<213> ORGANISM: Artificial Sequence
<220> FEATURE:
<223> OTHER INFORMATION: NRC-sdAb004 CDR3-B

<400> SEQUENCE: 174

Asn Trp Arg Pro Leu Arg Thr Ser Ser Gly Ala Asp Tyr Ala Asp
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: NRC-sdAb005 CDR1-B

<400> SEQUENCE: 175

Ala Ser Asp Ser Gly Ala Asn Arg Asn Tyr Ala Asp Ser Val Lys Gly
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: NRC-sdAb005 CDR2-B

<400> SEQUENCE: 176

Ala Ser Asp Ser Gly Ala Asn Arg Asn Tyr Ala Asp Ser Val Lys Gly
1               5                   10                  15

<210> SEQ ID NO 177
<211> LENGTH: 10
<212> TYPE: PRT
<213> ORGANISM: Artificial Sequence
<220> FEATURE:
<223> OTHER INFORMATION: NRC-sdAb005 CDR3-B

<400> SEQUENCE: 177

Trp Gly Thr Gly Thr Ile Ser Thr Met Tyr
1               5                   10

<210> SEQ ID NO 178
<211> LENGTH: 5
<212> TYPE: PRT
<213> ORGANISM: Artificial Sequence
<220> FEATURE:
<223> OTHER INFORMATION: NRC-sdAb006 CDR1-B

<400> SEQUENCE: 178

Phe Asn Thr Met Gly
1               5

<210> SEQ ID NO 179
<211> LENGTH: 16
<212> TYPE: PRT
<213> ORGANISM: Artificial Sequence
<220> FEATURE:
<223> OTHER INFORMATION: NRC-sdAb006 CDR2-B
```

```
<400> SEQUENCE: 179

Ser Ile Ser Asn Ser Lys Arg Thr Met Tyr Ala Asp Ser Val Lys Gly
1               5                   10                  15

<210> SEQ ID NO 180
<211> LENGTH: 10
<212> TYPE: PRT
<213> ORGANISM: Artificial Sequence
<220> FEATURE:
<223> OTHER INFORMATION: NRC-sdAb006 CDR3-B

<400> SEQUENCE: 180

Trp Gly Ile Ile Thr Ser Ala Thr Val Tyr
1               5                   10

<210> SEQ ID NO 181
<211> LENGTH: 5
<212> TYPE: PRT
<213> ORGANISM: Artificial Sequence
<220> FEATURE:
<223> OTHER INFORMATION: NRC-sdAb007 CDR1-B

<400> SEQUENCE: 181

Ser Ala Val Met Ala
1               5

<210> SEQ ID NO 182
<211> LENGTH: 16
<212> TYPE: PRT
<213> ORGANISM: Artificial Sequence
<220> FEATURE:
<223> OTHER INFORMATION: NRC-sdAb007 CDR2-B

<400> SEQUENCE: 182

Phe Ile Ser Asn Ser Gly Ser Val Tyr Tyr Asp Asp Ser Val Lys Gly
1               5                   10                  15

<210> SEQ ID NO 183
<211> LENGTH: 13
<212> TYPE: PRT
<213> ORGANISM: Artificial Sequence
<220> FEATURE:
<223> OTHER INFORMATION: NRC-sdAb007 CDR3-B

<400> SEQUENCE: 183

Ile Trp Arg Thr Ser Asp Leu Thr Gly Arg Phe Asn Thr
1               5                   10

<210> SEQ ID NO 184
<211> LENGTH: 5
<212> TYPE: PRT
<213> ORGANISM: Artificial Sequence
<220> FEATURE:
<223> OTHER INFORMATION: NRC-sdAb008 CDR1-B

<400> SEQUENCE: 184

Ile Asn Thr Met Gly
1               5

<210> SEQ ID NO 185
<211> LENGTH: 16
<212> TYPE: PRT
<213> ORGANISM: Artificial Sequence
<220> FEATURE:
<223> OTHER INFORMATION: NRC-sdAb008 CDR2-B
```

```
<400> SEQUENCE: 185

Arg Arg Ser Thr Gly Gly Thr Thr Asn Tyr Ala Asp Ser Val Lys Gly
1               5                   10                  15

<210> SEQ ID NO 186
<211> LENGTH: 13
<212> TYPE: PRT
<213> ORGANISM: Artificial Sequence
<220> FEATURE:
<223> OTHER INFORMATION: NRC-sdAb008 CDR3-B

<400> SEQUENCE: 186

Ile Trp Arg Thr Ser Asp Leu Thr Gly Arg Phe Asn Thr
1               5                   10

<210> SEQ ID NO 187
<211> LENGTH: 17
<212> TYPE: PRT
<213> ORGANISM: Artificial Sequence
<220> FEATURE:
<223> OTHER INFORMATION: Fc peptide

<400> SEQUENCE: 187

Thr Thr Pro Pro Val Leu Asp Ser Asp Gly Ser Phe Phe Leu Tyr Ser
1               5                   10                  15

Lys

<210> SEQ ID NO 188
<211> LENGTH: 11
<212> TYPE: PRT
<213> ORGANISM: Artificial Sequence
<220> FEATURE:
<223> OTHER INFORMATION: A20.1 peptide

<400> SEQUENCE: 188

Glu Phe Val Ala Ala Gly Ser Ser Thr Gly Arg
1               5                   10
```

AXL-SPECIFIC ANTIBODIES AND USES THEREOF

CROSS REFERENCE TO RELATED APPLICATIONS

This application claims the benefit of priority of U.S. Provisional Patent Application No. 62/557,870 filed Sep. 13, 2017, which is hereby incorporated by reference.

FIELD

The present disclosure relates to AXL-specific antibodies and uses thereof. Such antibodies bind to cell surface expressed human AXL and may be used in fusions or in antibody-drug conjugates.

BACKGROUND

AXL is a member of the Tyro3-AXL-Mer (TAM) receptor tyrosine kinase subfamily. A schematic of AXL domain structure is shown in the Prior Art illustration of FIG. 1. The extracellular domain of the AXL protein (100) is shown with exons (1 to 20) indicated. The AXL protein (100) comprises 2 immunoglobulin-like domains (102) and 2 fibronectin type III (FNIII) repeats (104). A transmembrane domain (106) spans the cell membrane, followed by the intracellular kinase domain (108). Splicing (indicated at 110) yields a slightly shorter transcript.

Following binding of the AXL extracellular domain to Growth arrest-specific 6 (Gash), a vitamin K-dependent protein, AXL is capable of transducing signals involved in several cellular functions including growth, migration, aggregation, and anti-inflammation in multiple cell types (Holland et al., 2005; Li et al., 2009). AXL was originally identified as an oncogene in chronic myelogenous leukemia (O'Bryan et al., 1991). Subsequently, expression of AXL has been reported to be upregulated in a variety of cancers including breast, gastric, prostate, ovarian, and lung (Linger et al., 2008; Paccez et al., 2014).

AXL has also been implicated in epithelial-to-mesenchymal transition (Gjerdrum et al., 2010), a process closely linked with invasive motility and metastasis of malignant cells. Moreover, AXL expression has been shown to be negatively associated with patient survival (Linger et al., 2008; Gjerdrum et al., 2010). Several recent studies have reported that AXL is overexpressed and activated in several drug-resistant cancer cell lines (Asiedu et al., 2014; Meyer et al., 2013; Thomson et al., 2011), suggesting that AXL may play a role in resistance to chemotherapy and other molecularly targeted therapies. AXL expression has also recently been shown to be increased during hypoxia (Rankin et al., 2014), a condition that frequently occurs as solid tumors become larger and more aggressive. Taken together, these data suggest AXL as a promising diagnostic, prognostic, and therapeutic target for cancer.

Recent studies using gene knock-out or RNAi validate the therapeutic value of AXL inhibition in cell line and mouse models. In addition, several small molecule AXL inhibitors have been developed and marketed including: BOSU-TINIB™, a protein-tyrosine kinase inhibitor sold by Pfizer Inc. under the name BOSULIF™, also known as SKI-606, bearing Pfizer Inc. product number PF-5208763 (Lee et al., 2014); CABOZANTINIB™, a small molecule inhibitor of the tyrosine kinases c-Met and VEGFR2 sold by Exelixis under the name COMETRIQ™, product number XL184 (Yakes et al., 2011); and SUNITINIB™, sold by Pfizer Inc. under the name SUTENT™, product number SU11248 (Kitagawa et al., 2013). These drugs target multiple kinases, and inhibit AXL activity less effectively than their primary kinase targets (Feneyrolles et al., 2014).

Other small molecule drugs are in earlier phases of clinical and preclinical development, including BGB324™ (formerly known as R428) of BergenBio (Bergen, Norway) and Rigel Pharmaceuticals (San Francisco, Calif., USA), currently one of the most potent and selective inhibitors of AXL. It was shown to have an IC50 of 14 nM and to be considerably more selective for AXL than other kinases tested (Holland et al., 2010); however, it still shows activity for Tie-2, Flt-4, Flt-1, Ret, Abl as well as for the other members of the TAM family, Tyro-3 and Mer. It blocks AXL's ability to promote angiogenesis and metastasis in preclinical breast animal models (Holland et al., 2010) and entered clinical phase I in 2013 for treatment of aggressive and metastatic cancers. Development of small molecule AXL inhibitors has been challenging in the absence of a three-dimensional structure of the AXL kinase domain, and the potential for off-target toxicities remains a major concern.

To circumvent some of the drawbacks of small molecules, anti-AXL antibodies may be considered. Li et al. (2009) developed a monoclonal antibody (12A11) against AXL that did not interfere with Gas6 binding, inhibited AXL activation, induced AXL downregulation, and reduced growth of tumor xenografts in a subcutaneous non-small cell lung cancer (NSCLC) model. Subsequently, Ye et al. (2010) developed a monoclonal antibody (YW327.652) that recognizes the extracellular domain of both human and murine AXL and blocks Gas6 binding. This antibody has been shown to diminish xenograft tumor growth in NSCLC models as well as orthotopic metastasis models of breast cancer. Additionally, treatment with YW327.6S2 enhanced the effects of erlotinib and chemotherapy in reducing NSCLC tumor growth as well as potentiated anti-VEGF treatment in breast cancer and NSCLC mouse xenograft models. Leconet et al. (2014) describe anti-AXL monoclonal antibodies that do not interfere with Gas6 binding, inhibit AXL activation, and induced its downregulation from the cell surface. The subject antibodies reduced growth of both subcutaneous and orthotopic pancreatic tumor xenografts in vivo.

One drawback of therapeutic antibodies that reduce the activity of AXL is that they are likely to encounter therapeutic resistance, of either an innate nature due to intrinsic lack of sensitivity, or of an acquired nature due to bypass mechanisms that arise during selective pressure of treatment. Therefore, there is a need for AXL inhibitors that are active and specific with fewer off-target effects, and with reduced or acceptable toxicity and therapeutic resistance.

Antibody-drug conjugates are highly complex entities that combine an antibody, typically via a linker, with a drug. An antibody-drug conjugate in development by Genmab A/S (Copenhagen, Denmark) and Seattle Genetics (Washington, USA), HUMAX-AXL-ADC™, comprises an AXL-specific monoclonal antibody that does not compete with Gas6 binding conjugated to monomethyl auristatin E (MMAE). HUMAX-AXL-ADC™ potently induced tumor regression in NSCLC xenograft models after a single dose of 1 mg/kg, and had similar effects in patient-derived xenograft models in which AXL expression was heterogeneous. Antibodies binding to AXL, which do not compete with Gas6 binding are described in International Patent Publication WO2016/005593 A1 (Breij et al.).

An antibody-drug conjugate (ADC) approach, in which an anti-AXL antibody is used to deliver a potent cytotoxic drug, increases the patient population that is likely to respond to the drug. An ADC may be of use even in the event of acquired resistance to antibodies.

There is a need for AXL-specific antibodies for use in disease detection, staging and/or therapy.

SUMMARY

It is an object of the present disclosure to provide AXL-specific antibodies. AXL-specific monoclonal and single domain antibodies and antigen-binding fragments also referred to as antibodies are described, as well as uses therefor. Such AXL-specific antibodies bind to cell surface-expressed human AXL. Antibody-drug conjugates and fusions are described.

The present disclosure provides an isolated or purified antibody that specifically binds to an epitope in an immunoglobulin-like (IgL) domain of human AXL ectodomain (ECD).

There is also provided an antibody or fragment thereof comprising variable light chain (VL) CDR1, CDR2, and CDR3 sequences selected from the group consisting of: SEQ ID NO:98-100; SEQ ID NO:92-94; SEQ ID NO:110-112; SEQ ID NO:86-88; SEQ ID NO:80-82; SEQ ID NO:104-106; SEQ ID NO:116-118; and sequences substantially identical thereto.

There is provided herein an antibody or fragment thereof comprising a variable light chain (VL) sequence selected from the group consisting of: SEQ ID NO:38; SEQ ID NO:40; SEQ ID NO:42; SEQ ID NO:44; SEQ ID NO:46; SEQ ID NO:74; SEQ ID NO:76; and sequences substantially identical thereto.

Further, there is provided an antibody or fragment thereof comprising variable heavy chain (VH) CDR1, CDR2, and CDR3 sequences selected from the group consisting of: SEQ ID NO:95-97; SEQ ID NO:89-91; SEQ ID NO:107-09; SEQ ID NO:83-85; SEQ ID NO:77-79; SEQ ID NO:101-103; SEQ ID NO:113-115; and sequences substantially identical thereto.

There is provided herein an antibody or fragment thereof comprising a variable heavy chain (VH) sequence selected from the group consisting of: SEQ ID NO:39; SEQ ID NO:41; SEQ ID NO:43; SEQ ID NO:45; SEQ ID NO:47; SEQ ID NO:73; SEQ ID NO:75; and sequences substantially identical thereto.

Further, there is provided an antibody or fragment thereof comprising a single domain (sd) heavy chain variable (VHH) domain sequence selected from the group consisting of: SEQ ID NOs:119-126; and sequences substantially identical thereto.

There is also provided an antibody or fragment thereof selected from the group consisting of: VH of SEQ ID NO:39, and VL of SEQ ID NO:38; VH of SEQ ID NO:41, and VL of SEQ ID NO:40; VH of SEQ ID NO:43, and VL of SEQ ID NO:42; VH of SEQ ID NO:45, and VL of SEQ ID NO:44; VH of SEQ ID NO:47, and VL of SEQ ID NO:46; VH of SEQ ID NO:73, and VL of SEQ ID NO:74; VH of SEQ ID NO:75, and VL of SEQ ID NO:76; VHH of SEQ ID NO:119; VHH of SEQ ID NO:120; VHH of SEQ ID NO:121; VHH of SEQ ID NO:122; VHH of SEQ ID NO:123; VHH of SEQ ID NO:124; VHH of SEQ ID NO:125; VHH of SEQ ID NO:126; and sequences having 85% or greater identity thereto.

Antibody drug conjugates (ADCs), pharmaceutical compositions, and fusion proteins are described, comprising the described antibodies. Nucleic acid molecules encoding the described antibodies, and vectors or host cells comprising same are also provided.

Methods of in vitro and in vivo detecting of AXL are described. Methods of transporting molecules of interest into cells expressing AXL are described. Methods and uses of the described antibodies for treating cancer, employing antibody drug conjugates are provided.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 7 shows amino acid sequences of the mAb $V_H/V_L$ domains with CDRs using IMGT definitions, shown in bold underlined font.

FIG. 8 shows amino acid sequences of the VHHs with CDRs, using IMGT definitions, represented in bold underlined font.

DETAILED DESCRIPTION

Figure 1:
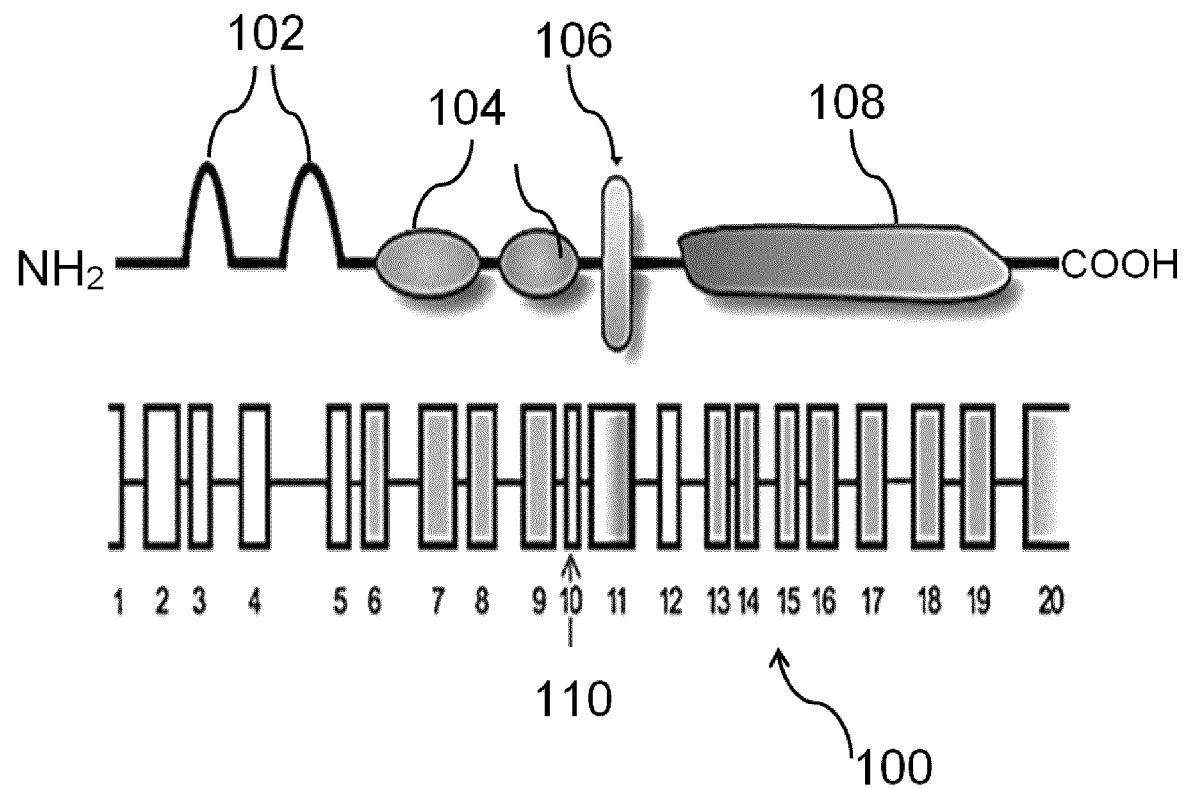
FIG. 1 (Prior Art) is a schematic depiction of AXL domain structure.

Generally, the present disclosure provides anti-AXL monoclonal and single domain antibodies for use in treatment, identification/diagnosis, and staging/prognosis of diseases, such as cancer.

An isolated or purified antibody is described, which specifically binds to an epitope in an immunoglobulin-like (IgL) domain of human AXL ectodomain (ECD). The AXL ECD may, for example, have the amino acid sequence of SEQ ID NO:71. The epitope of the antibody may be located in IgL1 or IgL2 of AXL. The antibody may be capable of internalization into AXL expressing tumor cells.

The antibody can be a single domain antibody, a monoclonal antibody, a humanized antibody, a chimeric antibody, a biparatopic antibody, a bispecific antibody, or may be an AXL-binding antibody fragment thereof. If the antibody is a chimeric antibody, it may comprise framework regions from human IgG1, and may comprise framework regions from human kappa light chain and human IgG heavy chain. The antibody may comprise framework regions from IgA, IgD, IgE, IgG, or IgM.

The antibody may be a full-length IgG, Fv, scFv, Fab, or F(ab')2, VHH, VL, or VH. The antibody may have an equilibrium dissociation constant (KD) of <50 nM to human AXL ectodomain. Optionally, the binding to the epitope in an IgL domain of AXL ECD may be one that does not compete with the binding of Growth arrest-specific 6 (Gash) ligand to AXL.

The antibody or fragment may have variable light chain (VL) CDR1, CDR2, and CDR3 sequences selected from the group consisting of: SEQ ID NO:98, 99, and 100; SEQ ID NO:92, 93 and 94; SEQ ID NO:110, 111, and 112; SEQ ID NO:86, 87, and 88; SEQ ID NO:80, 81, and 82; SEQ ID NO:104, 105, and 106; SEQ ID NO:116, 117, and 118; and sequences substantially identical thereto.

The antibody or fragment thereof may be one comprising a variable light chain (VL) sequence selected from the group consisting of: SEQ ID NO:38; 40; 42; 44; 46; 74; 76; and sequences substantially identical thereto. The antibody or fragment may comprise variable heavy chain (VH) CDR1, CDR2, and CDR3 sequences selected from the group consisting of: SEQ ID NO:95-97; 89-91; 107-109; 83-85; 77-79; 101-103; 113-115; and sequences substantially identical thereto.

An antibody or fragment thereof is described, which comprises a variable heavy chain (VH) sequence selected from the group consisting of: SEQ ID NO:39; 41; 43; 45; 47; 73; 75; and sequences substantially identical thereto.

The antibody or fragment thereof may be one comprising variable heavy chain (VL) CDR1, CDR2, and CDR3 sequences; and (VH) CDR1, CDR2, and CDR3 sequences selected from the group consisting of: VL, SEQ ID NO:98-100 and VH, SEQ ID NO:95-97; VL, SEQ ID NO:92-94 and VH, SEQ ID NO:89-91; VL, SEQ ID NO:110-112 and VH, SEQ ID NO:107-109; VL, SEQ ID NO:86-88 and VH, SEQ ID NO:83-85; VL, SEQ ID NO:80-82 and VH, SEQ ID NO:77-79; VL, SEQ ID NO:104-106 and VH, SEQ ID NO:101-103; VL, SEQ ID NO:116-118 and VH, SEQ ID NO:113-115; and sequences substantially identical thereto.

The antibody described may comprise single domain (sd) heavy chain variable (VHH) domain CDR1, CDR2, and CDR3 sequences selected from the group consisting of: SEQ ID NO:127-129; SEQ ID NO:130-132; SEQ ID NO:133-135; SEQ ID NO:136-138; SEQ ID NO:139-141; SEQ ID NO:142-144; SEQ ID NO:145-147; SEQ ID NO:148-150; and sequences substantially identical thereto.

An antibody or fragment thereof is described which has a single domain (sd) heavy chain variable (VHH) domain sequence selected from the group consisting of any one of: SEQ ID NOs:119 to 126; and sequences substantially identical thereto.

An antibody or fragment thereof is described, which is selected from the group consisting of: VH of SEQ ID NO:39, and VL of SEQ ID NO:38; VH of SEQ ID NO:41, and VL of SEQ ID NO:40; VH of SEQ ID NO:43, and VL of SEQ ID NO:42; VH of SEQ ID NO:45, and VL of SEQ ID NO:44; VH of SEQ ID NO:47, and VL of SEQ ID NO:46; VH of SEQ ID NO:73, and VL of SEQ ID NO:74; VH of SEQ ID NO:75, and VL of SEQ ID NO:76; and the VHH sequences from 119-126, as well as sequences having 85% or greater identity thereto.

For example, the antibody or fragment thereof may have a sequence identity of >90%, >95%, or >98% as compared with specifically exemplified sequences listed herein.

The described antibody may comprise light chain CDR1, CDR2 and CDR3 sequences of SEQ ID NO:1, 2, and 11; and heavy chain CDR1, CDR2 and CDR3 sequence of SEQ ID NO:3, 4, and 5; wherein the antibody binds an epitope in the IgL1 domain and not in the IgL2 domain of AXL. The antibody may comprise light chain CDR1, CDR2 and CDR3 sequences of SEQ ID NO:1, 6, and 11; and heavy chain CDR1, CDR2 and CDR3 sequence of SEQ ID NO:7, 8, and 5; wherein the antibody binds an epitope in the IgL1 domain and not in the IgL2 domain of AXL.

The antibody may comprise light chain CDR1, CDR2 and CDR3 sequences of SEQ ID NO:9, 10, and 11; and heavy chain CDR1, CDR2 and CDR3 sequence of SEQ ID NO:12, 13, and 14.

Alternatively, the antibody may comprise light chain CDR1, CDR2 and CDR3 sequences of SEQ ID NO:15, 16, and 11; and heavy chain CDR1, CDR2 and CDR3 sequence of SEQ ID NO:17, 18, and 19.

The antibody may be one which does not compete with Gas6 for AXL binding.

The antibody may be one that is biparatopic. Such a biparatopic antibody may be, for example: sdAb001/005 or sdAb001/006.

An antibody drug conjugate (ADC) is described which comprises the antibody described herein, which is conjugated to a drug moiety. The drug moiety may be, for example, an anti-cancer drug. An exemplary drug moiety is DM1.

A pharmaceutical composition is described comprising an ADC and a pharmaceutically acceptable excipient.

A fusion protein is described, comprising the antibody described herein and human IgG1 Fc.

A nucleic acid molecule is described, which encodes the antibody. A vector comprising a nucleic acid molecule is described. The viral vector may be adenoviral, lentiviral or retroviral.

A host cell is described, which may comprise the vector noted above. The host cell may be a recombinant microbial host cell or may be a mammalian cell, and said cell may produce the antibody described herein.

A hybridoma or an organism that produces the antibody is also provided.

In some instances, the antibody may be immobilized onto a surface. Further, the antibody may be linked to a cargo molecule. Optionally, the cargo molecule may be a detectable agent, a therapeutic agent, a drug, a peptide, an enzyme, a growth factor, a cytokine, a receptor trap, an antibody thereof, a chemical compound, a carbohydrate moiety, a DNA-based molecule, a cytotoxic agent, or a viral vector.

When the antibody has a cargo molecule, an exemplary size of the cargo molecule may be from about 1 to about 500 kDa. The cargo molecule can be loaded in a liposome or nanocarrier. Such a nanocarrier may comprise one or more nanoparticle, nanowire, nanotube, or quantum dots. The cargo molecule may be a cytotoxic agent.

The DNA-based molecule may comprise an anti-sense oligonucleotide, microRNA, siRNA, or a plasmid.

An in vitro method of detecting AXL is described, comprising: a) contacting a sample with one, or more than one, isolated or purified antibody linked to a detectable agent; and b) detecting the detectable agent linked to the antibody thereof bound to AXL in the sample.

A method is described for detecting AXL in circulating cells where the sample may be a serum sample.

The step of detecting, in such a method, may be performed using optical imaging, immunohistochemistry, molecular diagnostic imaging, or ELISA.

There is described herein an in vivo method of detecting AXL expression in a subject, comprising: a) administering to the subject one or more antibody, as described herein, linked to a detectable agent; and b) detecting the detectable agent linked to the antibody thereof bound to AXL.

Optionally, the step of detecting may be performed using PET, SPECT, or fluorescence imaging.

A method of transporting a molecule of interest into cells expressing AXL is described, comprising administering to a subject one or more antibody linked to the molecule of interest, wherein the antibody delivers the molecule of interest to the subject's cells expressing AXL. There may a molecule of interest, such as a detectable agent, a therapeutic agent, a drug, a peptide, an enzyme, a growth factor, a cytokine, a receptor trap, an antibody thereof, a chemical compound, a carbohydrate moiety, a DNA-based molecule, a cytotoxic agent, or a viral vector. In such a method, the molecule of interest may be loaded on or in one or more liposome or nanocarrier. The nanocarrier may comprise one or more nanoparticle, nanowire, nanotube, or quantum dots. Further, the molecule of interest may comprise a cytotoxic agent, such as a cytotoxic agent used for treating cancer.

A method of treating cancer is described, comprising administering an anti-cancer antibody drug conjugate (comprising the antibody described herein) to a subject in need thereof. Further, there is described herein a method of treating cancer comprising administering a cellular therapy, a chimeric antigen receptor (CAR-T cell) therapy, or an oncolytic virus.

Uses for antibody described herein may be for preparation of a medicament comprising an anti-cancer antibody drug conjugate. The antibody is useful in treating cancer in a subject in need thereof. A further use is described in which an anti-cancer antibody drug conjugate is used for treating cancer in a subject in need thereof.

The use of such an antibody is described, and the antibody may be used for preparation of a cellular therapy, a chimeric antigen receptor (CAR-T cell) therapy, or an oncolytic virus.

Anti-AXL antibody drug conjugates are described herein for use as cancer therapeutics. It is desirable to provide immunotherapeutics and immunoconjugates that possess potent and selective anti-cancer activity. Antibody-drug conjugates (ADCs) for the treatment of cancer based on AXL as a cancer target require development of antibodies that can function in a conjugate. AXL is in the TAM family of receptor tyrosine kinases, the overexpression of which has been detected in a wide array of human cancers. Antibodies are described herein that are suited for AXL ADC, determined in part on the basis of surrogate ADC screening of over 250 monoclonal antibodies (mAbs) in several cell line cancer models and cross-reactivity with AXL protein from cynomolgus monkey for toxicity testing. Anti-AXL antibodies for ADC development are described, and Gas6 competition and single domain antibody (sdAb) characterization data is provided herein.

Gas6 competition. In anti-AXL ADCs, the ability of Gas6 (an AXL ligand) to block antibody binding to AXL is an important feature for AXL ADC selection. This ability is referred to herein as Gas6 competition. High concentrations of the Gas6 ligand present systemically or in the tumor microenvironment (but not found in tumor cell lines grown in culture) may account for discrepancies in antibody binding activity seen in vivo versus in vitro. Thus, selection of antibodies to have activities unaffected or weakly affected by Gas6 would ensure that antibody binding is not thwarted by Gas6 in vivo.

Monoclonal Antibodies (mAbs). AXL ADCs were screened from within an anti-AXL mouse mAb library to identify potent ADC internalizers (IC50<1 nM) having activities unaffected by the presence of Gas6.

Single Domain Antibodies (sdAbs). AXL ADC candidates are identified from isolated anti-AXL single domain antibodies (sdAbs, heavy chain variable domains VHH only) by panning from phage display libraries. Techniques used for assessment of sdAbs, herein, include internalization assays and competitive binding assays. Gas6 competition and sdAb characterization data was obtained. In general, single domain antibodies may be up to about 110 amino acids in length, comprising one variable domain (VH) of a heavy-chain antibody. sdAbs lack an Fc region, and thus sdAb-Fc fusions may be prepared.

Epitopes. Epitopes and/or binding domains are described herein.

The term "antibody", also referred to in the art as "immunoglobulin" (Ig), as used herein refers to a protein constructed from paired heavy and light polypeptide chains; various Ig isotypes exist, including IgA, IgD, IgE, IgG, and IgM. Single domain sdAb as well as monoclonal antibodies mAbs are described herein. When an antibody is correctly folded, each chain folds into a number of distinct globular domains joined by more linear polypeptide sequences. For example, the immunoglobulin light chain folds into a variable (VL) and a constant (CL) domain, while the heavy chain folds into a variable (VH) and three constant (CH, CH2, CH3) domains. Interaction of the heavy and light chain variable domains (VH and VL) results in the formation of an antigen binding region (Fv). Each domain has a well-established structure familiar to those of skill in the art.

The term "antibody" may also be used to refer to a fragment of an immunoglobulin molecule, or a derivative of the molecule, which retains the ability to specifically bind to the antigen for a typical comparable time period as observed for the immunoglobulin. The binding region or binding domain of the antibody may comprise variable regions of both the heavy and light chains of the immunoglobulin molecule, or may be a single domain (VHH) molecule. The term "antibody" is used to encompass such fragments of an antibody that retain antigen-binding (which may be referred to herein as an "antibody fragment" or simply "fragment").

Fragments that retain binding ability may include Fab' or Fab fragments, a monovalent fragment which may have VL, VH, CL and CH1 domains, F(ab')$_2$ fragments, biparatopic fragments, bivalent fragments, Fd fragments having VH and CH1 domains, camelid antibodies, nanobodies, isolated complementarity determining region (CDRs), multiple fragments joined by linkers, and other such molecules.

The term "antibody" encompasses polyclonal antibodies, monoclonal antibodies, single domain antibodies, antibody-like polypeptides, humanized antibodies, chimeric antibody molecules, bispecific or biparatopic antibodies, and any fragments not mentioned here specifically which are capable of antigen-binding. The antibody fragment may be a naturally-occurring antibody fragment, may be obtained by manipulation of a naturally-occurring antibody or by using recombinant methods, and may be a non-naturally occurring antibody or fragment. For example, an antibody fragment may include, but is not limited to a Fv, single-chain Fv (scFv; a molecule consisting of VL and VH connected with a peptide linker), Fab, F(ab')$_2$, and multivalent presentations of any of these. Antibody fragments such as those just described may require linker sequences, disulfide bonds, or other type of covalent bond to link different portions of the fragments; those of skill in the art will be familiar with various approaches. Single domain antibody fragments as well as monoclonal antibody fragments are encompassed by the term "antibody".

In a non-limiting example, the antibody fragment may be an sdAb derived from naturally-occurring sources. Heavy chain antibodies of camelid origin lack light chains and thus their antigen binding sites consist of one domain, termed $V_HH$. sdAb have also been observed in shark and are termed $V_{NAR}$. Other sdAb may be engineered based on human Ig heavy and light chain sequences. As used herein, the term "sdAb" includes those sdAb directly isolated from $V_H$, $V_HH$, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, camelization, or other methods of antibody engineering. Also encompassed are homologues, derivatives, or fragments that retain the antigen-binding function and specificity of the sdAb.

SdAb possess desirable properties for antibody molecules, such as high thermostability, high detergent resistance, relatively high resistance to proteases and high production yield. They can also be engineered to have very high affinity by isolation from an immune library or by in vitro affinity maturation. Further modifications to increase stability, such as the introduction of non-canonical disulfide bonds may also be brought to the sdAb.

The structure of a single-domain antibody is established and well known. An sdAb comprises a single immunoglobulin domain that retains the immunoglobulin fold; most notably, only three CDR/hypervariable loops form the antigen-binding site. However, not all CDRs may be required for binding the antigen. For example, and without being limiting, one, two, or three of the CDRs may contribute to binding and recognition of the antigen by the sdAbs described herein. The CDRs of the sdAb or variable domain are referred to herein as CDR1, CDR2, and CDR3.

The described antibodies (including fragments thereof) are specific for AXL, part of the receptor tyrosine kinase subfamily. AXL (Entrez Gene: 558) comprises 894 amino acids organized into an extracellular domain that includes 2 immunoglobulin-like domains and 2 fibronectin type Ill repeats; a transmembrane domain; and an intracellular domain that includes the tyrosine kinase domain (see Prior Art FIG. 1). The AXL protein binds the ligand Gas6, a vitamin K-dependent protein. AXL is normally expressed across many cell types, though expression levels are increased in a number of disease states.

The antibody should exhibit a high degree of internalization. By the term "high degree of internalization", it is meant that the antibody shows sub nM ($IC_{50}$) potency in a saporin- or DM1-conjugated secondary antibody cytotoxicity screening assay in more than one tumor cell line known to express AXL. The antibodies presently described bind to the extracellular domain of the cell surface AXL receptor. The antibodies may then be internalized by the cell and delivered into subcellular organelles, including endosomes and lysosomes. The antibody may also comprise a neutralization function, i.e., it may block signalling through the AXL receptor.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy (VH) and light (VL) domain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, one of which (Kabat Scheme) defines the "complementarity-determining regions" (CDR) based on sequence variability at the antigen-binding regions of the VH and VL domains. Another (Clothia Scheme) defines the "hypervariable loops" (H or L) based on the location of the structural loop regions in the VH and VL domains. As these individual schemes define CDR and hypervariable loop regions that are adjacent or overlapping, those of skill in the antibody art often utilize the terms "CDR" and "hypervariable loop" interchangeably, and they may be so used herein. The International Immunogenetics Information System (IMGT) is used herein, with Kabat numbering also shown. The IMGT numbering system was developed to facilitate comparison of variable domains. In this system, conserved amino acids (such as Cys23, Trp41, Cys104, Phe/Trp118, and a hydrophobic residue at position 89) always have the same position. Additionally, a standardized delimitation of the framework regions (FR1: positions 1 to 26; FR2: 39 to 55; FR3: 66 to 104; and FR4: 118 to 129) and of the CDR (CDR1: 27 to 38, CDR2: 56 to 65; and CDR3: 105 to 117) is provided.

Herein, the CDR sequences noted as IMGT are identified by the descriptive names followed by -A, whereas the descriptive names of Kabat sequences are followed with -B.

The CDR/loops are referred to herein according to the Chothia scheme for CDR H1, and the Kabat scheme for all other CDR. The CDR of the antibodies described herein are referred to as CDR L1, L2, L3 for CDR in the light chain, and CDR H1, H2, H3 for CDR in the heavy chain.

SEQ ID NO:72 provides a known AXL full length His6 sequence, and is provided for information only.

In addition to causing the internalization and activation of conjugated or bound cytotoxic agents, the antibody may lead to antibody-dependent cell-mediated cytotoxicity (ADCC) or complement-dependent cytotoxicity (CDC). As would be known to those of skill in the art, the ADCC and CDC activities are mediated through the constant domains present in various antibody structures.

The antibody may be from any source, human, mouse, or other; may be any isotype, including IgA, IgD, IgE, IgG, and IgM; and may be any type of fragment, including but not limited to Fv, scFv, Fab, F(ab')$_2$.

The antibody may also be chimeric, formed as a combination of protein sequences originating from more than one species. As is known to those of skill in the art, a chimeric antibody is produced by combining genetic material from a nonhuman source (for example but not limited to a mouse) with genetic material from a human. For example, human constant domains can be fused to mouse VH and VL sequences.

The antibody may be "humanized" using any suitable method known in the art, for example, but not limited to CDR grafting and veneering. Humanization of an antibody comprises replacing an amino acid in the sequence with its human counterpart, as found in the human consensus sequence, without loss of antigen-binding ability or specificity; this approach reduces immunogenicity of the antibody when introduced into human subjects. In the process of CDR grafting, one or more than one of the heavy chain CDR defined herein may be fused or grafted to a human variable region (VH or VL), or to other human antibody (IgA, IgD, IgE, IgG, and IgM) or fragment framework regions (Fv, scFv, Fab) or proteins of similar size and nature onto which CDR can be grafted (for example, see Nicaise et al, 2004). In such a case, the conformation of said one or more than one hypervariable loop is likely preserved, and the affinity and specificity of the antibody for its target (i.e., AXL) is likely minimally affected. CDR grafting is known in the art. In one non-limiting example of such a humanized antibody, a CDR as described above from a mouse source may be grafted onto human light chain and heavy chain framework regions.

Veneering, also referred to in the art as "variable region resurfacing", involves humanizing solvent-exposed positions of the antibody. Thus, buried non-humanized residues, which may be important for CDR conformation, are preserved while the potential for immunological reaction against solvent-exposed regions is minimized. Veneering is known in the art and essentially involves replacing exposed residues in the framework region of the native antibody or fragment thereof with the amino acid residues in their human counterpart (Padlan, 1991; Gonzales et al 2005).

Persons of skill in the art would also be amply familiar with methods of preparing such humanized antibody fragments and humanizing amino acid positions. See, for example, Vincke et al., 2009. As known by those of skill in the art, it may be necessary to incorporate certain native amino acid residues into the human framework in order to retain binding and specificity. Humanization by CDR grafting is known in the art (for example, see Tsurushita et al, 2005; Jones et al, 1986; Tempest et al, 1991; Riechmann et al, 1988; Queen et al, 1989; Gonzales et al, 2005), and thus persons of skill would be amply familiar with methods of preparing such humanized antibody or fragments thereof.

An isolated or purified antibody specific for AXL that may be a chimeric antibody comprising the VH and VL as defined above and a human IgG1 framework. For example, the human IgG1 framework may comprise a human kappa light chain and a human IgG1 heavy chain.

Monoclonal Antibodies

High-affinity monoclonal antibodies (mAb) directed against AXL are described. The mAbs were generated by genetic immunization (i.e., by injecting DNA that encodes rhAXL-ECD). The mAb were screened using a functional assay designed to identify antibodies that exhibit a high degree of internalization.

Five anti-hAXL mAb identified were functionally characterized for potential as an antibody-drug conjugate (ADC). These antibodies are designated herein as: F107-7H5, F107-8D12, F111-5E9, F111-3C8, and F107-10G1. These anti-human AXL antibodies were selected because they showed sub nM (IC$_{50}$) potency in a saporin-conjugated secondary antibody-based cytotoxicity screening assay in at least two of the following cell lines: U87 glioblastoma, A549 alveolar adenocarcinoma, and MDA-MB-231 breast adenocarcinoma. They also showed toxicity on H292 lung carcinoma cells, A549 cells and MDA-MB-231 cells, when conjugated to DM1. Epitope binning analyses indicated that the selection of these antibodies, which was based on potency in the conjugated secondary antibody screening assay, resulted in all five mAb binding to the following epitopes: two located in the Ig-like domain 1 (F107-7H5 and F107-8D12) and one in Ig-like domain 2 (F111-3C8 and F111-5E9) of AXL. It is noted that binding of F107-10G1 is also in the Ig-like domain 1, but at a site distinct from that of F107-7H5 and F107-8D12.

Sequence Identity and Characteristics

A substantially identical sequence may comprise one or more conservative amino acid mutations. It is known in the art that one or more conservative amino acid mutations to a reference sequence may yield a mutant peptide with no substantial change in physiological, chemical, physicochemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). These conservative amino acid mutations may be made to the framework regions of the antibody while maintaining the CDR sequences listed above and the overall structure of the antibody; thus the specificity and binding of the antibody are maintained.

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to a normalized consensus hydrophobicity scale. Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Sequence identity can, for example, be calculated by software such as NCBI BLAST2 service maintained by the Swiss Institute of Bioinformatics, BLAST-P, Blast-N, or FASTA-N, or any other appropriate software that is known in the art.

Substantially identical sequences, as described herein, may be at least 90% identical; in another example, the substantially identical sequences may be at least 90, 91, 92, 93, 94, 95, 96, 97, 98, 99, or 100% identical, or any percentage there between, at the amino acid level to sequences described herein. Importantly, the substantially identical sequences retain the activity and specificity of the reference sequence. In a non-limiting embodiment, the difference in sequence identity may be due to conservative amino acid mutation(s). In a non-limiting example, an antibody comprising a sequence at least 85%, 90%, 95%, 98% or 99% identical to the specific sequence described herein is encompassed.

When sequences are is compared, the present antibodies noted as mAbs 3C7, 8D12 and 7H5 are related to one another with about 90% similarity or greater (or ≥90% identity). Variations in a sequence that nevertheless result in substantially identical activity would be considered substantially identical sequences.

Changes in the sequences due to alterations, such as humanization, may alter the sequences in a manner that is predictable, and understood to those of skill in the art. Thus, such altered sequences may have a greater number of altered residues so that identity is below the 90% value mentioned above. Variation in the sequence may be present in regions outside of the CDRs, or may be within the CDRs, provided that substantially identical binding is achieved.

The antibody may also comprise additional sequences to aid in expression, detection or purification of a recombinant antibody. Any such sequences or tags known to those of skill in the art may be used. For example, the antibody may comprise a targeting or signal sequence (for example, but not limited to ompA), a detection/purification tag (for example, but not limited to c-Myc, His$_5$, His$_6$, or His$_8$G), or a combination thereof. In another example, the signal peptide may be MVLQTQVFISLLLWISGAYG (SEQ ID NO:59) or MDWTWRILFLVAAATGTHA (SEQ ID NO:60). In a further example, the additional sequence may be a biotin recognition site. As is also known to those of skill in the art, linker sequences may be used in conjunction with the additional sequences or tags, or may serve as a detection/purification tag.

Multimerization, Linking, and Cargo

The antibody may be in a multivalent display format, also referred to herein as multivalent presentation. Multimerization may be achieved by any suitable method of known in the art. For example, and without being limiting in any manner, multimerization may be achieved using self-assembly molecules, and/or by producing pentabodies by expressing a fusion protein comprising the antibody and the pentamerization domain of the B-subunit of an AB$_5$ toxin family. The pentamerization domain then assembles into a pentamer. A multimer may also be formed using the multimerization domains, which may be referred to as a "combody" form to describe a fusion of the antibody, with a coiled-coil peptide resulting in a multimeric molecule. Other forms of multivalent display are also encompassed herein. For example, and without being limiting, the antibody may be presented as a dimer, a trimer, or any other suitable oligomer. This may be achieved by methods known in the art, for example with direct linking connection, with a c-jun/Fos interaction, using a knob into holes interaction.

Each subunit of the multimers described above may comprise the same or different antibodies, which may have the same or different specificity. Additionally, the multimerization domains may be linked to the antibody using a linker, as required; such a linker should be of sufficient length and appropriate composition to provide flexible attachment of the two molecules, but should not hamper the antigen-binding properties of the antibody. For example, and without being limiting in any manner, the antibody may be linked to a cargo molecule. The cargo molecule may be any suitable molecule. For example, the cargo molecule may be a detectable agent, a therapeutic agent, a drug, a peptide, an enzyme, a growth factor, a cytokine, a receptor trap, an antibody or fragment thereof (e.g., IgG, scFv, Fab, V$_H$H, V$_H$, VL, etc.) a chemical compound, a carbohydrate moiety, DNA-based molecules (anti-sense oligonucleotide, microRNA, siRNA, plasmid), a cytotoxic agent, viral vector (adeno-, lenti-, retro-), one or more liposomes or nanocarriers loaded with any of the previously recited types of cargo molecules, or one or more nanoparticle, nanowire, nanotube, or quantum dots. The antibody may be linked to the cargo molecule using any method known in the art (recombinant technology, chemical conjugation, etc.).

In one non-limiting example, the cargo molecule may be a detectable label, a radioisotope, a paramagnetic label such as gadolinium or iron oxide, a fluorophore, a fluorescent agent, Near Infra-Red (NIR) fluorochrome or dye such as Cy5.5, an echogenic microbubble, an affinity label (for example biotin, avidin, etc), a detectable protein-based molecule, nucleotide, quantum dot, nanoparticle, nanowire, or nanotube or any other suitable agent that may be detected by imaging methods. In a specific, non-limiting example, the anti-AXL antibody may be linked to a near infrared fluorescence (NIRF) imaging dye, for example Cy5.5, Alexa680, Dylight680, or Dylight800.

The antibodies described herein may be used in cellular therapies, in chimeric antigen receptor (CAR-T cell) therapy, in oncolytic viruses, and for preparation of these and in other therapeutic compositions.

In another specific, non-limiting embodiment, the antibody is linked to a drug, thus providing an antibody-drug conjugate (ADC). The drug may be any type of drug, for example but not limited to a cytotoxic or chemotherapeutic agent. The cytotoxic or chemotherapeutic agent may include, but is not limited to microtubule inhibiting agents (such as maytansines and auristatins), DNA damaging agents (such as calicheamicin and duocarmydin), RNA polymerase inhibitors (such as alpha-amantin), anti-metabolites, agents that react with DNA (such as alkylating agents, coordination compounds, platinum complexes, DNA cross-linking compounds, etc.), inhibitors of transcription enzymes, tyrosine kinase inhibitors, topoisomerase inhibitors, DNA minor-groove binding compounds, antimitotic agents (such as vinca alkyloids and taxanes), antitumor antibiotics, hormones, enzymes, and other potent drugs. As is known to those of skill in the art, the antibody-drug conjugate allows for targeted delivery of a drug, thus limiting systemic exposure. In this construct, the antibody binds to the extracellular domain of the cell surface AXL receptor; the drug linked to the antibody is thus internalized and delivered intracellularly. The drug is then either active in the cell directly or is first activated via the endosome and can then act on the cell.

The cargo molecule as described herein may be linked, also referred to herein as "conjugated", to the antibody by any suitable method known in the art. For example, and without being limiting, the cargo molecule may be linked to the peptide by a covalent bond or ionic interaction. The linkage may be achieved through a chemical cross-linking reaction, or through fusion using recombinant DNA methodology combined with any peptide expression system, such as bacteria, yeast or mammalian cell-based systems. When conjugating the cargo molecule to the antibody, a suitable linker may be used. Methods for linking an antibody to a cargo molecule such as a therapeutic or detectable agent would be well-known to a person of skill in the art.

Nucleic acid sequences encoding the molecules as described herein are also encompassed. Given the degeneracy of the genetic code, a number of nucleotide sequences would have the effect of encoding the desired polypeptide, as would be readily understood by a skilled artisan. The nucleic acid sequence may be codon-optimized for expression in various micro-organisms. Vectors comprising the nucleic acids as just described are also encompassed. Furthermore, cells comprising the nucleic acid and/or vector as described are encompassed.

Isolated or purified antibodies may be immobilized onto a surface using various methodologies; for example, the antibody may be linked or coupled to the surface via His-tag coupling, biotin binding, covalent binding, adsorption, or by other routes. Immobilization of the antibody may be useful in various applications for capturing, purifying or isolating proteins. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, plastic, stainless steel, a film, or any other useful surface such as nanoparticles, nanowires and cantilever surfaces. A purified antibody immobilized onto a surface may be used in a variety of methods, including diagnostic methods.

An in vitro method of detecting AXL is described, comprising contacting a sample with one or more than one isolated or purified antibody linked to a detectable agent. The AXL-antibody complex can then be detected using detection and/or imaging technologies known in the art. The sample in the method as just described may be any suitable tissue sample, for example but not limited to a serum sample, a vascular tissue sample, or a tumour tissue sample; the sample may be from a human or animal subject. The step of contacting is done under suitable conditions, known to those skilled in the art, for formation of a complex between the antibody and AXL. The step of detecting may be accomplished by any suitable method known in the art, for example, but not limited to optical imaging, immunohistochemistry, molecular diagnostic imaging, ELISA, or other suitable method. For example, the isolated or purified antibody linked to a detectable agent may be used in immunoassays (IA) including, but not limited to enzyme IA (EIA), ELISA, "rapid antigen capture", "rapid chromatographic IA", and "rapid EIA". In a specific, non-limiting embodiment, the in vitro method is for detection of AXL in circulating cells and the sample is a serum sample.

AXL Detection and Disease Diagnosis

An in vivo method of detecting AXL expression in a subject is described. The method comprises administering one or more than one isolated or purified antibody linked to a detectable agent to the subject, then detecting the labelled antibody bound to AXL. The step of detecting may comprise any suitable method known in the art, for example, but not limited to PET, SPECT, or fluorescence imaging, or any other suitable method. The method as just described may be useful in detecting the expression of AXL in tissues, for example but not limited to tumor tissues.

The in vivo detection step in the methods described above may be whole body imaging for diagnostic purposes or local imaging at specific sites, such as but not limited to sites of solid tumor growth, in a quantitative manner to assess the progression of disease or host response to a treatment regimen. The detection step in the methods as described above may be immunohistochemistry, or a non-invasive (molecular) diagnostic imaging technology including, but not limited to: optical imaging; positron emission tomography (PET), wherein the detectable agent is an isotopes such as $^{11}C$, $^{13}N$, $^{15}O$, $^{18}F$, $^{64}Cu$, $^{62}Cu$, $^{124}I$, $^{76}Br$, $^{82}Rb$ and $^{68}Ga$, with $^{18}F$ being the most clinically utilized; single photon emission computed tomography (SPECT), wherein the detectable agent is a radiotracer such as $^{99m}Tc$, $^{111}In$, $^{123}I$, $^{201}Tl$, $^{133}Xe$, depending on the specific application; magnetic resonance imaging (MRI), wherein the detectable agent may be, for example and not limited to gadolinium, iron oxide nanoparticles and carbon-coated iron-cobalt nanoparticles thereby increasing the sensitivity of MRI for the detection of plaques; or Contrast-Enhanced Ultrasonography (CEUS) or ultrasound, wherein the detectable agent is at least one acoustically active and gas-filled microbubble. Ultrasound is a widespread technology for the screening and early detection of human diseases, and is less expensive than MRI or scintigraphy and safer than molecular imaging modalities such as radionuclide imaging because it does not involve radiation.

Delivery of Molecules to Cells Expressing AXL

A method is described for transporting a molecule of interest into cells expressing AXL. The method comprises administering the molecule linked to an antibody to a subject. The molecule may be any desired molecule, including the cargo molecules, as previously described; the molecule may be "linked" to the antibody using any suitable method, including, but not limited to conjugation or expression as a fusion protein. The administration may be by any suitable method, for example parenteral administration, including but not limited to intravenous (iv), subcutaneous (sc), and intramuscular (im) administration. In this method, the antibody delivers the desired molecule to cells in a targeted fashion.

Compositions

Compositions are provided, which comprise one or more than one isolated or purified antibody. The composition may comprise a single antibody as described above, or may be a mixture of antibodies. Furthermore, in a composition comprising a mixture of antibodies, the antibodies may have the same specificity, or may differ in their specificities; for example, the composition may comprise antibodies specific to AXL (same or different epitope). The antibody may be biparatopic. The composition may also comprise one or more antibody linked to one or more than one cargo molecule. For example, the composition may comprise one or more than one ADC as described herein.

An antibody-drug conjugate (ADC) approach, in which an anti-AXL antibody is used to deliver a potent cytotoxic drug, increases the patient population that is likely to respond to the drug. Without being bound by theory, this may be due largely to the requirement for increased expression of AXL rather than a requirement for ongoing AXL activity. Another advantage is that an ADC can frequently be given in the case of acquired resistance to antibodies.

A composition in which the antibody is provided may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, when the composition is provided in suspension form, the carrier may comprise water, saline, a suitable buffer, or additives to improve solubility and/or stability; reconstitution to produce the suspension is effected in a buffer at a suitable pH to ensure the viability of the antibody. Dry powders may also include additives to improve stability and/or carriers to increase bulk/volume; for example the dry powder composition may comprise sucrose or trehalose. In a specific, non-limiting example, the composition may be so formulated as to deliver the antibody to the gastrointestinal tract of the subject. Thus, the composition may comprise encapsulation, time-release, or other suitable technologies for delivery of the antibody. It would be within the competency of a person of skill in the art to prepare suitable compositions comprising the present compounds.

The antibody may be used in the treatment of diseases or conditions where AXL expression is dysregulated, or may be used in the preparation of a medicament for such use. The antibody may be linked to a cargo molecule, or may be included in a composition. Diseases and conditions that may be treated using the antibody described herein include, but are not limited to solid cancer tumors, including, but not limited to, breast, renal, endometrial, ovarian, thyroid, and non-small cell lung carcinoma, melanoma, prostate carcinoma, sarcoma, gastric cancer and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis, osteoporosis and cataracts. Diseases and conditions that may be treated also include those affected by the following biological processes: Invasion, migration, metastasis, or drug resistance as manifested in cancer; stem cell biology as manifested in cancer; invasion, migration, adhesion, or angiogenesis; vascular remodeling; bone homeostasis; viral infection; or differentiation as manifested in obesity. The compounds of formula (I) may also be used to modulate inflammatory processes by treating sepsis, acting as vaccine adjuvants, and/or potentiating the immune response in immuno-compromised patients. In one non-limiting example, the disease or condition may be metastatic cancer.

The present invention will be further illustrated in the following examples. However, it is to be understood that these examples are for illustrative purposes only and should not be used to limit the scope of the present invention in any manner.

EXAMPLES

Example 1: Production of Anti-AXL Antibodies

Monoclonal antibodies (mAb) against AXL were generated by immunizing mice with the extracellular domain of a recombinant human AXL protein (rhAXL-ECD; SEQ ID NO:58) as well as by genetic immunization.

Production of rhAXL-ECD: A pTT5 construct containing a synthetic recombinant fragment of C-terminally His8-tagged recombinant human (rh)AXL extracellular domain (ECD; SEQ ID NO:71) was expressed in CHO cells, purified by Ni-agarose and verified by SDS-PAGE (data not shown).

Immunizations: Mouse mAb were generated by genetic immunization. For genetic immunizations, mice were bled (pre-immune serum) and immunized on day 0 and day 42 by hydrodynamic tail vein delivery technique (HTV) using 100 µg of a pTT40 expression plasmid for expression of soluble rhAXL-ECD. Mice were bled 7-10 days later and the serum titer was measured by ELISA. Four to five months later, a booster injection using 100 µg of pTT40-AXL-H8G was done by HTV 3 to 4 days prior to fusion experiment.

Fusion experiment and hybridoma selection. All manipulations were done under sterile conditions. Spleen cells were harvested in IMDM (Hy-Clone) and fused to NS0 myeloma cell line using PEG fusion protocol. To this end, spleen cells and myeloma cells were washed in IMDM, counted in RBC lysing buffer (Sigma) and mixed together at a 5:1 ratio. Pelleted cells were fused together by adding 1 ml of a 50% solution of PEG 4000 (EMD-Millipore) in PBS drop-wise over one minute, and incubated at 37° C. for an additional 90 sec. The reaction was stopped by addition of 30 ml of IMDM at 22° C. over 2 min. After a 10 min incubation, freshly fused cells were spun at 233×g for 10 min. Cells were washed once in IMDM supplemented with 10% heat inactivated FBS (Sigma), and suspended at a concentration of $2\times10^5$ input myeloma cells per ml in HAT selection medium (IMDM) containing 20% heat inactivated FBS, penicillin-streptomycin (Sigma), 1 ng/ml mouse IL-6 (Biosource), HAT media supplement (Sigma) and L-glutamine and incubated at 37° C., 5% $CO_2$. The next day, hybridoma cells were washed and suspended at a concentration of $2\times10^5$ input myeloma cells per ml in semi-solid medium D (StemCell) supplemented with 5% heat inactivated FBS, 1 ng/ml mouse IL-6 and 10 µg/ml FITC-Fab'2 Goat anti-mouse IgG (H+L) (Jackson). The cell mixture was plated in Petri dish (Genetix) and further incubated for 6-7 days at 37° C., 5% $CO_2$. Secretor clones were then transferred using a mammalian cell clone picker (CLONEPIX™ FL, Molecular Devices) into sterile 96-w plates (Costar) containing 200 µl of IMDM supplemented with 20% heat inactivated FBS, penicillin-streptomycin (Sigma), 1 ng/ml mouse IL-6 (Biosource), HT media supplement (Sigma) and L-glutamine and incubated for 2-3 days at 37° C., 5% $CO_2$.

Hybridoma supernatant was collected and evaluated for binding to the rhAXL-ECD protein by ELISA. To this end, 96-w half-area plates (Costar) were coated with 25 µl of rhAXL-ECD at 5 µg/ml in PBS and incubated overnight at 4° C. Microplates were washed 3 times with PBS, blocked with PBS-BSA 1%, and 25 µl of hybridoma supernatant were added and incubated at 37° C., 5% $CO_2$ for 2 hours. Plates were washed 4 times with PBS-TWEEN™ 20 0.05% and incubated for one hour at 37° C., 5% $CO_2$ with 25 µl of secondary antibody alkaline phosphatase conjugated F(ab)'2 goat anti-mouse IgG (H+L) (Jackson Immunoresearch) diluted 1/3000 in blocking buffer. After 4 washes with PBS-TWEEN™20 0.05%, 25 µl of a 1 mg/ml pNPP substrate solution was added and further incubated for one hour at 37° C. OD405 nm measurements were done using a microplate reader (Spectramax 340 PC, Molecular Devices).

ELISA positive antibodies were selected (including clones F107-7H5, F107-8D12, F111-5E9, F111-3C8, and F107-10G1) and small scale purifications done on 10 ml volumes of hybridoma supernatant. mAb were purified via adsorption onto Protein G Mag SEPHAROSE™ Extra (GE Healthcare Life Sciences #28-9670-70), washes in PBS, elution twice with 200 µl of glycine 200 mM pH 2.5 and neutralization in TRIS-HCl 1M pH 9.0. Purified antibodies were desalted using Zeba Spin resin (Pierce) pre-equilibrated in PBS and filter sterilized through 0.22 µM membrane (Millipore). The final concentration of the antibody solutions was determined by nano-drop (#ND-1000).

Example 2: Cross-Reactivity Assessment of Anti-AXL mAbs

The cross-reactivity binding properties of the anti-hAXL monoclonal antibodies purified in Example 1 for recombinant AXL ectodomain were evaluated.

To evaluate the cross-reactivity of the mAb to other members of the TAM receptor tyrosine kinase subfamily, binding of the mAb to rhAXL-ECD, rhMER-ECD, rhTyro-3 and BSA (negative control) was measured by ELISA. 96-w half-area plates (Costar) were coated with 25 µl of rhAXL-ECD, rhMER-ECD, rhTyro-3 or BSA at 5 µg/ml in PBS and incubated overnight at 4° C. Microplates were washed 3 times with PBS, blocked with PBS-BSA 1%, and 25 µl of a 10 µg/ml diluted in PBS-BSA 1% were added and incubated at 37° C., 5% $CO_2$ for 2 hours. Plates were washed 4 times with PBS-TWEEN™ 20 0.05% and incubated for one hour at 37° C., 5% $CO_2$ with 25 µl of secondary antibody alkaline phosphatase conjugated F(ab)'2 goat anti-mouse IgG (H+L) (Jackson Immunoresearch) diluted 1/5000 in blocking buffer. After 4 washes with PBS-Tween 20 0.05%, 25 µl of a 1 mg/ml pNPP substrate solution was added and further incubated for one hour at 37° C. OD405 nm measurements were done using a microplate reader (Spectramax 340 PC, Molecular Devices).

Table 1 provides the results of cross-reactivity assessment of anti-AXL monoclonal antibodies on other targets from the same protein family. Measurements at OD405 nm are shown.

TABLE 1

Cross-Reactivity Assessment of Anti-AXL mAbs

| Purified Antibody | Coating antigen | | | |
|---|---|---|---|---|
| | AXL | MER | Tyro3 | BSA |
| F107-7H5-2 | 2.403 | 0.000 | 0.000 | 0.000 |
| F107-8D12-2 | 2.592 | 0.000 | 0.000 | 0.000 |
| F107-10G1-3 | 1.758 | 0.000 | 0.000 | 0.000 |
| F111-3C8-2 | 2.301 | 0.000 | 0.000 | 0.000 |
| F111-5E9-2 | 1.364 | 0.000 | 0.000 | 0.000 |

The results of the cross-reactivity assessment indicate that the five mAb specifically bind the extracellular domain of AXL, i.e. they do not cross-react with BSA or the extracellular domains of other members of the TAM family, namely Tyro3 and MER.

Example 3: Functional Characterization for ADC Potential

The anti-hAXL-ECD monoclonal antibodies purified in Example 1 were evaluated for their internalizing ability and antibody-drug conjugate (ADC) potential in an ADC surrogate screening assay. Non-small cell lung cancer (NSCLC) A549 cells, breast cancer MDA-MB 231 cells, or glioblastoma U87MG cells were used, all of which express moderate to high levels of AXL. mAbs were selected that show low or sub nM ($IC_{50}$) potency in secondary conjugate saporin-based cytotoxicity screening in more than one tumor cell line known to express the tumor target of interest (i.e., AXL).

Cell culture. The following cell lines were obtained from ATCC and cultured according to supplier's recommendations: A549 human non-small lung cancer (NSCLC), MDA-MB-231 triple negative (ER-/PR-/HER2low) breast cancer (TNBC), and U87MG glioblastoma cell lines. Generally, cells were passaged once or twice a week and used within 4-6 weeks for all experiments.

Evaluation of antibody-mediated cytotoxicity as antibody-drug conjugates. Primary mouse antibodies (typically 1 nM in concentration) were incubated with an equimolar concentration of anti-mouse secondary antibody chemically conjugated with saporin toxin (Advanced Targeting Systems, San Diego, Calif.), a ribosome inactivating enzyme that needs to be internalized to cause cell death. The antibody complex was then added to the cell types indicated (plated in triplicate) and their effects on cell viability measured after 3 days of incubation at 37° C. Incubation with no primary antibody (secondary antibody alone) or an irrelevant primary antibody (control human IgG) were used to assess non-target-directed cytotoxicity. Cell viability & metabolism were measured using conventional methods such as the use of a resurizin dye like Alamar Blue or a reagent to measure protein content, such as sulforhodamine B.

A549 NSCLC cells were seeded in RPMI-5% FBS in 96-well plates at a density of 2000 cells/well in 100 µl RPMI-5% FBS. The next day, 20 nM of anti-AXL mAb was mixed with 20 nM of the Mab-Zap secondary antibody (Advanced Targeting Systems, San Diego, Calif.), and was incubated for 30 min. at room temperature; 11 µl of this mixture was added to the cells in triplicate such that a 1 nM final concentration of the 1:1 complex of anti-AXL mAb (F107-7H5, F107-8D12, F111-5E9, F111-3C8, or F107-10G1) and the saporin-conjugated anti-mouse secondary antibody (Mab-Zap) was incubated with the cells. After 72 hr of incubation (37° C., 5% $CO_2$, humidified incubator) cell viability was determined using Alamar Blue according to manufacturer's direction (BIOSOURCE). Subsequently, antibodies that caused more than a 50% decrease in A549 cell viability at 1 nM concentration were also tested for cytotoxic effects on breast cancer MDA-MB 231 cells, or glioblastoma U87MG cell lines using the method described above.

Figure 2:
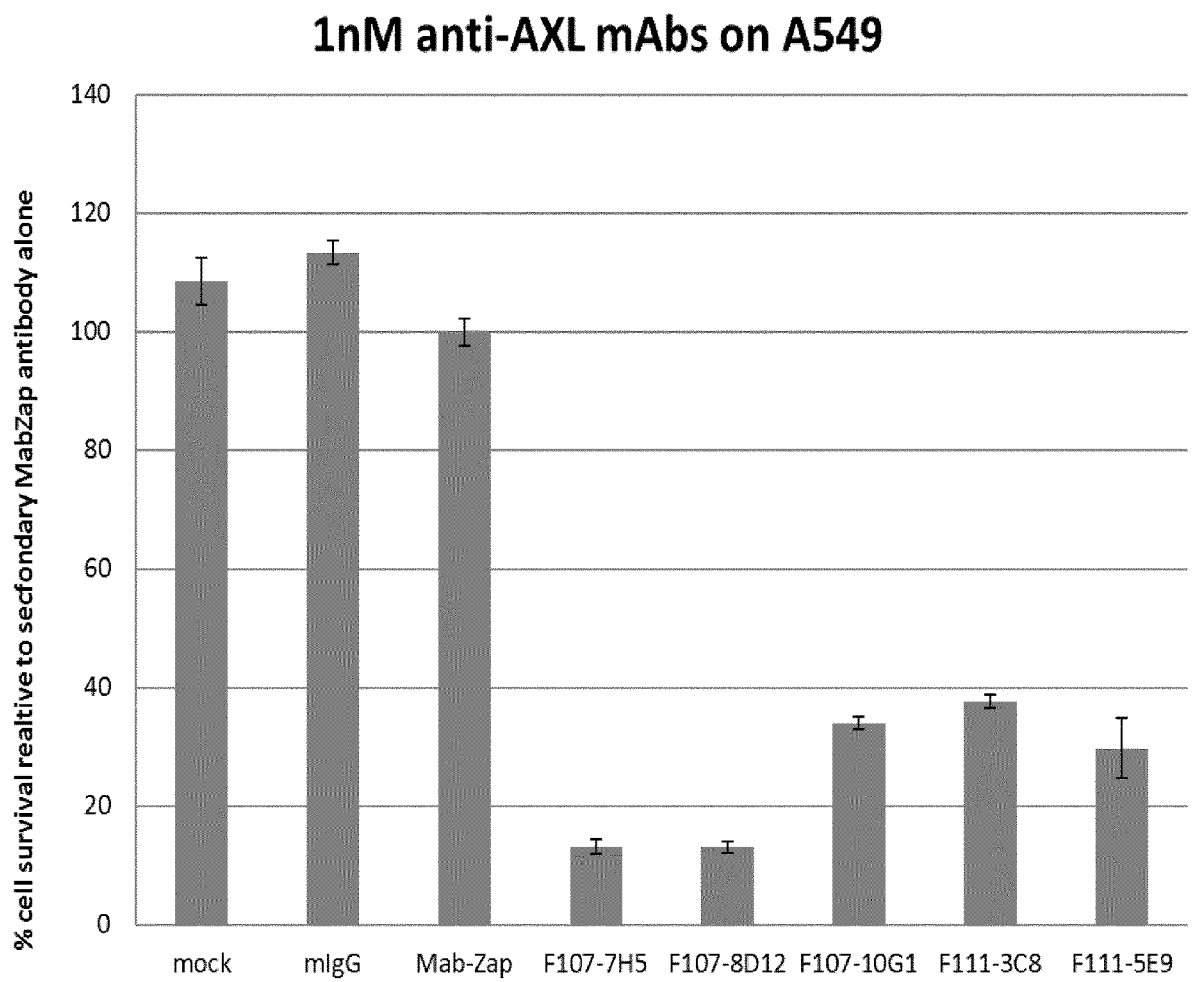
FIG. 2 shows results of the effect of anti-AXL mAbs on A549 cell survival.

FIG. 2 shows results of the ADC surrogate screening assay for anti-hAXL-ECD mAb. The antibodies in the assay caused a marked reduction in A549 cell survival compared to cells treated with secondary conjugate alone (Mab-Zap). Displayed are the average values+SEM of a triplicate experiment.

In FIG. 2, where the survival of the cells is expressed relative to that of the mAb-ZAP secondary conjugate alone (shown as 100%). The selected mAb clones (F107-7H5, F107-8D12, F107-10G1, F111-3C8, and F111-5E9) caused more than 50% reduction in viability in A549 cells and in at least one more cell line and were selected for direct conjugation to the highly cytotoxic drug DM1. The high degree of cytotoxicity associated with these 5 antibodies ($IC_{50}$<1 nM), from among more than 250 primary mouse mAb tested, demonstrates that they exhibit a high degree of internalization and appropriate intracellular routing to achieve activation of the saporin toxin, making them ideal for ADC development. Not surprisingly, antibodies identified in this screen all exhibited appreciable binding to AXL on the surface of tumor cells (FIG. 3).

Figure 3:
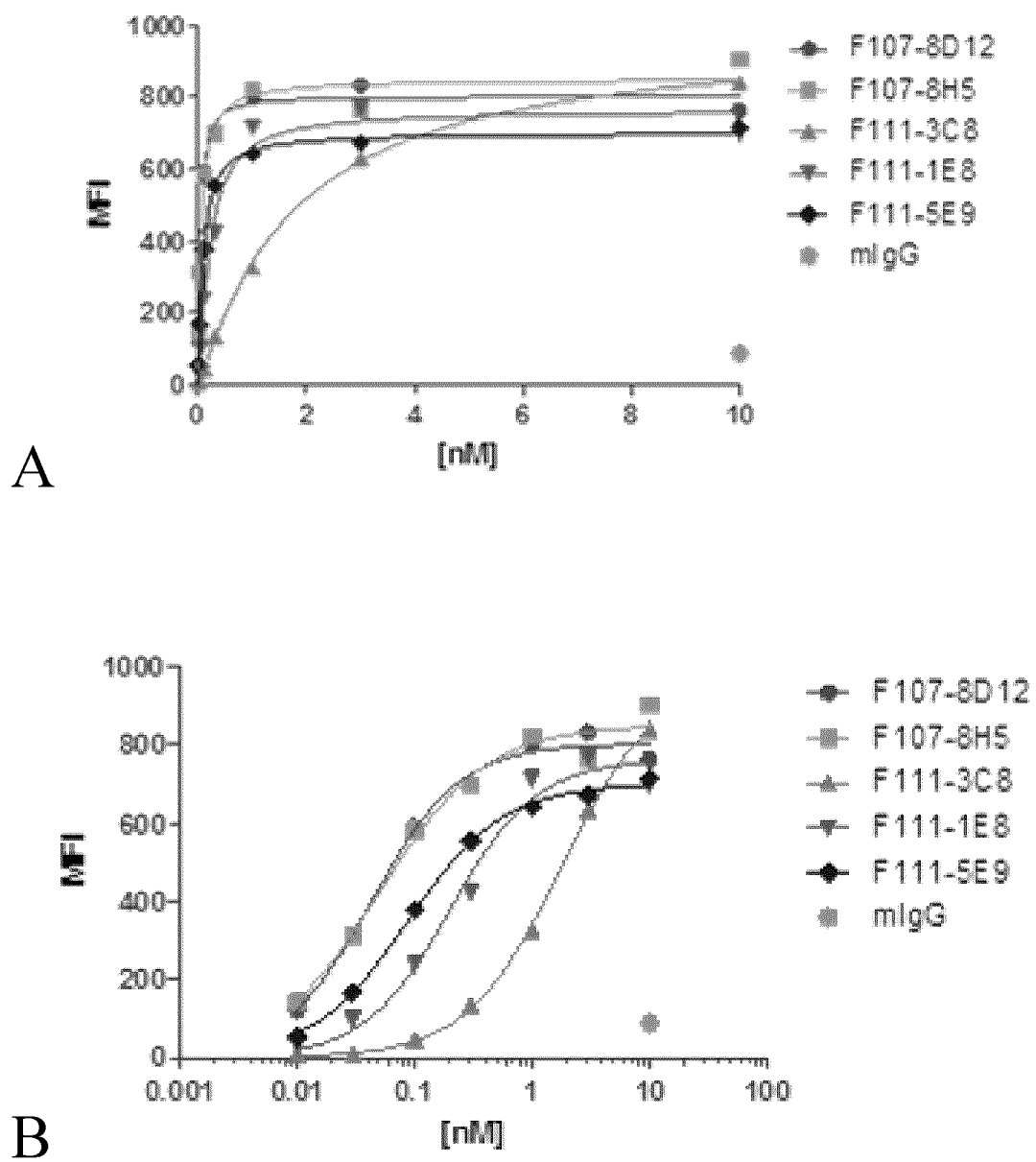
FIG. 3 shows results of flow cytometry experiments determining the binding properties of anti-AXL mAb to cell surface-expressed AXL on H292 cells.

FIG. 3 shows results of flow cytometry experiments determining the binding properties of anti-AXL mAb to cell surface-expressed AXL. Panel A shows the linear scale dose-response curve, while Panel B shows the log scale dose response curve.

Example 4: DM1 Conjugation and ADC Testing

The anti-hAXL-ECD monoclonal antibodies purified in Example 1 were conjugated via lysine residues to succinimidyl trans-4-[maleimidylmethyl] cyclohexane-1-carboxylate (SMCC) linked to N2'-deacetyl-N2'-(3-mercapto-1-oxopropyl)-maytansine (DM1). Product purity and drug:antibody ratio were determined by UPLC based size-exclusion chromatography (SEC).

Conjugation: Purified anti-hAXL-ECD mAb (F107-7H5, F107-8D12, F111-5E9, F111-3C8, or F107-10G1; Example 1) were buffer-exchanged into Conjugation buffer (100 mM Sodium phophate, 20 mM NaCl, 2 mM EDTA pH 7.2) using pre-equilibrated spin desalting columns. The concentration of each mAb was adjusted to 2 mg/mL with conjugation buffer and 200 µg total of each was used for conjugation. A stock solution of SMCC-DM1 was prepared in dimethylacetamide (DMA). SMCC-DM1 from the DMA stock solution was added to each mAb to achieve a molar SMCC-DM1:mAb ratio of 10.0. The solution was mixed thoroughly and incubated at 37° C. for 3 hours. The reaction was stopped by passing the reaction mixture through two spin desalting columns equilibrated in Conjugation buffer with 0.02% w/v Polysorbate-20 added.

Drug-antibody ratio (DAR) was determined by integrating the monomeric peak from the UPLC-SEC chromatogram at both 280 nm and 252 nm and comparing these to the ratios of extinction coefficients for the unconjugated antibody and free drug at the same wavelengths. Percent monomer was determined from the total integrated areas of monomer, high-molecular weight species and low-molecular weight species observed in the chromatogram. Results are shown in Table 2, which provides drug-antibody ratio and percent aggregate determined by UPLC-SEC for F107-7H5, F107-8D12, F111-5E9, F111-3C8, and F107-10G1 conjugated to DM1.

TABLE 2

Drug-antibody Ratio and Percent Aggregate

| mAb | DAR | Percent Aggregate |
|---|---|---|
| F111-3C8 | 7.21 | 27.0 |
| F107-7H5 | 5.46 | 1.1 |
| F107-8D12 | 4.90 | 1.8 |
| F107-10G1 | 5.21 | 0.7 |
| F111-5E9 | 5.22 | 1.1 |

Cell culture. The NCI-H292 and A549 human non-small cell lung cancer (NSCLC) and the MDA-MB-231 triple negative (ER-/PR-/HER2low) breast cancer (TNBC) cell lines were obtained from ATCC and cultured according to supplier's recommendations. HaCaT cells are a spontaneously immortalized, human keratinocyte line that has been widely used for studies of skin biology and differentiation. This cell line was obtained from Cell Line Services, DKFZ, Heidelberg, Germany and cultured according to supplier's recommendations. Generally, cells were passaged once or twice a week and used within 4-6 weeks for all experiments.

ADC testing: Anti-AXL ADC prepared above were tested for their effects on viability of various cultured cell lines known to express AXL, including the non-small cell lung cancer (NSCLC) NCI-H292 and A549 cell lines, human breast adenocarcinoma MDA-MB-231 tumor cell line, as well as immortalized keratinocytes. Following 5 days of exposure, cell growth/viability was assessed using sulforhodamine B reagent and dose-response curves were generated to measure their potency ($IC_{50}$) and efficacy (% maximal inhibition) using the log(inhibitor) vs. response—Variable slope (four parameters) model from GraphPad Prism v6.0 software.

Figure 4:
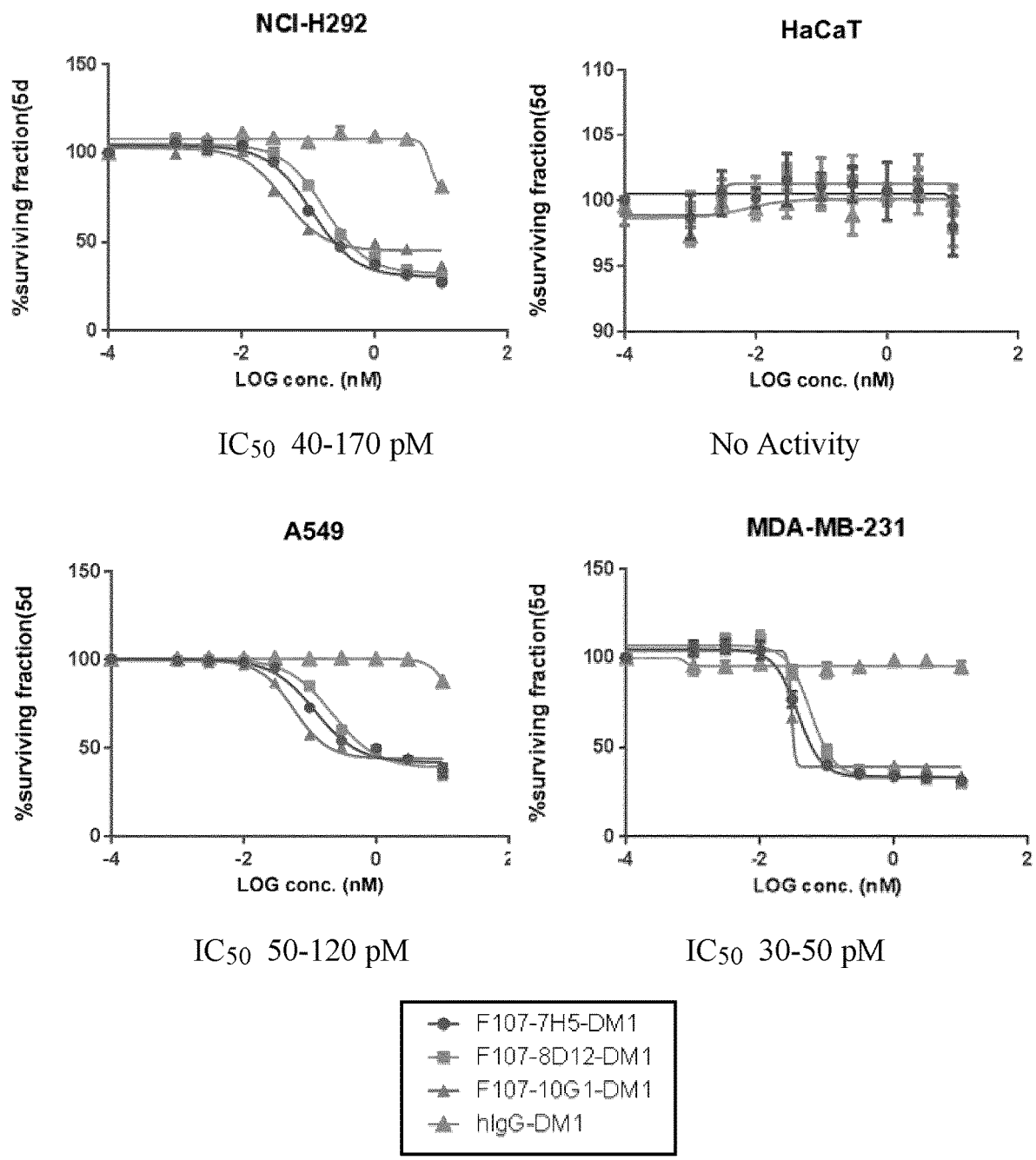
FIG. 4 shows results of the activity of anti-AXL-DM1 conjugates on cell viability in a H292 tumor cell line, a A549 cell line, human breast adenocarcinoma MDA-MB-231 tumor cell line, and immortalized HaCaT keratinocyte cells.

FIG. 4 shows results of the activity of anti-AXL-DM1 conjugates on cell viability in H292 tumor cell lines, A549 cell lines, human breast adenocarcinoma MDA-MB-231 tumor cell line, as well as immortalized HaCaT keratinocyte cells, which express AXL.

The DM1-conjugated anti-AXL antibodies demonstrated good efficacy (from 55-74% maximal growth inhibition) and strong potency ($IC_{50}$<0.1 nM) in the tumor cell lines analyzed compared to the non-targeted irrelevant human IgG-DM1 conjugate negative control. In contrast, very little toxicity was seen on non-tumorigenic, immortalized HaCaT keratinocyte cells, which express AXL.

Table 3 provides the results of ADC testing of anti-AXL antibodies. % max inh=percent maximal inhibition.

TABLE 3

Results of ADC Testing of Anti-AXL Antibodies.

| cell line | | F107-7H5-DM1 | F107-8D12-DM1 | F107-10G1-DM1 | F111-3C8-DM1 | F111-5E9-DM1 | hIgG-DM1 |
|---|---|---|---|---|---|---|---|
| H292 | $IC_{50}$ (nM) | 0.113 | 0.176 | 0.044 | 0.419 | 0.159 | >10 |
| NSCLC | % max inh | 74.0 | 72.8 | 57.7 | 70.3 | 64.6 | incomplete |
| A549 | $IC_{50}$ (nM) | 0.120 | 0.218 | 0.058 | 0.313 | 0.169 | >10 |
| NSCLC | % max inh | 58.5 | 61.8 | 55.7 | 71.2 | 70.0 | incomplete |
| 231 | $IC_{50}$ (nM) | 0.037 | 0.056 | ~0.029 | 0.147 | 0.067 | >10 |
| TNBC | % max inh | 71.4 | 73.4 | 64.9 | 77 | 69.2 | incomplete |
| HaCaT | $IC_{50}$ (nM) | no effect | no effect | no effect | no effect | no effect | no effect |
| | % max inh | incomplete | incomplete | incomplete | incomplete | incomplete | incomplete |

Example 5: Cell Surface Binding by Flow Cytometry

The binding properties of the anti-hAXL-ECD monoclonal antibodies purified in Example 1 to AXL on cell surfaces were evaluated by flow cytometry using the H292 cell line, due to its strong inhibition by the anti-hAXL-ECD mAb (see Example 2).

Detection of antibody binding to surface AXL by flow cytometry. Prior to analysis, cells were plated such that they were not more than 80% confluent on the day of analysis. Cells were washed in PBS and harvested by the addition of cell dissociation buffer (Sigma). A cell suspension containing 2.5×10$^5$ cells (in 500 µl corresponding cell culture media) was incubated with various concentrations (0.01-10 nM) of anti-AXL antibodies for 2 h at 4° C. (to prevent internalization). Following one wash with cell culture media, primary antibody was incubated with 2 µg DYLIGHT™ 488 conjugated AffiniPure goat anti-mouse IgG Alexa 488 secondary antibody (Jackson ImmunoResearch) in 100 µl of media for 1 h at 4° C. Prior to analysis, cell pellets were re-suspended in 300-500 µl media and filtered through a 50 µm nylon mesh filter to remove cell aggregates. Flow cytometry analyses were performed on 10,000 viable cells gated on forward scattering, side scattering parameters and propidium iodide dye exclusion using a BD LSRII flow Cytometer (Becton-Dickinson Biosciences, CA, USA) and a standard filter set using BD FACSDiva™ acquisition software, according to manufacturer's instructions.

Specific detection of antibody binding was calculated as the mean fluorescent intensity of binding to each primary antibody after background level subtraction of the mean fluorescent intensity of binding in the absence of primary antibody (but containing detection antibody). Binding parameters Bmax, (maximum fluorescence signal at receptor saturation), and KD (apparent cell binding constant) were then determined using a One site-Specific binding with Hill slope model in GraphPad Prism v 6.0.

Results are shown in FIG. 3 and Table 4. These results showed that mAb 7H5, 8D12, and 5E9 bound strongly (with an apparent binding constant, $K_D \leq 1$ nM) compared to the negative-binding control (300 nM mouse IgG).

Table 4 provides binding properties of anti-AXL mAb to cell-based AXL on H292 cells.

TABLE 4

Binding Properties of Anti-AXL mAb to Cell-based AXL on H292 Cells

| Best-fit values | F107-8D12 | F107-7H5 | F111-3C8 | F107-10G1 | F111-5E9 |
|---|---|---|---|---|---|
| Bmax (MFI) | 1309 | 1431 | 1477 | 937 | 1149 |
| Kd (nM) | 0.08802 | 0.1038 | 1.227 | 0.1005 | 0.1767 |

Example 6: Epitope Binning Experiments

To evaluate whether anti-hAXL-ECD mAb of Example 1 bind to the same epitope region, surface plasmon resonance epitope binning experiments were carried out.

Antibodies were directly immobilized on the chips surface ('mAb1'), after which the rhAXL ECD was flowed, followed by flowing the same or a different antibody ('mAb2'). All experiments were performed on a ProteOn XPR36 biosensor at 25° C. using PBST as running buffer (PBS with 0.05% v/v Tween20). GLM sensor chips and coupling reagents (10 mM sodium acetate, pH 4.5, sulfo-N-hydroxysuccinimide (SNHS), 1-ethyl-3-(3-dimethylaminporpyl)-carbodiamide hydrochloride (EDC), and ethanolamide) were purchased from BioRad, Inc (Hercules, Calif.).

Creating the antibody array. Antibodies (Mab1) were immobilized on the GLM chip surface at 30 µl/min. The activation reagents (at stock concentration of 0.4M EDC and 0.1M SNHS in water) were diluted 20-fold each in water. The top (A1) horizontal channel (the Analyte channel in the Proteon control software) was activated for 3 min with the diluted activation reagents. Next, the mAb (Example 1) were each diluted to 20 µg/ml in 10 mM acetate pH4.5 and injected for 3 min in separate vertical (L1 to L6) channels (the Ligand channel in the Proteon control software), followed with a 3 min injection of ethanolamine to block the reactive spots. The multi-channel module (MCM) was then rotated and another 3 min injection of ethanolamine was done on the activated horizontal channel (A1). This four-step 'activation-binding-and-2× deactivation' procedure was then repeated on each of the horizontal channels (A2 to A6).

Sandwich epitope binning. The two-step sandwich epitope binning was done at 30 µl/min in the analyte orientation. 100 nM rhAXL-ECD protein was injected for 3 min, immediately followed by a 3 min injection of mAb2 at 100 nM. Immobilized mAb (mAb1) surfaces were regenerated by a 18 s injection of 0.85% phosphoric acid at 100 µl/min. This two-step injection (rhAXL-ECD-mAb2) was repeated for each individual mAb2. Each mAb was also tested simultaneously as mAb1 (immobilized on the chip) and mAb2 (in solution). To monitor the AXL dissociation from the immobilized mAb1 PBST was injected instead of mAb2.

Table 5 provides epitope binning results for mAb. Cells labelled "nc" indicate no competition, "sc" cells indicate self-competition, and "C" cells indicate competition.

TABLE 5

Epitope Binning Results for mAb

|  | F107-8d12 | F107-7H5 | F111-3C8 | F111-5E9 | F107-10G1 |
|---|---|---|---|---|---|
| F107-8D12 | sc | C | nc | nc | nc |
| F107-7H5 | C | sc | nc | nc | nc |
| F111-3C8 | nc | nc | sc | C | nc |
| F111-5E9 | nc | nc | C | sc | nc |
| F107-10G1 | nc | nc | nc | nc | sc |

From the results shown in Table 5, it can be seen that four of the mAb fall into 2 epitope bins, that is, they compete with each other for binding to AXL; 7H5 competes with 8D12 and vice versa, and 3C8 competes with 5E9 and vice versa. 10G1 does not compete with the other mAbs. In contrast, anti-AXL mAb that were not selected based on their ability to internalize in the ADC surrogate assay tended to distribute themselves into a larger number of bins (data not shown). This data suggests that functional selection for internalizing antibodies results in a subset that bind selectively to 3 major sites on AXL extracellular domain. Moreover, additional SPR binding studies using similar methods demonstrated that these sites correspond to regions within Immunoglobulin-like domain-1 and -2. Epitope binning experiments (same methods as above) performed with the individual AXL extracellular subdomain (Immunoglobulin-like domain or Fibronectin type III-like domain) showed that mAb F107-10G1 binds a sequence in Immunoglobulin-like domain-1, and that it failed to compete with all other IgL1-binding antibodies tested, consistent with the results utilizing the full AXL ectodomain. These results indicate that there are at least 2 separate epitopes within Immunoglobulin-like domain-1 with which ADC mAbs interact.

Example 7: Epitope Mapping by Yeast Surface Display

Yeast surface display was used to map the sequences to which the anti-hAXL-ECD mAb of Example 1 bind.

Epitope mapping. The hAXL ectodomain (ECD) and its fragments were expressed and covalently displayed on the surface of yeast cells using the yeast surface display method (Feldhaus et al., 2003). The YSD vector (pPNL6) was from The Pacific Northwest National Laboratory, USA. The hAXL fragments covering the entire hAXL-ECD (FIG. 5) were expressed as fusion proteins (Aga2-HA-(hAXL)-MYC on the yeast cell surface. The displayed hAXL fragments were used to map the domains of hAXL to which the anti-hAXL-ECD mAb of Example 1 bind. The binding of the mAb to yeast cells was performed using a whole yeast cell ELISA. The relative amount of the displayed fusion protein was measured by probing with an anti-MYC antibody, followed by an HRP-conjugated secondary antibody, and used to normalize the binding signal for the mAb of Example 1.

Figure 5:
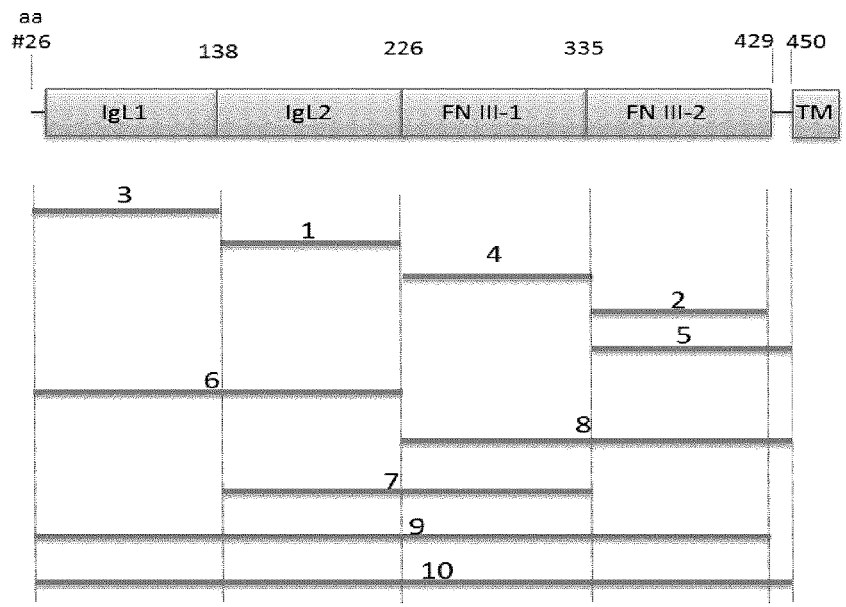
FIG. 5 is a schematic representation of the human AXL protein ectodomain (hAXL-ECD) and transmembrane domain. Domain binding is shown for ten peptide fragments of the hAXL-ECD.

FIG. 5 is a schematic representation of the human AXL ectodomain and transmembrane domain. Ten peptides covering the entire hAXL-ECD were expressed on the yeast membrane to map the binding epitope of the anti-AXL mAb. The peptides are represented and numbered 1 to 10.

Table 6 shows the results of anti-AXL mAb binding to various regions in the AXL extracellular domain on displayed yeast cells. The mAb of Example 1 binds two regions: either the Immunoglobulin-like domain 1 (IgL1, corresponding to aa 26-138) or the Immunoglobulin-like domain 2 (IgL2, corresponding to aa 135-226). These results are consistent with the results obtained in Example 6.

TABLE 6

Results of anti-AXL mAb Binding to Various Regions in the AXL Extracellular Domain

| mAb | Epitope location | Epitope conformation |
| --- | --- | --- |
| F107-7H5 | IgL1 | Conformational |
| F107-8D12 | IgL1 | Conformational |
| F111-5E9 | IgL2 | Conformational |
| F111-3C8 | IgL2 | Conformational |
| F107-10G1 | IgL1 | Conformational |

The nature of the epitopes. To determine if the epitopes for the mAb are continuous (linear) or non-continuous (conformational), various fragments of either IgL1 or IgL2 domains were expressed and displayed on yeast cells and assayed for binding to the mAb using cell ELISA as described above. None of the sub-fragments of either IgL domains binds significantly to any mAb of Example 1, although these sub-fragments displayed well on the surface of the yeast cell as judged by the signal of the anti-MYC signal. These results strongly suggest that the epitopes for the mAb of Example 1 require the entire sequence information of the IgL domain, and therefore are largely conformational.

Example 8: Antibody Sequencing

The VH and VL domains of the anti-hAXL mAb of Example 1 were sequenced and analyzed.

Sequences of the VH and VL domains as well as the CDR regions are shown in Table 7. Analysis of the sequence for a consensus binding sequence of the CDR 1-3 regions of the VH and VL chains was conducted using web-based software. The results of this analysis indicated that the CDR regions of both the VH and VL regions of mAb F107-7H5 is very similar to that of F107-8D12 (2 amino acid change). These antibodies cluster together and recognize a common linear epitope within IgL1. In contrast, the remainder of the antibodies tend to form smaller differentiated clusters, the majority of which bind IgL2, with the exception of F107-10G1 (which bind a site on IgL1 which is distinct from the majority of the IgL1 binding antibodies selected).

TABLE 7

CDR Sequences for mAb F107-7H5, F107-8D12, F111-5E9, F111-3C8, and F107-10G1

| mAb | | Light Chain CDR | | Heavy Chain CDR |
| --- | --- | --- | --- | --- |
| F107-7H5 | $V_L$ L1 | SEQ ID NO: 38 KSSQSLLNSRTRKIYLA (SEQ ID NO: 9) | $V_H$ H1 | SEQ ID NO: 39 GYTFTSYWIN (SEQ ID NO: 12) |
| | L2 | WASTRQS (SEQ ID NO: 10) | H2 | NIYPDSSSTNYNEKF KS (SEQ ID NO: 13) |
| | L3 | KQSYNLWT (SEQ ID NO: 11) | H3 | DTYGGSPDY (SEQ ID NO: 14) |
| F107-8D12 | $V_L$ L1 | SEQ ID NO: 40 KSSQSLLNTRTRKNYLA (SEQ ID NO: 15) | $V_H$ H1 | SEQ ID NO: 41 GYTFISFWIN (SEQ ID NO: 17) |
| | L2 | WASTRES (SEQ ID NO: 16) | H2 | NIFPGSSSTNYNEKF KS (SEQ ID NO: 18) |
| | L3 | KQSYNLWT (SEQ ID NO: 11) | H3 | DYYGGSPDY (SEQ ID NO: 19) |
| F111-3C8 | $V_L$ L1 | SEQ ID NO: 42 SASSSVSYMY (SEQ ID NO: 26) | $V_H$ H1 | SEQ ID NO: 43 GYTFTSYWMH (SEQ ID NO: 29) |
| | L2 | RTSNLAS (SEQ ID NO: 27) | H2 | NINPNSTSADYNEKF KR (SEQ ID NO: 30) |
| | L3 | QQYHNYPPT (SEQ ID NO: 28) | H3 | PLMGPYWYFDV (SEQ ID NO: 31) |
| F111-5E9 | $V_L$ L1 | SEQ ID NO: 44 RASQDINNYLN (SEQ ID NO: 20) | $V_H$ H1 | SEQ ID NO: 45 KYGMN (SEQ ID NO: 23) |
| | L2 | YISRLHS (SEQ ID NO: 21) | H2 | WINTYTGEPTYADDF KG (SEQ ID NO: 24) |
| | L3 | QQGNTLPFT (SEQ ID NO: 22) | H3 | GGYYSNPIYPMDY (SEQ ID NO: 25) |
| F107-10G1 | $V_L$ L1 | SEQ ID NO: 46 KASQDVTTAVA (SEQ ID NO: 32) | $V_H$ H1 | SEQ ID NO: 47 NYGMS (SEQ ID NO: 35) |
| | L2 | WASTRHT (SEQ ID NO: 33) | H2 | SISGGGGRTYYLDNV KG (SEQ ID NO: 36) |
| | L3 | QQHFTTPLT (SEQ ID NO: 34) | H3 | GARASYFAMDY (SEQ ID NO: 37) |

Example 9: Recombinant Antibody Production and Purification

To facilitate large scale mAb productions and consistency between productions, the anti-hAXL-ECD mAb identified in Example 8 were produced recombinantly in CHO cells.

The VH and VL regions (see Example 8) were cloned as fusions with human IgG1 constant regions (human IgG1 heavy chain and human kappa light chain, respectively) into the pTT5 vector, thereby generating chimeric mAb.

Table 8 provides sequences for each of the chimeric mAbs: hFC-F107-7H5, hFC-F107-8D12, hFC-F111-5E9, hFC-F111-3C8, and hFC-F107-10G1. In addition, all light chain sequences comprised a signal sequence MVLQTQVFISLLLWISGAYG (SEQ ID NO:59) at the N-terminus, while heavy chain sequences comprised the signal sequence MDWTWRILFLVAAATGTHA (SEQ ID NO:60) at the N-terminus.

TABLE 8

Sequences of Chimerized mAb

| mAb | Sequence |
| --- | --- |
| hFC-F107-7H5 light chain | SEQ ID NO: 48 |
| hFC-F107-7H5 heavy chain | SEQ ID NO: 49 |
| hFC-F107-8D12 light chain | SEQ ID NO: 50 |
| hFC-F107-8D12 heavy chain | SEQ ID NO: 51 |
| hFC-F111-3C8 light chain | SEQ ID NO: 52 |
| hFC-F111-3C8 heavy chain | SEQ ID NO: 53 |
| hFC-F111-5E9 light chain | SEQ ID NO: 54 |
| hFC-F111-5E9 heavy chain | SEQ ID NO: 55 |
| hFC-F107-10G1 light chain | SEQ ID NO: 56 |
| hFC-F107-10G1 heavy chain | SEQ ID NO: 57 |

Chimeric mAb expression was validated via a 2 mL expression scout: CHO cells were transiently transfected with VL and VH containing constructs (1:1 ratio); conditioned medium (CM) was harvested on day 7, and mAb expression levels were evaluated by SDS-PAGE (data not shown). The chimeric mAb expressed well and a small-scale production (50 mL) was initiated by transiently transfecting CHO cells with the same construct ratio. Conditioned medium (CM) was harvested on day 7, chimeric mAb were purified (ProtA), quantitated, and evaluated by SDS-PAGE. The data showed that all five chimeric mAb were well expressed by the transiently transfected CHO cells.

To confirm that the recombinantly expressed chimeric mAb behave similarly to the hybridoma-expressed mAb, SPR binding experiments are performed to ensure that AXL binding is not compromised.

Example 10: Isolation of Anti-AXL mAbs and sdAbs

In this example, isolation of llama sdAbs directed against human AXL ectodomain is conducted.

Materials and Methods

Production of recombinant human AXL ectodomain (rhAXL ECD). A mammalian expression vector (pTT5) containing a synthetic recombinant fragment of C-terminally $His_8$-tagged recombinant human AXL extracellular domain was transiently transfected in CHO cells, purified by Ni-agarose and verified by SDS-PAGE (data not shown).

Llama Single Domain Antibody (sdAb) generation. Llama sdAbs (VHHs) were generated by immunizing a llama with rhAXL ECD protein followed by panning of a phage-displayed VHH library constructed from peripheral blood lymphocytes. Briefly, one llama (*Lama glama*) was immunized with 100 µg of rhAXL on days 0, 21, 28, 35 and 42. The antigen was mixed with Freund's complete adjuvant on day 0 and Freund's incomplete adjuvant on days 21, 28, 35 and 42. Serum was drawn before the first immunization of day 0 (pre-immune) as well as on days 35 and 49 then fractionated into separate conventional IgG (cIgG) from heavy-chain IgG (hcIgG) using protein A and protein G affinity chromatography. ELISA against rhAXL on unfractionated and fractionated sera was performed. Briefly, 1 µg of rhAXL diluted in PBS was coated overnight (100 µl/well, 18 h, 4° C.) in 96 well MAXISORP™ plates (Nalge Nunc International, Rochester, N.Y.). Plates were blocked with 5% skim milk/PBST, washed with PBS-T (PBS+0.05% (v/v) Tween 20), and serial dilutions of pre-immune total (unfractionated) serum, post-immune total serum (Day 35 and 49) and fractionated serum (Day 49; 100 µg/ml starting concentration) was applied. After incubation at room temperature for 1.5 h and washing with PBS-T, goat anti-llama IgG-HRP (1:10,000 in PBS) was added for 1 h at 37° C. A final PBS-T wash preceded the addition of 100 µl/well TMB substrate (KPL, Gaithersburg, Md.) for 10 min. The reaction was stopped with 100 µl/well 1 M H3PO4 and read on a BioRad plate reader (Hercules, Calif.) at 450 nm.

For phage-displayed VHH library construction, RNA was isolated from approximately $5 \times 10^7$ lymphocytes collected on Day 35 and 49 post-immunization using the QIAamp RNA Blood Mini Kit (QIAGEN, Mississauga, ON, Canada). Approximately 10 µg of total RNA was used as template for first strand cDNA synthesis with oligo dT primers using the First-Strand cDNA Synthesis Kit (GE Healthcare, Baie-d'Urfé, QC, Canada). The cDNA was PCR-amplified by an equimolar mix of three variable region-specific sense primers (MJ1, MJ2, and MJ3) and two antisense CH2-specific primers (CH2 and CH2b3). Briefly, the PCR reaction mixture was set up in a total volume of 50 µl with the following components: 5 µl cDNA, 5 pmol of MJ1-3 primer mixture, 5 pmol of either CH2 or CH2b3 primers, 5 µl of 10× reaction buffer, 1 µl of 10 mM dNTP and 2.5 units of PLATINUM® Taq DNA polymerase (Invitrogen/Life Technologies, Burlington, ON, Canada). The PCR protocol consisted of an initial step at 94° C. for 3 min, followed by 30 cycles of 94° C. for 30 s, 57° C. for 45 s, 72° C. for 1 min and a final extension step at 72° C. for 10 min. The amplified PCR products were run in a 2% agarose gel and two major bands were observed: a band of about 850 bp, corresponding to conventional IgG, and a second band of around 600 bp, corresponding to heavy-chain antibodies (hcIgGs). The smaller bands were cut and purified using the QIAquick Gel Extraction Kit (QIAGEN) and re-amplified in a second PCR in a total volume of 50 µl using 1 µl of DNA template, 5 pmol of each of MJ7 primer and MJ8 primer, 5 µl of 10× reaction buffer, 1 µl of 10 mM dNTP and 2.5 units of Platinum® Taq DNA polymerase. The PCR protocol consisted of an initial step at 94° C. for 3 min, followed by 30 cycles of 94° C. for 30 s, 57° C. for 30 s and 72° C. for 1 min and a final extension step at 72° C. for 7 min. The amplified PCR products, ranging between 340 bp and 420 bp and corresponding to VHH fragments of hcIgGs, were purified using the QIAquick PCR Purification Kit (QIAGEN), digested with SfiI restriction enzyme (New England BioLabs, Pickering, ON, Canada) and re-purified using the same kit. Fifty micrograms of pMED1 phagemid was digested with SfiI overnight at 50° C.

To minimize self-ligation, 20 units of XhoI and PstI restriction enzymes were added and the digestion reaction was incubated for an additional 2 h at 37° C. Twenty micrograms of digested phagemid DNA was ligated with 6 µg of digested VHH fragments for 3 h at room temperature using T4 DNA ligase (Invitrogen) and its protocol. The ligated materials were purified using the QIAquick PCR Purification Kit in a final volume of 100 µl and electroporated in 5 µl portions into commercial electrocompetent TG1

E. coli cells (Stratagene, La Jolla, Calif.) as described. The size of the library was determined as described. The library was grown for 2 h at 37° C., 250 rpm in the presence of 2% (w/v) glucose. The bacterial cells were pelleted, re-suspended in 2xYT/Amp/Glu (2×YT medium with 100 µg/ml ampicillin and 2% (w/v) glucose) with 35% (v/v) glycerol and stored at −80° C. in small aliquots.

The phage-displayed library was rescued using M13K07 helper phage. AXL-specific VHHs were selected from the library using two strategies. In the first strategy, the library was panned simultaneously against immobilized rhAXL ECD and against A549 tumor cells as described in Zhou et al., 2010. In the second strategy, the library was panned against rhAXL ECD and VHH-displaying phage were eluted competitively with AXL-specific murine mAbs (5E9 and 10G1) as described in Henry et al., 2016. The library phage and the phage eluted from pannings were interrogated using Illumina MiSeq next-generation DNA sequencing as described in Henry et al., 2016.

Results

VHHs directed against rhAXL ECD were identified by constructing a phage-displayed VHH library from an immunized llama and performing various selections of the library as described in methods section, above. The input (library) VHH-displaying phage and the output (eluted) VHH-displaying phage were sequenced, and individual VHH sequences selectively enriched in particular selections were identified.

Figure 6:
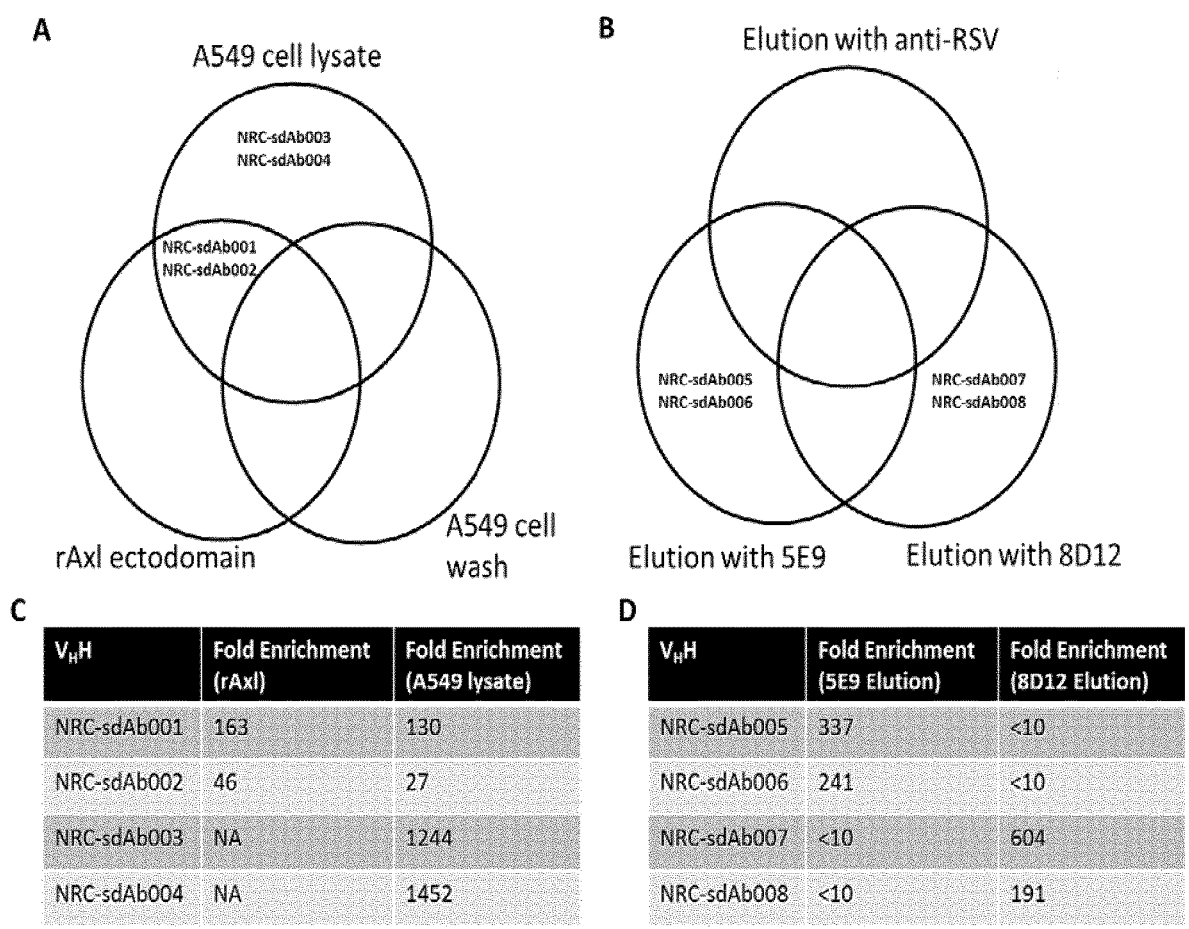
FIG. 6 is a schematic representation of the strategy for isolation of anti-rhAXL ECD single domain antibodies (sdAbs).

FIG. 6 illustrates the strategy for isolation of anti-rhAXL ECD sdAbs. In panels A and C, the phage-displayed VHH library constructed from a llama immunized with rhAXL-ECD was panned simultaneously on immobilized rhAXL and on AXL+A549 tumour cells. VHHs simultaneously enriched for binding to rhAXL ECD and internalization into A549 cells (NRC-sdAb001, SEQ ID NO:119; NRC-sdAb002, SEQ ID NO:120) as well as VHHs enriched only for internalization into A549 cells (NRC-sdAb003, SEQ ID NO:121; NRC-sdAb004, SEQ ID NO:122) were identified. In panels B and D, the phage-displayed VHH library constructed from a llama immunized with rhAXL-ECD was panned against rhAXL ECD and VHHs competitively eluted using AXL-specific mAbs 5E9 or 8D12. VHHs enriched using this selection strategy were identified using next-generation DNA sequencing.

Example 11: Determination of DNA and Amino Acid Sequences of Anti-AXL mAbs and sdAbs In this example the DNA and amino acid sequences of anti-AXL mAbs and sdAbs (isolated according to Example 10) are described.

Materials and Methods

For murine mAb sequencing, total RNA was extracted from hybridoma clones (Qiagen, RNEasy) and reverse transcribed into cDNA (SuperScript™, ThermoFisher Scientific, Waltham, Mass., USA). DNA encoding VH and VL domains was PCR amplified (Platinum Taq or equivalent) using mixtures of degenerate forward primers annealing in FR1 and a single reverse primer annealing in CH1 (Novagen/EMD Millipore cat. no 69831-3). The resulting amplicons were subcloned (TOPO-TA) and sequenced using the Sanger method on an ABI 3730xl instrument.

For determination of llama VHH DNA sequences, a phage-displayed VHH library was subjected to a variety of in vitro selections (described in Example 10) and sequenced using 2×250 bp reads on an Illumina MiSeq instrument. VHH sequences of interest were identified by increased frequency post-selection compared to prior. DNA constructs encoding VHHs were synthesized commercially (Geneart, Life Technologies) and subcloned into a bacterial expression vector, then confirmed again using the Sanger method on an ABI 3730xl instrument.

Results

The DNA sequences of the VH and VL domains of seven murine mAbs were determined by Sanger sequencing of amplicons derived from hybridoma cells. DNA constructs encoding the mAb VH/VL domains were synthesized commercially in mammalian expression vectors containing fragment crystallizable regions (Fc regions) and verified by Sanger sequencing.

FIG. 7 shows amino acid sequences of the mAb VH/VL domains with CDRs using International ImMunoGeneTics (IMGT) information system definitions represented in bold underlined font. IMGT definitions are used when referencing CDR sequences herein. Kabat definitions of CDRs are shown as shaded font in FIG. 7, as an alternative definition to IMGT, primarily for interest only. IMGT definitions of CDRs may include slightly more N-terminal sequence, while Kabat definitions show CDRs as starting later and extending further C-terminally.

The DNA sequences of eight llama VHHs were determined using 2×250 bp reads on an Illumina MiSeq instrument (sequences were determined as part of the isolation of these VHHs, as described in Example 10). DNA constructs encoding the VHHs were synthesized commercially (GeneArt, Life Technologies) in a bacterial expression vector and their sequences were confirmed using Sanger sequencing.

FIG. 8 shows amino acid sequences of the VHHs with CDRs, using IMGT definitions, represented in bold underlined font. IMGT definitions are used when referencing CDR sequences herein. Kabat definitions of CDRs are shown in shaded font in FIG. 8, as an alternative to IMGT. Sequences referenced as NRC-sdAb001 to NRC-sdAb008 are shown.

Example 12: Binding of mAbs and sdAbs to Recombinant AXL Extracellular Domain (ECD)

The purpose of this Example is to characterize binding of mAbs/sdAbs to recombinant AXL extracellular domain (ECD), evaluating affinity and kinetics, species cross-reactivity, and domain and epitope mapping.

Materials and Methods

Production of murine mAbs. Murine mAbs were either purified directly from hybridoma supernatant or produced recombinantly (with human IgG1 Fc regions) by transient transfection of CHO cells. For small-scale purification from 10 mL hybridoma supernatant, mAbs were purified via adsorption onto Protein G Mag Sepharose™ Extra (GE Healthcare Life 20 Sciences #28-9670-70), washed in PBS, eluted twice with 200 µl of glycine 200 mM pH 2.5 and neutralized in TRIS-HCl 1M pH 9.0. Purified mAbs were desalted using Zeba Spin resin (Pierce) pre-equilibrated in PBS and filter sterilized through 0.22 µM membrane (Millipore). The final concentration of the mAbs was determined by nano-drop (#ND-1000). For recombinant production, DNA constructs were transiently transfected in CHO cells and purified as described in Raymond et al. (2015).

Production of VHHs and VHH-Fcs. VHHs were produced as 6xHis- and Myc-tagged monomers in E. coli as described previously by Baral et al. (2013). VHH-Fcs were produced by transient transfection of HEK293 cells with DNA encoding VHHs fused N-terminally to human IgG1 Fc as described in Zhang et al., 2009.

Surface plasmon resonance. For murine mAbs, binding to human and cynomolgus AXL ECD was assessed using a Biacore T200 instrument. Briefly, either anti-mouse or anti-human Fc antibody was immobilized on a research-grade CM5 series S sensor chip using amine coupling in acetate buffer. Murine or recombinant chimeric murine-human mAbs (mouse VH/VL; human constant regions) were captured, then recombinant human or cyno AXL ECD was flowed over the surface at different concentration ranges (0.1-500 nM) depending on the antibody. The running buffer was PBS/Tween-20 and the flow rate 100 uL/min. All binding studies were performed at 25° C. Surfaces were regenerated using 10 mM glycine, pH 1.5.

For VHHs and VHH-Fcs, binding to human and cynomolgus AXL ECD was assessed using either a Biacore T200 instrument or a Biacore 3000 instrument. Either human AXL ECD or anti-human Fc antibody was immobilized on a research-grade CM5 series S sensor chip (T200, rhAXL ECD) or a C1 sensor chip (3000, anti-human Fc) using amine coupling in acetate buffer. VHH-Fcs were captured on anti-human Fc surfaces. Either monomeric VHHs (for rhAXL ECD surfaces) or human and cyno AXL ECD (for VHH-Fc surfaces) were flowed over the surfaces at different concentration ranges. Running buffers were HBS-EP (3000) and HBS-EP+ (T200). Flow rates were 10-40 ul/min. All binding studies were performed at 25° C. Surfaces were regenerated using 10 mM glycine, pH 1.5.

For epitope binning experiments, two test articles (VHH or mAb) were first injected separately (50 nM mAb; 25-fold $K_D$ for VHH monomer) and allowed to dissociate. The mAb (50 nM) was then injected again and at the peak of the response, a mixture of VHH (25-fold $K_D$) and mAb (50 nM) was injected to observe any additional binding.

ELISA. ELISAs against human, cyno and mouse AXL ECDs were conducted by immobilizing 100 ng of each protein in wells of Nunc MaxiSorp microplates overnight. Human AXL (aa 1-451) and cyno AXL (aa 1-449) were produced recombinantly as described in Example 10. Mouse AXL was purchased from Sino (cat. 51026-M08H). The next day, plates were blocked with 5% (w/v) dried milk in PBS. Murine mAbs (either hybridoma- or recombinantly-produced) or VHH-Fcs were diluted in PBS containing 1% BSA and 0.1% Tween-20 and added to wells for 2 hours at room temperature. Wells were washed 5× with PBS containing 0.1% Tween-20, then HRP-labeled protein A (diluted 1:1000 in PBS containing 1% BSA and 0.1% Tween™-20) was added to wells for 1 hour at room temperature. Wells were washed again 5× with PBS/0.1% Tween-20 and developed using TMB substrate. Absorbance was measured at 450 nm. As a positive control for mouse AXL binding, a commercial anti-mouse AXL mAb (clone 175128, R&D Systems MAB8541, rat IgG2A) was used and detected with donkey anti-mouse:HRP secondary antibody.

Yeast surface display. Yeast surface display of human AXL, Tyro3 and Mer extracellular domains was conducted. Briefly, yeast were transformed with DNA constructs encoding myc-tagged TAM-family RTK ectodomains fused to Aga2p protein. Constructs were designed to encode complete AXL ECD (aa 1-449) or individual subdomains (Ig1, Ig2, Fn1, Fn2 from N- to C-terminal). For fine epitope mapping, individual amino acids of AXL ECD were substituted with Ala in the constructs. The resulting yeast cells expressing partial or complete AXL, Tyro3 and Mer extracellular domains were adsorbed in microwell plates and binding of mAbs/VHH-Fcs were assessed by ELISA and detected using goat anti-human F(ab')$_2$-HRP. Anti-AXL mAb/VHH-Fc binding were normalized to binding levels of an anti-myc antibody to control for expression level.

Results

Binding of murine mAbs to human and cyno AXL ECD was assessed in SPR using chimeric murine-human mAbs produced recombinantly. Binding of llama VHHs to human and cyno AXL ECD was assessed in SPR using both monomeric VHHs and chimeric recombinant VHH-hIgG1 Fc fusions.

Affinity determination by SPR. Affinities and kinetics of murine mAbs for recombinant human and cynomolgus AXL ECD are shown in Table 9.

TABLE 9

Affinities and kinetics of mAbs for recombinant human and cynomolgus AXL ECD

| | Human AXL | | | Cyno AXL | | |
|---|---|---|---|---|---|---|
| mAb | $k_{on}$ (M$^{-1}$s$^{-1}$) | $k_{off}$ (s$^{-1}$) | $K_D$ (nM) | $k_{on}$ (M$^{-1}$s$^{-1}$) | $k_{off}$ (s$^{-1}$) | $K_D$ (nM) |
| mAb F107-10G1 | 1.1 × 10$^6$ [a] | 5.9 × 10$^{-4}$ [b] | 0.5 [a] | 8.2 × 10$^5$ [a] | 4.3 × 10$^{-4}$ [a] | 0.5 [a] |
| | 1.2 × 10$^6$ [b] | 5.6 × 10$^{-4}$ [b] | 0.4 [b] | 1.8 × 10$^6$ [b] | 2.3 × 10$^{-4}$ [b] | 0.2 [b] |
| mAb F111-5E9 | 7.8 × 10$^5$ [a] | 1.8 × 10$^{-3}$ [a] | 2 [a] | 6.9 × 10$^5$ [a] | 2.7 × 10$^{-3}$ [a] | 4 [a] |
| mAb F107-8D12 | 2.7 × 10$^6$ [a] | 1.3 × 10$^{-2}$ [a] | 5 [a] | — | — | 1835 [c] |
| mAb F107-7H5 | 1.4 × 10$^6$ | 1.5 × 10$^{-3}$ | 1 [a] | — | — | 925 [c] |
| mIgG2 F155-3C7 | 5.6 × 10$^5$ [b] | 1.8 × 10$^{-3}$ [b] | 3 [b] | 2.9 × 10$^5$ [b] | 7.3 × 10$^{-3}$ | 25 [b] |
| mAb F111-3C8 | 8.6 × 10$^4$ [a] | 1.0 × 10$^{-3}$ [a] | 12 [a] | 6.0 × 10$^4$ | 1.1 × 10$^{-3}$ | 18 [a] |
| mIgG2 F149-4G4 | 7.5 × 10$^5$ [b] | 1.2 × 10$^{-3}$ [b] | 1 [b] | — | — | >160 [b] |

[a] Measured using single-cycle kinetics
[b] Measured using multi-cycle kinetics
[c] Measured using steady-state analysis The data in Table 10 indicate affinities and kinetics of llama VHHs for recombinant human and cynomolgus AXL extracellular domain (ECD).

TABLE 10

Affinities and kinetics of llama VHHS for recombinant human and cynomolgus AXL ECD

| | Human AXL | | | Cyno AXL | | |
|---|---|---|---|---|---|---|
| sdAb | $k_{on}$ ($M^{-1}s^{-1}$) | $k_{off}$ ($s^{-1}$) | $K_d$ (nM) | $k_{on}$ ($M^{-1}s^{-1}$) | $k_{off}$ ($s^{-1}$) | $K_d$ (nM) |
| NRC-sdAb001 | $8.5 \times 10^{6}$ [a] | $3.7 \times 10^{-2}$ [a] | 4 [a] | | | |
| | $1.3 \times 10^{6}$ [c] | $7.2 \times 10^{-3}$ [c] | 6 [c] | $9.2 \times 10^{5}$ [c] | $7.2 \times 10^{-3}$ [c] | 8 [c] |
| NRC-sdAb002 | — | — | 96 [e] | nd | nd | nd |
| NRC-sdAb003 | $8.5 \times 10^{3}$ [a] | $5.4 \times 10^{-3}$ [a] | 955 [a] | nd | nd | nd |
| NRC-sdAb005 | $1.7 \times 10^{5}$ [b] | $9.7 \times 10^{-3}$ [b] | 58 [b] | $1.3 \times 10^{5}$ [c] | $4.6 \times 10^{-3}$ [c] | 35 [c] |
| | $1.2 \times 10^{5}$ [c] | $4.1 \times 10^{-3}$ [c] | 34 [c] | | | |
| NRC-sdAb006 | $2.4 \times 10^{5}$ [b] | $4.5 \times 10^{-3}$ [b] | 19 [b] | $1.0 \times 10^{5}$ [c] | $2.6 \times 10^{-3}$ [c] | 26 [c] |
| | $8.9 \times 10^{4}$ [c] | $2.1 \times 10^{-3}$ [c] | 24 [c] | | | |
| NRC-sdAb007 | — | — | >100 [c] | nd | nd | nd |
| NRC-sdAb008 | $3.3 \times 10^{6}$ [d] | $3.3 \times 10^{-3}$ [d] | 1 [d] | — | — | >200 [c] |
| | $5.3 \times 10^{6}$ [c] | $8.2 \times 10^{-3}$ [c] | 2 [c] | | | |

[a] Measured using single-cycle kinetics (immobilize AXL ECD, flow VHH monomer)
[b] Measured using multi-cycle kinetics (immobilize AXL ECD, flow VHH monomer)
[c] Estimated using single-concentration kinetics (capture VHH-Fc, flow AXL ECD)
[d] Measured using single-cycle kinetics (capture VHH-Fc, flow AXL ECD)
[e] Measured using steady-state analysis The cross-reactivity of cynomolgus and murine AXL was determined, and results shown below in Table 11. These data show half-maximal effective concentrations $EC_{50}$ for mAb/sdAb binding to recombinant human and mouse AXL ECD in ELISA.

TABLE 11

Half-maximal Effective Concentration for Binding ELISA

| mAb/sdAb | Human AXL (nM) | Mouse AXL (nM) |
|---|---|---|
| MAB8541 (R&D) | 61 | 1 |
| mAb F107-10G1 | 2 | n.b. |
| mAb F111- 5E9 | 2 | n.b. |
| mAb F107- 8D12 | 1 | n.b. |
| mAb F107- 7H5 | 6 | n.b. |
| mIgG2 F155- 3C7 | 14 | n.b. |
| mAb F111-3C8 | ND | ND |
| mIgG2 F149-4G4 | 15 | n.b. |
| NRC-sdAb001 | 1 | n.b. |
| NRC-sdAb002 | ND | ND |
| NRC-sdAb003 | ND | ND |
| NRC-sdAb005 | 1 | n.b. |
| NRC-sdAb006 | 1 | n.b. |
| NRC-sdAb007 | ND | ND |
| NRC-sdAb008 | 1 | n.b. | n.b., no binding;
ND, not determined

The determination of cross-reactivity to TAM family RTKs (Mer, Tyro3) using Yeast Surface Display was determined, and results are shown in Table 12.

TABLE 12

Cross-Reactivity to TAM using Yeast Surface Display

| | Goat anti-human F(ab')$_2$-HRP at ~1:5000 | | | | | |
|---|---|---|---|---|---|---|
| | hFC-107-10G1 | NRC-sdAb0001-Fc | NRC-sdAb0002-Fc | NRC-sdAb0003-Fc | hFC-anti-RSV | Anti-Myc-HRP myc |
| huAXL-ECD | 1.392 | 1.026 | 0.882 | 0.659 | 0.087 | 1.000 |
| cyAXL-ECD | 1.141 | 0.824 | 0.760 | 0.668 | −0.004 | 1.000 |
| huMER-ECD | −0.020 | −0.010 | 0.010 | −0.009 | −0.001 | 1.000 |
| huTyro3-ECD | −0.023 | 0.017 | −0.004 | −0.005 | 0.059 | 1.000 |
| pNL6 vector | −0.039 | −0.025 | 0.020 | −0.025 | −0.036 | 1.000 |
| Non-denatured yeast: normalized to myc expression level | | | | | | |

Epitope binning was assessed, and data are summarized in Table 13. Epitope bins targeted by anti-AXL mAbs/sdAbs are shown. Domain mapping using yeast surface display was evaluated.

TABLE 13

| mAb/sdAb | Domain | Epitope Bin |
|---|---|---|
| mAb F107-10G1 | Ig1 | 1A |
| mAb F111-5E9 | Ig2 | 2 |
| mAb F107- 8D12 | Ig1 | 1B |
| mAb F107- 7H5 | Ig1 | 1B |
| mIgG2 F155- 3C7 | ND | ND |
| mAb F111- 3C8 | Ig2 | ND |
| mIgG2 F149-4G4 | ND | ND |
| NRC-sdAb001 | ND (Ig1 based on binning) similar epitope to that of 10G1 based on binding competition | 1A |
| NRC-sdAb002 | ND | ND |
| NRC-sdAb003 | ND (Ig1 based on binning) | 1A |
| NRC-sdAb005 | ND (Ig2 based on binning) | 2 |
| NRC-sdAb006 | ND (Ig2 based on binning) | 2 |
| NRC-sdAb007 | ND (Ig1 based on binning) | 1B |
| NRC-sdAb008 | ND (Ig1 based on binning) | 1B |

Epitope bins targeted by Anti-AXL mAbs/sdAbs

Example 13: Characterization of Binding to Tumor Cell Lines

The purpose of this Example is to characterize binding of mAbs/sdAbs to tumor cell lines expressing moderate to high levels of AXL in terms of Kd, and maximum antibody binding (Bmax)

Materials and Methods

Cell culture. The NCI-H292 human non-small cell lung cancer (NSCLC) and the SKOV3 (human ovarian adenocarcinoma) cell lines were obtained from ATCC and cultured according to supplier's recommendations. The MDA-MB-231 triple negative (ER-/PR-/HER2low) breast cancer (TNBC) was purchased from Cedarlane Labs, Burlington N.C., USA. Stable transfectants with the firefly luciferase gene were generated. This cell line was cultured in RPMI-1640+5% FBS. U87 glioblastoma cells were used, as described above in Example 3. Cells were passaged twice a week and used within 4-6 weeks for all cell lines.

FACS binding assay. Adherent cells were dissociated with non-enzymatic Sigma Cell Dissociation Solution (Cat. No. C5789). Cells suspensions were added to polypropylene, V-bottom 96-well plates and incubated for 2 hours on ice with primary antibodies at concentrations ranging from 100 nM to 0.001 nM or at a single dose of 100 nM (for the non-specific control). After incubation and washes, cells were incubated with fluorescently labeled secondary antibody (Alexa Fluor® 488 anti-human IgG from Jackson Cat. No 709-546-098) for 1 hour on ice, then washed. Cell viability was determined using Fixable viability dye 450 (20 min on ice). Stained cells were fixed in 1% formaldehyde at 4° C. and stored at 4° C. until acquisition which was performed the next day.

Data acquisition was performed in the LSR-Fortessa Flow cytometer (Beckton Dickinson) equipped with FACS Diva Software and HTS unit (automated sampling in 96-well plates). FACS data was exported into Excel data files and MFI (Median Fluorescence intensity) of the AF488-stained, alive (single cells) peak was taken for calculations. Background subtraction was calculated for all wells using the MFI values of the cells incubated in the absence of secondary antibody.

Background subtracted data was analyzed in GraphPad™ 6.0 using the One-site specific binding with Hill slope non-linear regression curve fit model to determine apparent Bmax and Kd for each of the test articles. The model used was according to Formula I.

$$\text{Model } Y = \frac{Bmax \times X^h}{Kd^h + X^h} \quad \text{(Formula I)}$$

Bmax is the maximum specific binding, in the same unit as Y.

Kd is the ligand concentration needed to achieve half maximum binding at equilibrium, expressed in the same unit as X.

The variable "h" is the hill slope.

AXL receptor density measurements. 10 µl of Human AXL Alexa Fluor 488 MAb (Clone 108724) was used to label Quantum™ Simply Cellular Beads (Catalogue No. 814 from Bangs Laboratories, Fishers, Ind., USA) for 30 min at 4° C., or AXL expressing cell lines (100 000 cells/test) for 2 h at 4° C.

Data acquisition for beads and cells were performed under identical FACS settings and analysed using FlowJo™ software. The GeoMean was used to generate the standard curve and interpolate the values for each cell type. The blank beads value is considered as the detection threshold and the values of the unstained cells were subtracted from GeoMean values in each case. The resulting antibody binding capacity was used as a measure of receptor density for each of the cell lines tested.

Results

Binding of recombinant chimeric Abs to three cell lines was assessed by FACS as described above. The apparent Bmax and Kd determination is shown below in Table 14.

TABLE 14

Apparent Kd of human Fc containing mAbs in three AXL expressing cell lines

| Primary Ab | SKOV3 Kd (nM) | NCl-H292 Kd (nM) | MDA-MB-231 luciferase Kd (nM) |
|---|---|---|---|
| NRC-sdAb001 | 0.1122 | 0.1053 | 0.2327 |
| NRC-sdAb005 | 2.0330 | 1.4740 | 1.4720 |
| NRC-sdAb006 | 13.4300 | 2.1170 | 0.8317 |
| NRC-sdAb008 | 0.0549 | 0.0414 | 0.1216 |
| hIgG-F107-10G1 | 0.0608 | 0.0708 | 0.1012 |
| hIgG-F107-7H5 | 0.0700 | 0.0509 | 0.1696 |
| hIgG-F111-5E9 | ND* | ND* | 0.3659 |

*incomplete curve

Figure 9:
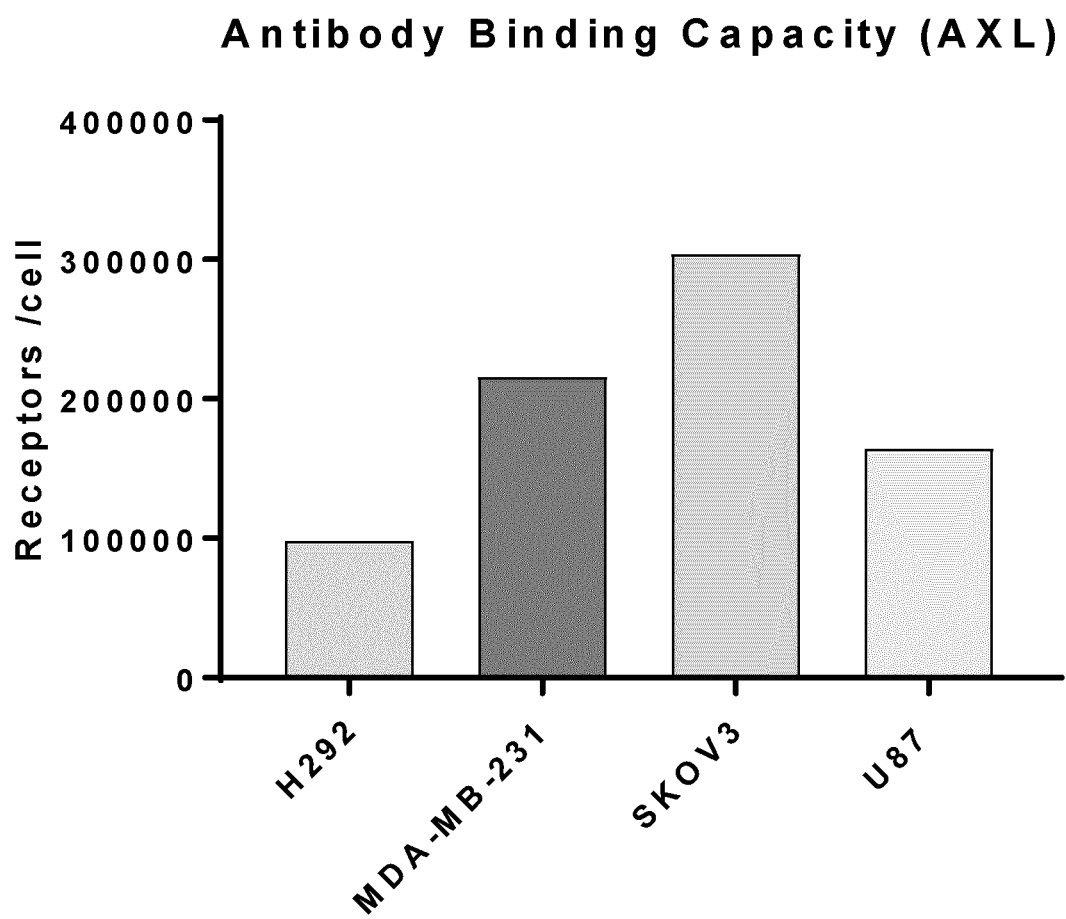
FIG. 9 shows antibody binding capacity in lung (H292), breast (MDA-MB-231), ovarian (SKOV3) and glioblastoma (U87) cell lines.

FIG. 9 illustrates Antibody Binding Capacity of AXL, based on receptor density (receptors/cell) in the following cell lines: H292, MDA-MB-231, SKOV, and U87 glioblastoma.

Figure 10:
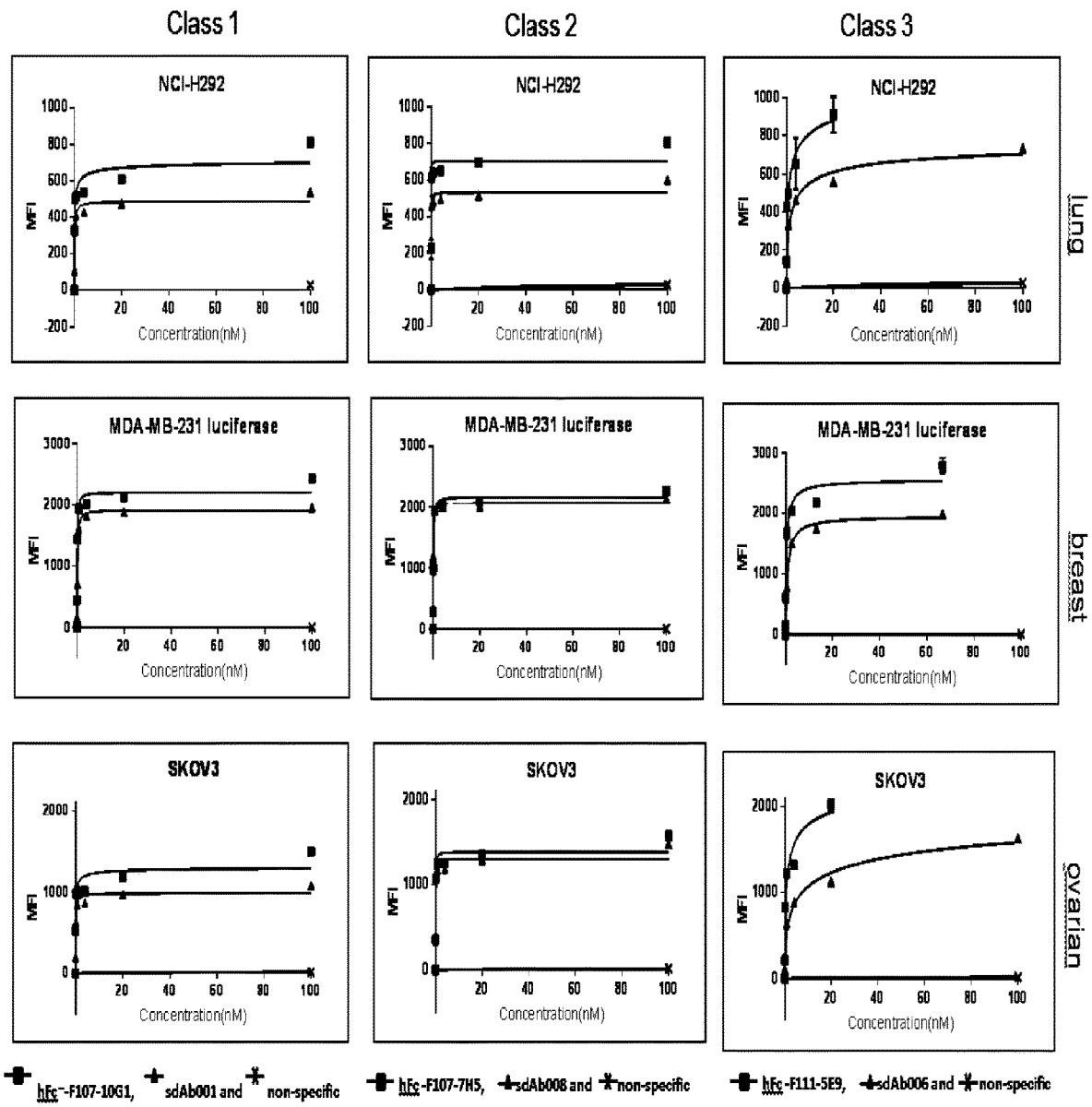
FIG. 10 shows the results of flow cytometry experiments determining the binding properties of anti-AXL hIgG and sdAbs in lung (NCI-H292), breast (MDA-MB-231), and ovarian (SKOV3) cell lines.

FIG. 10 illustrates FACS binding curves of human (h) IgG Abs and sdAbs in three cell lines for lung, breast and ovarian cancers. Non-specific binding (x), in all instances is shown are negligible while hIgG curve (F107-10G1, F107-7H5, F111-5E9) shows slightly higher mean of fluorescence intensity (MFI) than sdAbs (sdAB001, sdAb008, sdAb006) in some cases.

Example 14: In Vitro Cytotoxicity Assays

In this Example, anti-AXL monoclonal antibodies were evaluated for internalizing ability and antibody-drug conjugate (ADC) potential in a growth inhibition assay in AXL-expressing cells, in terms of potency ($IC_{50}$) and maximum percentage growth inhibition (efficacy).

Materials and Methods

Cell Culture. The NCI-H292 human non-small lung cancer (NSCLC) and the SKOV3 (human ovarian adenocarcinoma) cell lines were obtained from ATCC and cultured according to supplier's recommendations. The MDA-MB-231 triple negative (ER-/PR-/HER2low) breast cancer (TNBC) line was purchased from Cedarlane Labs. Stable transfectants with the firefly luciferase gene were generated by Perkin Elmer. This cell line was cultured in RPMI-1640+5% FBS. Cells were passaged twice a week and used within 4-6 weeks for all cell lines.

Growth Inhibition Assay. Anti-AXL ADCs were tested for their effects on viability on various cultured cell lines known to express AXL, including NCI-H292 (non-small cell lung cancer), MDA-MB-231 (human breast adenocarcinoma) and SKOV3 (ovarian carcinoma). Cells were seeded at 125, 200 and 200 cells/well for the three cell lines respectively in 384-well plates (Corning® 384 Well White Flat Bottom Polystyrene TC-Treated Microplates, Cat. #3570). Cells were allowed to grow for five days in the presence of serial dilutions of the test articles or benchmark controls ranging from 100 nM to 0.0017 nM and in the presence or absence of added Gas6 ligand (2 µg/mL, R&D CF885). After five days (37° C., 5% $CO_2$, humidified incubator), the number of viable cells in culture was determined using CellTiterGlo™ (Promega, Madison), based on quantitation of the ATP present in each well, which signals the presence of metabolically active cells.

Signal output was measured on a luminescence plate reader (Envision, Perkin Elmer) set at an integration time of 0.1 sec. Integration time is adjusted to minimize signal saturation at high ATP concentration.

Data analysis. Each concentration point (S) is normalized to the negative control wells (NC) and expressed as % survival, calculated according to Formula II.

$$\% \text{ survival} = \frac{NC - S}{NC \times 100} \qquad \text{(Formula II)}$$

Dose-response curves of % survival vs. log concentration were fit using GraphPad™ Prism 6.0 with a four parameter logistic model to estimate $IC_{50}$ and maximum efficacy. Model Y was used to calculations according to Formula III.

$$\text{Model } Y = \frac{\text{Bottom} + (\text{Top} - \text{Bottom})}{1 + 10^{(logIC50-X) \times HillSlope}} \qquad \text{(Formula III)}$$

$IC_{50}$ is the concentration of agonist that gives a response half way between Bottom and Top.

HillSlope describes the steepness of the curves.

Top and Bottom are plateaus in the units of the Y axis.

Results

Growth inhibiting activity of recombinant chimeric Abs conjugated to DM1 or MMAE in three cell lines was assessed as described above.

The cytotoxicity as direct drug conjugates was evaluated, as shown in Table 15. Potency ($IC_{50}$) and efficacy (% maximum inhibition) of anti AXL ADCs in three AXL expressing cell lines. Results are expressed as: average+/− stdev (N).

TABLE 15

Potency and efficacy of anti AXL ADCs in AXL expressing cell lines.

| | SKOV3 | | MDA-MB-231-luc | | NCI-H292 | |
|---|---|---|---|---|---|---|
| | $IC_{50}$ (nM) | % max inh | $IC_{50}$ (nM) | % max inh | $IC_{50}$ (nM) | % max inh |
| hFc-F111-5E9-VC-MMAE | 0.021 +/− 0.006 (2) | 75 +/− 3 (2) | 0.942 (1) | 105 (1) | ~1 (1) | incomplete curve (1) |
| hFc-F111-5E9-DM1 | 0.038 +/− 0.043 (3) | 73 +/− 7 (3) | 0.452 +/− 0.279 (6) | 82 +/− 20 (6) | 0.084 +/− 0.060 (9) | 78 +/− 9 (9) |
| hFc-sdAb005-DM1 | 0.631 +/− 0.202 (2) | 78 +/− 6 (2) | ND | ND | 6.664 +/− 1.718 (6) | 83 +/− 4 (6) |
| hFc-sdAb006-DM1 | 0.162 +/− 0.03 (2) | 76 +/− 6 (2) | 0.869 +/− 0.001 (2) | 83 +/− 2 (2) | 2.714 +/− 0.871 (2) | 87 +/− 13 (6) |
| hFc-F107-10G1-DM1 | 0.022 (1) | 66 (1) | 0.029 +/− 0.037 (2) | 62 +/− 9 (2) | 0.013 +/− 0.014 (4) | 71 +/− 5 (4) |
| hFc-sdAb001-DM1 | 0.055 +/− 0.006 (2) | 81 +/− 0 (2) | ND | ND | 0.887 +/− 0.218 (6) | 81 +/− 3 (6) |
| hFc-F107-7H5-DM1 | 0.014 +/− 0.019 (2) | 91 +/− 31 (2) | 0.076 +/− 0.079 (2) | 65 +/− 13 (2) | 0.014 +/− 0.026 (9) | 97 +/− 50 (9) |
| hFc-F107-8D12-DM1 | 0.001 (1) | 103 (1) | 0.033 (1) | 72. (1) | 0.011 +/− 0.006 (3) | 89 +/− 1 (3) |
| hFc-sdAb008-DM1 | ~0.001 | ~80 | ND | ND | 0.034 +/− 0.012 (6) | 83 +/− 8 (6) |
| mIgG-F155-3C7-DM1 | 0.092 (1) | 89 (1) | 0.630 (1) | 74 (1) | 0.327 +/− 0.098 (8) | 82 +/− 5 (8) |
| mIgG-F149-4G4-DM1 | 0.005 (1) | 90 (1) | 0.051 (1) | 64 (1) | 0.015 +/− 0.009 (8) | 79 +/− 4 (8) |

Assessment of Gas6 sensitivity. The potency ($IC_{50}$) of anti-AXL ADCs in NCI-H292 in the presence or absence of Gas6 ligand (2 µg/mL) was evaluated. Results are expressed in Table 16 as: average+/−stdev (N).

TABLE 16

Assessment of Gas6 Sensitivity

| | −Gas6 IC50 (nM) | +Gas6 IC50 (nM) |
|---|---|---|
| hFc-F111-5E9-VC-MMAE | ~1 (1) | ND |
| hFc-F111-5E9-DM1 | 0.084 +/− 0.060 (9) | 0.074 +/− 0.050 (2) |
| hFc-sdAb006-DM1 | 2.714 +/− 0.871 (2) | 2.2.6 (1) |
| hFc-F107-10G1-DM1 | 0.013 +/− 0.014 (4) | 0.460 (1) |
| hFc-sdAb001-DM1 | 0.887 +/− 0.218 (6) | not convergent (1) |
| hFc-F107-7H5-DM1 | 0.014 +/− 0.026 (9) | 0.098 +/− 0.035 (2) |
| hFc-F107-8D12-DM1 | 0.011 +/− 0.006 (3) | 0.296 (1) |
| hFc-sdAb008-DM1 | 0.034 +/− 0.012 (6) | 0.240 (1) |
| mIgG-F155-3C7-DM1 | 0.327 +/− 0.098 (8) | 3.900 +/− 0.780 (2) |
| mIgG-F149-4G4-DM1 | 0.015 +/− 0.009 (8) | 0.013 +/− 0.002 (2) |
| hFc-sdAb005-DM1 | 6.664 +/− 1.718 (6) | 3.777 (1) |

Figure 11:
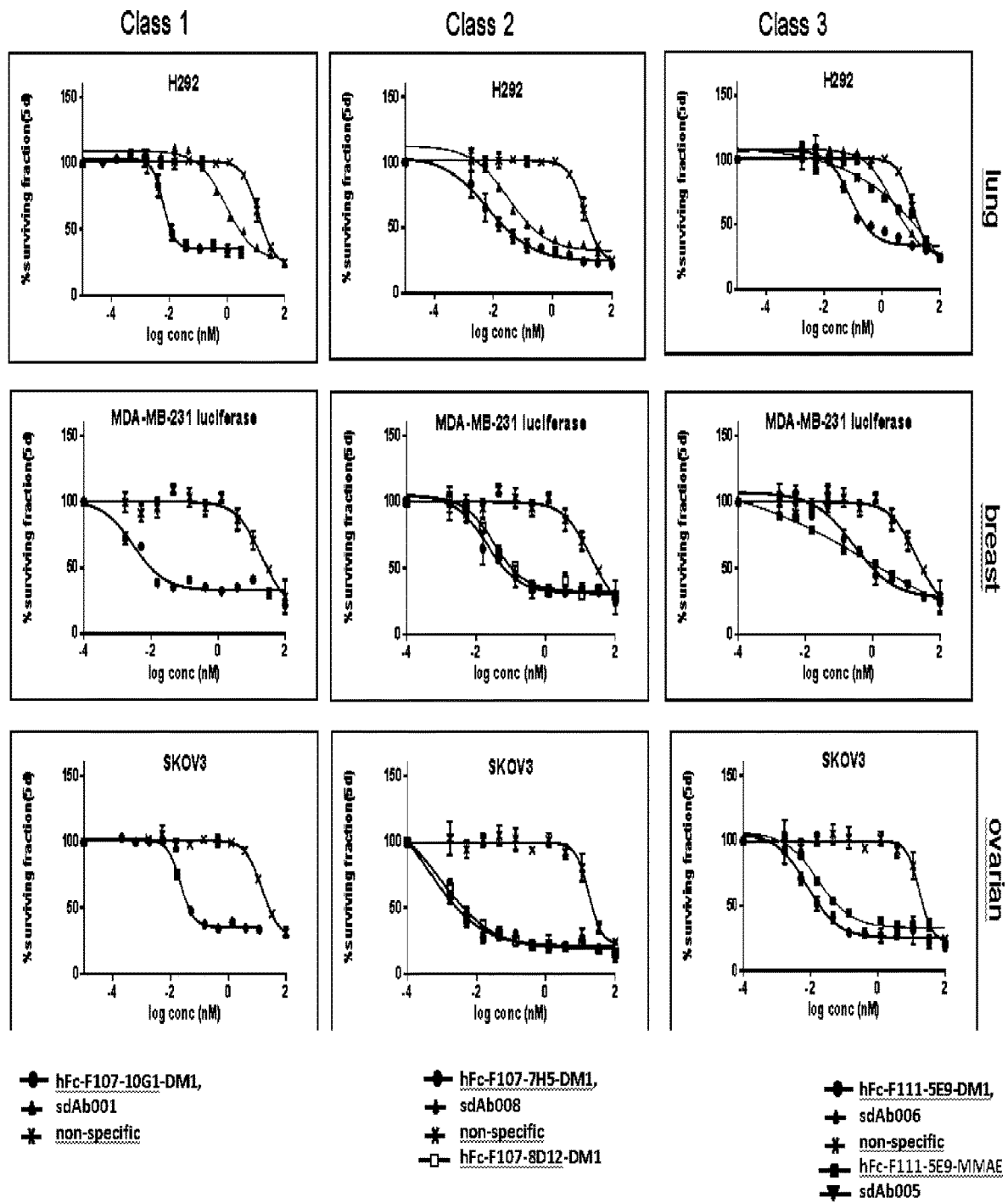
FIG. 11 shows growth inhibition binding curves of hIgG Abs and sdAbs in three tumor cell lines

Growth inhibition was assessed, and growth inhibition binding curves of hIgG Abs and sdAbs in three tumor cell lines are shown in FIG. 11. Lung, breast and ovarian cell lines (H292, MDA-MB-231 luciferase, and SKOV3, respectively) are shown. Percent surviving fraction (5d) is evaluated.

In Class 1, hIgG-F107-10G1-DM1 versus non-specific binding are shown for all cells, with sdAb001 also evaluated for H292.

In Class 2, hIgG-F107-7H5-DM1 and hIgG-F107-8D12-DM1 versus non-specific binding curves are shown for MDa-MB-231 luciferase and SKOV3 cells. sdAb008 and hIgG-F107-7H5-DM1 were evaluated versus non-specific binding for H292.

In Class 3, hIgG-F111-5E9-DM1 and hIgG-F111-5E9-MMAE versus non-specific binding are shown for all cells, with sdAb006 also evaluated for H292.

Figure 12:
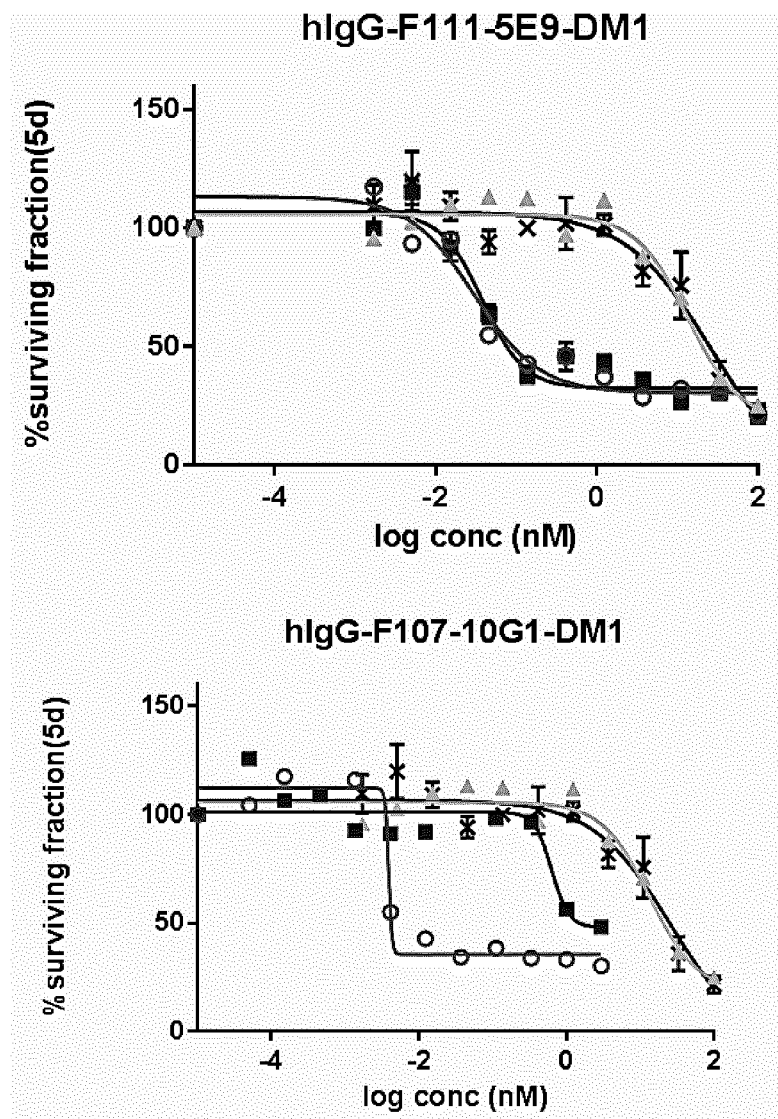
FIG. 12 shows growth inhibition binding curves of hIgG-F11-5E9-DM1 and hIgG-F107-10G1-DM1 in the presence and absence of Gas6 in H292 cell line.

FIG. 12 illustrates growth inhibition binding curves of hIgG-F11-5E9-DM1 and hIgG-F107-10G1-DM1 in the presence and absence of Gas6 in H292 cell line, as compared with non-specific binding.

Example 15: Assessment of Activity of Biparatopic/Monovalent Anti-AXL Antibodies In this example, biparatopic/monovalent anti-AXL antibodies were prepared and assessed for potency and efficacy.

Biparatopic antibodies targeting two non-overlapping epitopes can induce target clustering, which in turn promotes robust internalization, lysosomal trafficking, of receptor targets, including HER2 (Li et al. 2016). This example evaluates the ADC potency of biparatopic (2 epitopes on same target) combinations of single domain anti-AXL antibodies. Human Fc containing biparatopic antibodies were constructed according to the method published by Strop et al. (2012) in which complementary point mutations (RRR, EEE) are engineered in human IgG1 Fc regions to facilitate half monomer exchange and stabilize the bispecific antibody. The two antibodies of interest can be expressed and purified separately, and mixed together under appropriate redox conditions, resulting in a formation of a stable bispecific antibody. In all cases, the activity of biparatopic ADCs was compared to the potency of homobivalent monoparatopic sdAb-based ADCs from which they were derived.

Table 17 shows the potency ($IC_{50}$) and efficacy (% maximum inhibition) of anti AXL biparatopic construct ADCs compared to monoparatopic (bivalent) parental ADCs in SKOV3 cell line. Where available, results are expressed as: average+/−stdev (N).

sdAb008-DM1 (squares), and biparatopic 008/006 (hollow circles) are compared. Panel C provides the chart of hFc/sdAb001R/005E, sdAb005-DM1 (triangles), sdAb001-DM1 (solid circles), and the biparatopic 001/005 construct (shown as "X") are compared. Panel D provides the chart of SKOV3 combination 001R/006E, sdAb001-DM1 (solid circles), sdAb006-DM1 (diamonds) and the biparatopic 001/006 construct (large asterisks) are compared.

Example 16: In Vivo Tumor Growth Inhibition by ADCs in SKOV3 Tumor Xenograft Mouse Models In this Example, in vitro cytotoxicity is evaluated using inhibition of tumor growth inhibition in SKOV3 cells. Anti-hAXL antibody-drug conjugates ADCs were evaluated for ability to cause tumor growth inhibition in xenograft models expressing AXL.

Materials and Methods

Protocol. The protocol and procedures involving the care and use of animals in this study were reviewed and approved by Ottawa-NRC Animal Care Committee (Protocol #2014.02). Six week old, 18-20 grams female CD1 Albino mice (Crl:CD1-Foxn1nu), were ordered from Charles River Canada (St-Constant, Quebec, Canada). Animals were cared for and used in accordance with the guidelines of the Canadian Council on Animal Care (CCAC).

The anti-hAXL-ECD monoclonal antibodies were purified as outlined in Example 1 and were conjugated via lysine residues to succinimidyl trans-4-[maleimidylmethyl] cyclohexane-1-carboxylate (SMCC) linked to N2'-deacetyl-N2'-(3-mercapto-1-oxopropyl)-maytansine (DM1) as in Example 4.

Cell culture and tumor growth measurements. SKOV3 (human ovarian adenocarcinoma) cells were obtained from ATCC and cultured according to supplier's recommendations. The MDA-MB-231 triple negative (ER-/PR-/

TABLE 17

Potency ($IC_{50}$) and efficacy (% maximum inhibition) of anti-AXL biparatopic and monoparatopic (bivalent) ADCs in SKOV Cell Line

| Sample name | Antibody design | MW | DAR | IC50 (nM) | % max inh |
|---|---|---|---|---|---|
| sdAb001-DM1 | Monoparatopic | 77200 | 3.13 | 0.055 +/− 0.006 (2) | 81 +/− 0 (2) |
| sdAb005-DM1 | Monoparatopic | 77200 | 3.05 | 0.631 +/− 0.202 (2) | 78 +/− 6 (2) |
| sdAb006-DM1 | Monoparatopic | 77800 | 2.77 | 0.162 +/− 0.03 (2) | 76 +/− 6 (2) |
| sdAb008-DM1 | Monoparatopic | 78200 | 3.08 | <0.001 | ~80 |
| sdAb 001R/005E-DM1 | Biparatopic | 77200 | 3.6 | 0.008 | 89 |
| sdAb 001R/006E-DM1 | Biparatopic | 77500 | 3.39 | 0.0004 | 73 |
| sdAb 008R/005E-DM1 | Biparatopic | 77700 | 2.61 | 0.014 | 78 |
| sdAb 008R/006E-DM1 | Biparatopic | 78000 | 2.69 | 0.003 | 70 |

Preliminary results indicate that both ADCs comprising biparatopic sdAbs directed epitopes found in Domain 1A/domain 2 (sdAb 001R/005E-DM1, sdAb 001R/006E-DM1) appear much more potent (7-100×) than ADCs derived from the corresponding bivalent Fc containing sdAbs. Other biparatopic combinations tested in this example did not exhibit increased potency.

Figure 13:
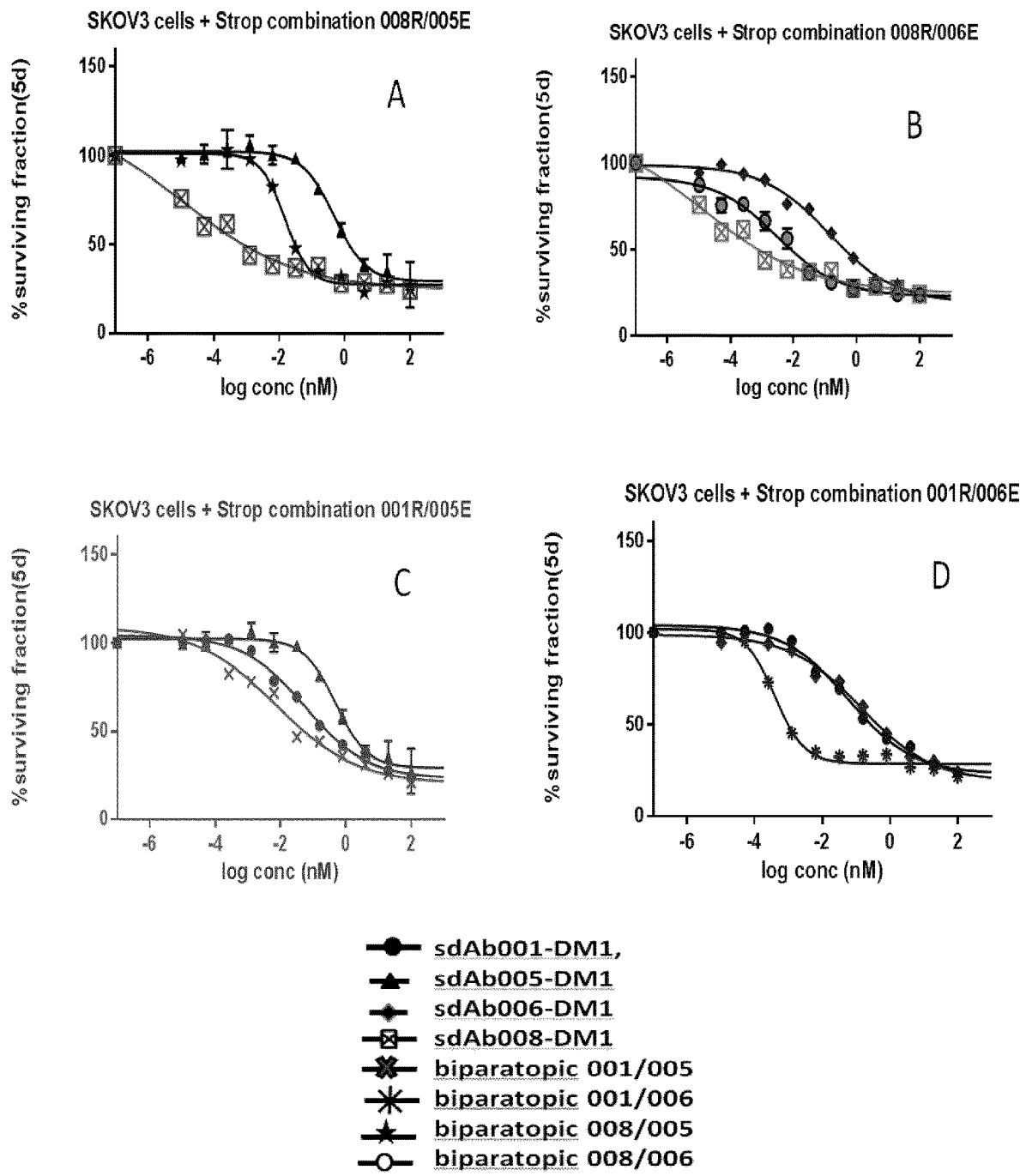
FIG. 13 shows growth inhibition binding curves of anti-AXL biparatopic construct ADCs compared to monoparatopic parental ADCs in SKOV3 cell line.

FIG. 13 shows growth inhibition binding curves of anti AXL biparatopic/monovalent constructs ADCs compared to monoparatopic/bivalent parental ADCs in SKOV3 cell line. Percent surviving fraction after 5 days is plotted as a log concentration (nM). Panel A provides the chart of SKOV3 combination 008R/005E, sdAb008-DM1 (squares), sdAb005-DM1 (triangles), and biparatopic 008/005 (stars) are compared. Panel B provides the illustrated SKOV3 combination 008R/006E chart: sdAb006-DM1 (diamonds), HER2low) breast cancer (TNBC) was purchased from ATCC (Cedarlane Labs). Stable transfectants with the firefly luciferase gene were generated by Perkin Elmer. This cell line was cultured in RPMI-1640+5% FBS.

Cells were passaged twice a week and used within 4-6 weeks for all cell lines. Cells were subcutaneously inoculated (5×10$^6$ cells in a volume of 0.1 mL PBS per injection site) in the left flank of isoflurane anesthetized nude mice (n=8) under sterile condition. Tumors were allowed to grow to a size between 80 and 100 mm$^3$ in volume, after which animals were randomized one day prior to the dosing day to ensure that each cohort contains animals with variable tumor sizes. The appropriate volume of test/control articles for each animal was prepared on the day of dosing and injected intravenously (i.v.). Mice were injected with the test articles at 5 mg/kg on day 0 and 4 (96 h interval) via tail vein. A control group was treated with saline.

Tumor growth was monitored every three days by caliper measurement for 29 days post treatment or until they were euthanized for ethical reasons (humane endpoints).

Tumor volumes were calculated according to Formula IV:

Estimated tumor volume [mm³]=π/6(length [mm]× (width [mm]×(height [mm]))  (Formula IV)

Tumor volumes in each group are shown as mean±SEM and plotted as a function of measurement time after SKOV3 cell inoculation. Group comparisons for the tumor volume data were conducted using two-way ANOVA with Tukey's multiple comparisons test using GraphPad Prism version 7.0. Differences between treatment and control groups were statistically significant at P<0.05.

Results

Compared to vehicle (PBS control) treated animals, AXL ADCs administered at 5 mg/kg (mpk) were shown to cause significant tumor growth inhibition in SKOV3 tumor xenograft mouse models (n=2). A high reproducibility in tumor growth was observed in both control and treated groups in two separate studies (referenced herein as "Study 15A" and "Study 15b"). The data from these two separate studies are represented in FIG. 14 and FIG. 15.

Figure 14:
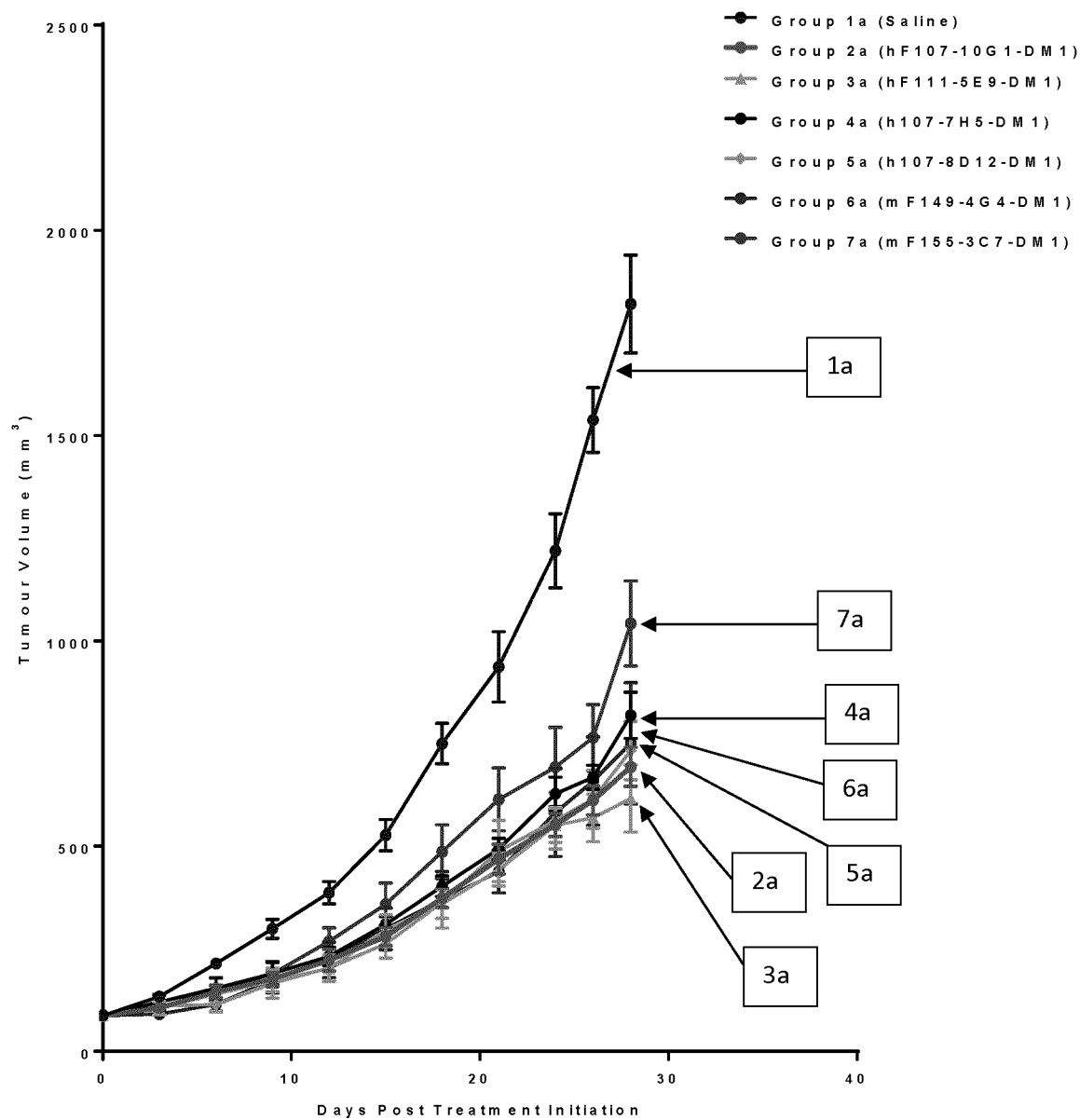
FIG. 14 shows tumor growth inhibition in SKOV3 tumor-bearing mice by selected test antibodies.

FIG. 14 shows tumor growth inhibition in Study 15a for SKOV3 tumor-bearing mice treated twice (day 0 and 4) with selected ADCs at 5 mg/kg. The ADCs used were: hF107-10G1-DM1 (2a), hF111-5E9-DM1 (3a); hF107-7H5-DM1 (4a); hF107-8D12-DM1 (5a); mF149-4G4-DM1 (6a); and mF155-3C7-DM1 (7a), for comparison with saline (1a) Tumor volumes (mm³) were recorded every three days. Each data point represents mean±SEM, (n=8).

Figure 15:
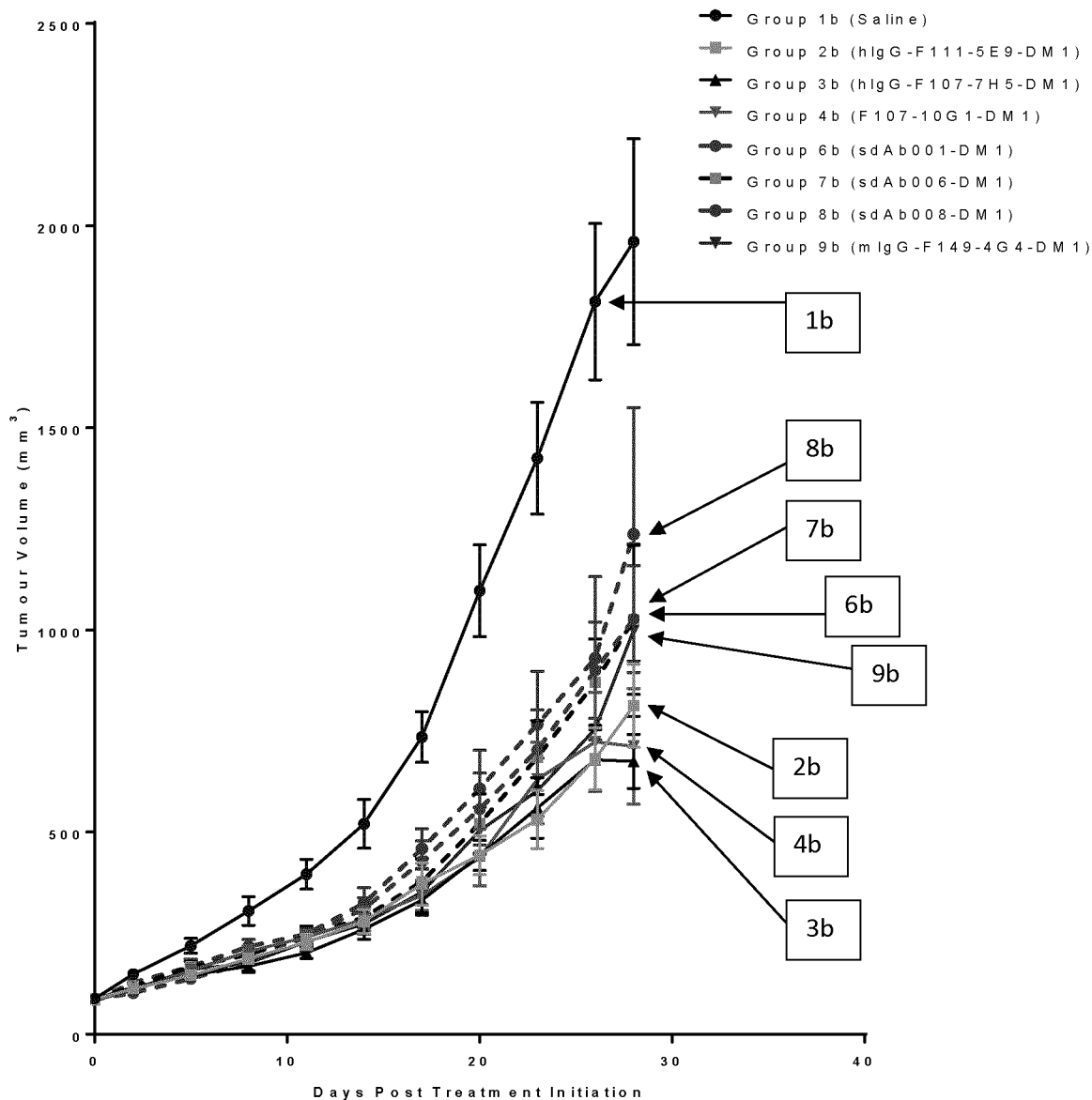
FIG. 15 shows tumor growth inhibition in SKOV3 tumor-bearing mice by selected test antibodies.

FIG. 15 shows tumor growth inhibition in Study 15b for SKOV3 tumor-bearing mice treated twice (day 0 and 4) with selected ADCs at 5 mg/kg. The ADCs used were: hF111-5E9-DM1 (2b); hF107-7H5-DM1 (3b); hF107-10G1-DM1 (4b); sdAb001-DM1 (6b); sdAb006-DM1 (7b); sdAb008-DM1 (8b); and mF149-4G4-DM1 (9b) for comparison with saline control (1b). Tumor volumes (mm³) were recorded every three days. Each data point represents mean±SEM, (n=8).

A statistically significant (p<0.05) effect on tumor growth between ADC-treated and saline-treated groups was observed from days 13-18 to day 28 with a tumor volume reduction of from 37.0% to 66.9% at day 28.

Table 18 shows the percentage of tumor volume reduction compared to the control groups (saline) at day 28 post-treatment initiation, for the data of Study 15a and 15b (see FIG. 14 and FIG. 15, respectively). Percentage of tumor volume (TV) reduction compared to control was calculated as:

% reduction=(TV$_{control}$-TV$_{treated}$)/TV$_{control}$*100  (Formula V).

TABLE 18

Percentage of Tumor Volume Reduction by ADCs in SKOV3 Xenograft Mouse Model

| Study Number | Test ADC | % of tumor volume reduction compared to control |
|---|---|---|
| Study 15A FIG. 14 | hF107-10G1-DM1 | 57.9 ± 2.9 |
| | hF111-5E9-DM1 | 62.5 ± 5.0 |
| | hF107-7H5-DM1 | 48.9 ± 3.2 |
| | hF107-8D12-DM1 | 55.4 ± 4.4 |
| | mF149-4G4-DM1 | 54.4 ± 9.0 |
| | mF155-3C7-DM1 | 38.4 ± 10.7 |

TABLE 18-continued

Percentage of Tumor Volume Reduction by ADCs in SKOV3 Xenograft Mouse Model

| Study Number | Test ADC | % of tumor volume reduction compared to control |
|---|---|---|
| Study 15B FIG. 15 | hF111-5E9-DM1 | 61.0 ± 5.1 |
| | hF107-7H5-DM1 | 66.9 ± 3.1 |
| | hF107-10G1-DM1 | 63.7 ± 7.3 |
| | sdAb001-DM1 | 47.6 ± 6.8 |
| | sdAb006-DM1 | 47.7 ± 9.48 |
| | sdAb008-DM1 | 37.0 ± 16.0 |
| | mF149-4G4-DM1 | 54.2 ± 10.3 |

Example 17: Evaluation of Efficacy of Anti-AXL ADC Hits in MDA-MB-231-Luc Xenograft Mice Following Repeated Intravenous Administrations AXL is expressed in various types of cancer and associated with invasiveness, metastasis as well as angiogenesis. Anti-AXL ADCs generated have anti-AXL antibody conjugated to microtubule inhibitor, mertansine (DM1) via SMCC linker. These ADCs show promising in vitro efficacy in various cell lines and have been selected based on potency and Gas6 sensitivity. In this Example several Anti-AXL ADC hits are screened and the role of Gas6 sensitivity on in vivo efficacy of anti-AXL ADCs is evaluated.

Efficacy and pharmacokinetics are evaluated for several Anti-AXL ADCs following two intravenous bolus administration to female NU/NU nude mice. This Example further investigates the role of Gas6 sensitivity on efficacy of Anti-AXL ADCs.

Methods

Cell Line. MDA-MB-231 is a triple negative (ER⁻, PR⁻, HER2⁻) human mammary gland adenocarcinoma cell line, which are epithelial adherent cells originally derived from a 51 years Caucasian female patient. These cells are tumorigenic in nude mice forming moderately well differentiated adenocarcinoma consistent with primary ovarian tumors. MDA-MB-231 cells are tumorigenic cells that express epidermal growth factor (EGF) and transforming growth factor alpha (TGF α). These cells form poorly differentiated adenocarcinoma (grade III) in ALS treated BALB/c mice and form poorly differentiated adenocarcinoma (grade III) in nude mice. The cell line was originally obtained from the American Tissue Culture Collection (ATCC, Manassas, Va., USA).

Cells were grown in ATCC-formulated RPMI 1640 medium (ATCC catalog #: 30-2001) with 10% fetal bovine serum (FBS, Hyclone SH30070.03) to a maximum of 80% confluence. Cells were maintained in a humidified 5% $CO_2$ atmosphere at 37° C. They were harvested by trypsinization (0.25% trypsin/EDTA, Gibco/BRL 15090-046) followed by washing in cold phosphate-buffered saline solution (PBS) and assessed for viability by capacity to exclude trypan blue dye. All cell populations for growth as xenografts in mice were, at a minimum, 98% viable.

Animal Management: Receipt, Acclimation, Housing and Handling. The protocol and procedures involving the care and use of animals in this study were reviewed and approved by Ottawa-NRC Animal Care Committee (Protocol #2014.02). The care and use of animals were in accordance with the guidelines of the Canadian Council on Animal Care (CCAC). Six week old, 18-20 grams female CD1 Albino mice (Crl:CD1-Foxn1nu), were ordered from Charles River Canada (18 LaSalle, St-Constant, Quebec, Canada). Upon arrival, the mice were subjected to a general physical examination by the staff members to ensure normal health status. No obvious abnormalities were detected in the animals received. The mice were acclimated for a period of at least 5 days to allow them to become accustomed to the housing environment. Mice were housed 4 per cage in polycarbonate cages on corn cob bedding, equipped with a filter top to avoid contamination. Each cage was clearly labelled with a color-coded cage card indicating protocol number, principal investigator's name, animal number and gender. Each mouse was uniquely identified using ear punching.

The mice were housed in a positively-pressured Tecniplast Green Line Individually Ventilated Cages (IVC) set for 75 air changes per hour under the following conditions: Temperature: 23-24° C.; Humidity: 50%; Light cycle: 12 hours light and 12 hours dark.

Aseptic techniques were used at all times when handling the mice. All equipment used in this study was sterilized with 70% ethanol prior to using. Animals were handled under the Biological Safety Cabinet (BSC) which was also disinfected with 70% ethanol each time before use. All individuals handling the mice worn a steam sterilized gown, mask, hair bonnet and sterile gloves. The autoclaved IVC cages filled with ⅛" irradiated corncob bedding (Envigo, Madison, Wis.) and a small volume of Enviro-dri paper (Shepherds Specialty Papers) were changed at least once weekly in a BSC.

Diet. All animals had free access to food and water. Water bottles were filled with ultra-filtered water and placed with caps separately in old mouse shoebox cages and steam autoclaved. Once autoclaved the caps were installed while working in the confines of the BSC. The water bottles were changed once a week or more frequently when the water levels were low. Animals were fed ad libitum, gamma-irradiated maintenance rodent diet (2914 Teklad Global 14% Protein Maintenance Diet, Envigo) during the acclimation and experimental periods.

Subcutaneous xenograft tumor model. Cells were subcutaneously inoculated ($5 \times 10^6$ cells in a volume of 0.1 mL PBS per injection site) in the left flank of isoflurane anesthetized nude mice (n=8) under sterile condition. Tumors were allowed to grow to a size between 80 and 100 mm³ in volume, after which animals were randomized one day prior to the dosing day to ensure that each cohort contains animals with variable tumor sizes.

Tumor monitoring. Tumor growth was monitored every three days by caliper measurement for 29 days post treatment or until they were euthanized for ethical reasons (humane endpoints): 1) more than 10% body weight loss without weight recovery within 48 hours; 2) tumor volume over 2500 mm³; 3) tumor ulcerations; and 4) clear signs of distress such as immobility and reduced grooming etc.

Tumor volumes were calculated according to Formula IV:

$$\text{Estimated tumor volume [mm}^3\text{]} = \pi/6(\text{length [mm]}) \times (\text{width [mm]} \times \text{height [mm]})) \quad \text{(Formula IV)}$$

Test Articles and Vehicle. All test articles were shipped on ice from NRC Montreal to Ottawa and stored at 4° C. before administration. The ADC, hF111-5E9-DM1 was prepared as batch number: CC31 May 2016; Drug to Antibody Ratio (DAR): 2.62; Concentration: 1.31 mg/mL; Aliquot Volume: 3.7 mL; Storage Conditions: 4° C.; Endotoxin Levels: <0.15; prepared at the NRC facility HHT Montreal, in Montreal, Quebec, Canada.

The vehicle for treatment was an ADC buffer with the following characteristics: Sterility: Sterile-filtered; Storage Conditions: 20-25° C.; Supplier: NRC-HHT Montreal.

Dose Formulation Preparation. Each formulation was prepared on the day of dosing. To obtain a dose level of 5 mg/kg, the injection volume of test/control article was calculated based on their stock concentrations and body weight of the animals. Preparation of the final dosing solutions was done under a clean HEPA/UV lamp biological hood by adding saline to obtain the desired volumes. The test/control articles were kept at 4° C. during the preparation period. The appropriate volume of test/control articles for each animal was injected intravenously.

Clinical Observations and Body Weight. All animals were observed once daily for mortality and signs of ill health. Individual body weight and tumor size of animals was measured and recorded on the day of treatment and every three days afterwards.

Treatment. Mice were injected with the test articles at 5 mg/kg on day 0 and 4 (96 h interval) via tail vein. A control group was treated with saline. The animal weight on the day of injection and the injected volume were recorded.

Sample Collection, Processing and Storage. Blood samples were collected via the mandibular vein at 1, 2, 4, 6, 24, 48, 96, 120, 168, 216, 264 and 336 hours post second dose from three animals per time-point.

Figure 16:
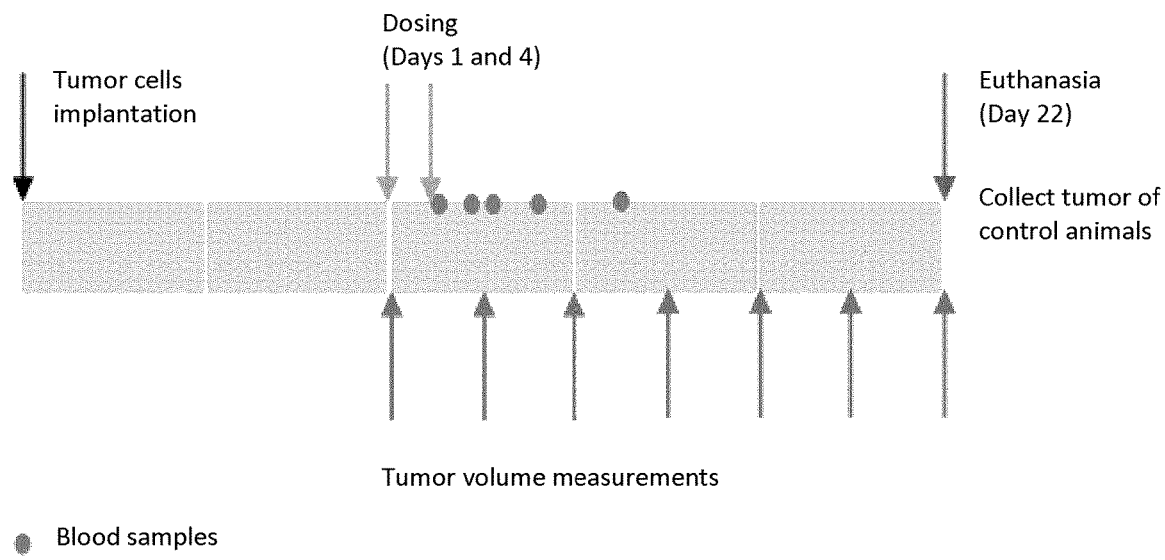
FIG. 16 shows the study design and time points for tumor growth measurements in MDA-MB-231-Luc tumor-bearing mice in Example 17.

FIG. 16 shows the study design, including where blood samples were taken at: pre-$2^{nd}$ dose, 1 h, 2 h, 4 h, 6 h, 24 h, 48 h, 96 h, 120 h, 168 h, 216 h, 264 h, and 336 h. Tumor volume measurements were taken, and dosing was at days 1 and 4, while tumor volume measurements were taken at intervals indicated. Also shown in FIG. 16, below the study design, are the animal numbers and time points for the study. Approximately 80-100 µL of the obtained blood was allowed to clot at room temperature for 15-30 minutes and then centrifuged at 1500 g for 10 minutes at room temperature. Following centrifugation, the liquid component (serum) was immediately, transferred into the pre-labelled tubes, snap-frozen immediately on dry ice and stored at −80° C.

At the end of the study, tumors were collected. Half portion of each tumor was fixed in 4% paraformaldehyde at room temperature overnight, washed with PBS and paraffin embedded. Subsequently, the paraffin embedded tumors will be processed for AXL expression as per discretion of project lead. The other half of the tumor was rapidly frozen using dry ice and stored in −80° C. for further analysis.

Statistical Analysis. Tumor volumes in each group are shown as mean±SEM and plotted as a function of measurement time after MDA-MB-231-Luc cell inoculation. Group comparisons for the tumor volume data were conducted using two-way ANOVA with Tukey's multiple comparisons test using GraphPad™ Prism version 7.0. Differences between treatment and control groups were statistically significant at P<0.05. Grubbs' test was used to determine outliers within the control/treatment groups ($\alpha$=0.05).

Results & Discussion

Figure 17:
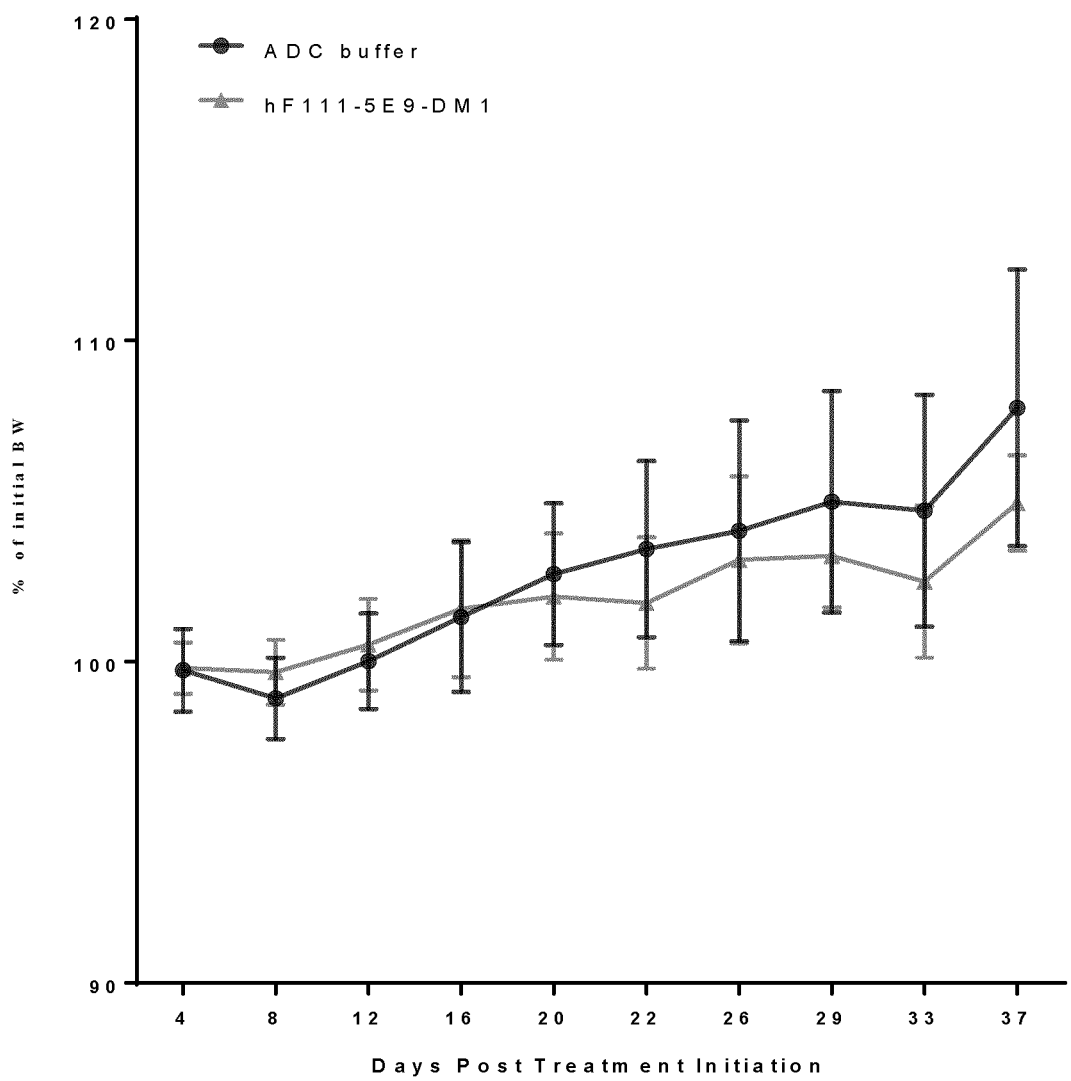
FIG. 17 shows the effect of hF111-5E9-DM1 on body weight up to 37 days post-treatment initiation in Example 17.

FIG. 17 shows the effect of anti-AXL ADCs on body weight, as a percentage of initial body weight (BW) in MDA-MB-231-Luc tumor-bearing mice after being treated twice (day 0 and 4) with hF111-5E9-DM1 at 5 mg/kg. The ADC buffer (circles) and hF111-5E9-DM1 (triangles) groups are illustrated.

Body weight was measured as an indicator of off-target potential toxicity. No significant difference was observed between the control animals (ADC buffer group) and hF111-5E9-DM1 treated animals. The mice in both groups gained about 10% body weight during the experimental period.

Figure 18:
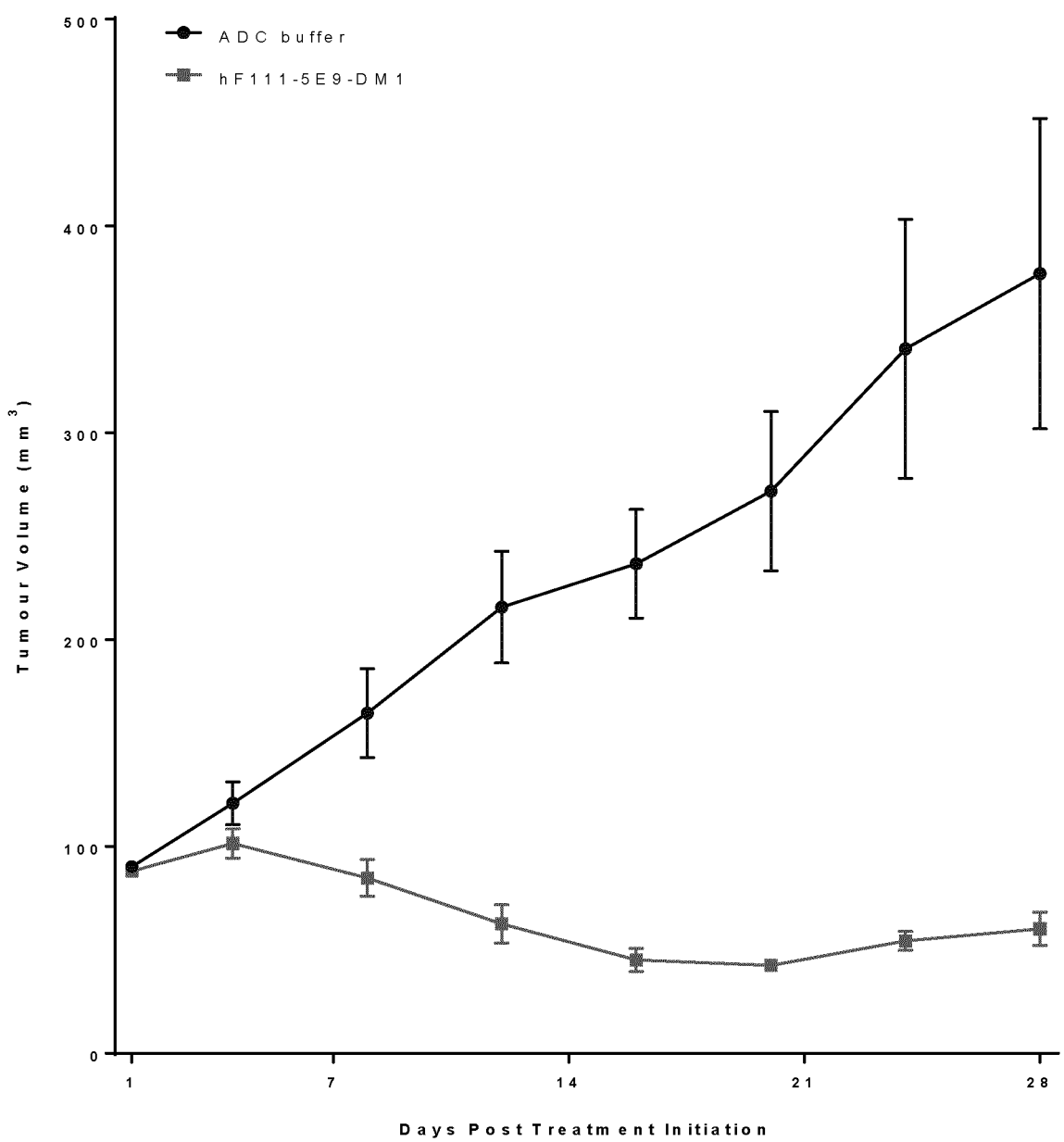
FIG. 18 shows the effect of hF111-5E9-DM1 on tumor growth up to 28 days post-treatment initiation in Example 17.

FIG. 18 shows the effect of anti-AXL ADCs on tumor growth, assessed as tumor volume. Tumor growth curves in MDA-MB-231-Luc tumor-bearing mice treated twice (day 0 and 4) with either ADC buffer (CTR) or 5 mg/kg hF111-5E9-DM1 are shown, with tumor volumes (mm³) being recorded every three days. Each data point represents mean±SEM, for ADC buffer (circles) and hF111-5E9-DM1 (triangles) groups.

A statistically significant ($p<0.05$) effect on tumor growth was observed between hF111-5E9-DM1-treated and ADC buffer-treated groups from days 8 to day 28. One animal from the hF111-5E9-DM1 group showed significantly higher tumor growth rate compared to the rest in the same group. This animal was further identified as an outlier using the Grubbs' test ($\alpha=0.05$).

The average tumor volume reduction in the hF111-5E9-DM1-treated group was from about 90 to 60 mm3, compared to the control group, which experienced tumor growth from about 90 to 360 mm3 at day 28. This striking difference in reduced tumor volume shows that anti-AXL ADCx can reduce tumor volume in a breast cancer tumor model.

Example 18: Evaluation of Anti-AXL sdAbs Ability to Cross the Blood Brain Barrier In Vitro The ability of anti-AXL antibodies to cross the blood brain barrier is evaluated in this example. Due to the expression of AXL in the central nervous system (CNS), antibodies targeting AXL and linked to a toxin (such as DM1, MMAE, etc) could exhibit very potent on-target toxicity in the brain if they are able to cross the blood brain barrier (BBB). Thus, the capacity of certain anti-AXL sdAbs to cross the BBB is evaluated using a human in vitro BBB model.

Material and Methods

Human Blood Brain Barrier Model. A stem cell based human BBB model is used. The model utilizes brain endothelial cells (BECs) generated from human amniotic fluid-derived induced pluripotent stem cells. This in vitro human blood-brain barrier (BBB) model enables pre-clinical screening of prospective BBB-permeant compounds and CNS-targeting antibodies. These BECs exhibit substantial barrier properties such as well-organized continuous tight junctions, high transendothelial electrical resistance (TEER) and polarized expression of efflux and receptor-mediated transcytosis (RMT) transporters.

Transwell-based in vitro BBB model. The Transwell BBB assay is composed of BECs seeded onto gelatin-coated permeable Transwell membrane inserts that are placed into 12-well companion plates. BEC were seeded at 500,000 cells/membrane on rat-tail collagen coated 0.83 cm² Falcon™ cell inserts, 1 μm pore size in 1 mL of BEC feeding medium without phenol red. The wells of a 12-well tissue culture plate (i.e., bottom chamber for transport) contained 2 mL of BEC medium without phenol red. The TEER values were measured for each insert and only inserts with a TEER of >300 Ωcm² were used for transcytosis studies. Transport experiments were performed in the transport buffer (10 mM HEPES, 5 mM $MgCl_2$, and 0.01% BSA in phosphate buffered saline, pH 7.4; 1 mL upper chamber and 2 mL bottom chamber) in "multiplexed" fashion by adding a mixture of test antibody (Table 19) and negative control (A20.1) at 1.25 μM of each to the top chamber and by collecting 100 μL aliquot from the bottom chamber at 15, 30, 60 and 90 min (followed by the replacement of 100 μL of transport buffer into the bottom chamber after each aliquot collection) for simultaneous quantification of all test antibodies by nanoLC-MS/MS (multiple reaction monitoring—MRM).

Specific peptide signatures for the test articles and for A20.1 were determined for MRM analysis. For test antibodies, Fc peptide (TTPPVLDSDGSFFLYSK; SEQ ID NO:187) and for negative control A20.1 peptide (EFVAAGSSTGR; SEQ ID NO:188) were detected by MRM. The integrity of the BBB during the period of the assay was monitored by incorporation of a BBB non-crossing sdAb (A20.1) in each test sample. FC5Hfc1X0 was used as a positive control and TWIN200-hIgG1 as a negative control. The sdAbs and control test articles evaluated in this study are outlined in Table 19. The experiment was performed in triplicates.

TABLE 19

Test Articles (Anti-AXL sdAbs fused to Fc domain of hIgG1) and Control Molecules used in in vitro BBB Assay*

| Code | # of inserts | Time (min) | Test Antibody | | | | Negative Control | | | |
| --- | --- | --- | --- | --- | --- | --- | --- | --- | --- | --- |
| | | | Name | Detail | MW | Top μM | Name | Details | MW | Top μM |
| AOL | 3 | 90 | FC5hFc1X0 | AP16 0408 | 78334 | 1.25 | A20.1 | 140915 | 15670 | 1.25 |
| AOM | 3 | 90 | NRC-sdAb001-hIgG1 | — | 76853 | 1.25 | A20.1 | 140915 | 15670 | 1.25 |
| AON | 2 | 90 | NRC-sdAb002-hIgG1 | — | 79514 | 1.25 | A20.1 | 140915 | 15670 | 1.25 |
| AOO | 1 | 90 | NRC-sdAb003-hIgG1 | — | 77267 | 1.25 | A20.1 | 140915 | 15670 | 1.25 |
| AOP | 2 | 90 | NRC-sdAb004-hIgG1 | — | 78810 | 1.25 | A20.1 | 140915 | 15670 | 1.25 |
| AOQ | 3 | 90 | NRC-sdAb005-hIgG1 | — | 76915 | 1.25 | A20.1 | 140915 | 15670 | 1.25 |
| AOR | 3 | 90 | NRC-sdAb006-hIgG1 | — | 77496 | 1.25 | A20.1 | 140915 | 15670 | 1.25 |
| AOS | 3 | 90 | NRC-sdAb008-hIgG1 | — | 77838 | 1.25 | A20.1 | 140915 | 15670 | 1.25 |

TABLE 19-continued

Test Articles (Anti-AXL sdAbs fused to Fc domain of hIgG1)
and Control Molecules used in in vitro BBB Assay*

| Code | # of inserts | Time (min) | Test Antibody | | | | Negative Control | | | |
| --- | --- | --- | --- | --- | --- | --- | --- | --- | --- | --- |
| | | | Name | Detail | MW | Top µM | Name | Details | MW | Top µM |
| AOT | 1 | 90 | TWIN200-hIgG1 | — | 79009 | 1.25 | A20.1 | 140915 | 15670 | 1.25 |

*For test antibodies, Fc peptide (SEQ ID NO: 187) and for negative control A20.1 peptide (SEQ ID NO: 188) were monitored (MRM).

Results

Figure 19:
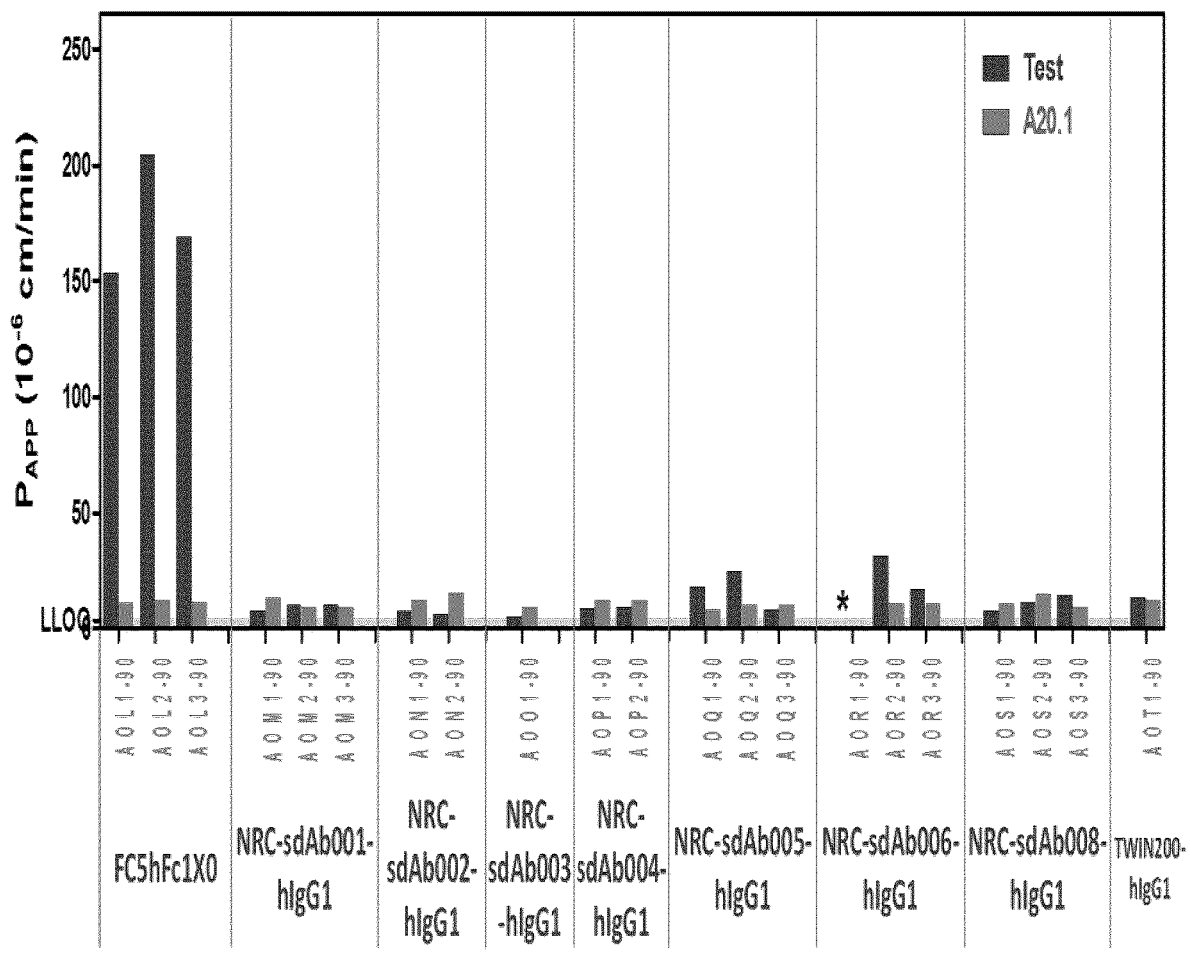
FIG. 19 shows the Papp values of FC5Hfc1X0 (positive control), TWIN200-hIgG1 (negative control) and seven anti-AXL sdAbs evaluated in Example 18.

A comparison of in vitro Papp values of FC5Hfc1X0 (positive control), TWIN200-hIgG1 (negative control) and seven anti-AXL sdAbs is shown in FIG. 19. Control molecules of various molecular weights, 15.6 kDa (A20.1), and 79.0 kDa (TWIN200-hIgG1), showed similar low Papp values, ranging between about $9.0\text{-}15.0 \times 10^{-6}$ cm/min; in contrast, Papp values for FC5Hfc1X0 were about $175 \times 10^{-6}$ cm/min (>10-fold higher than A20.1). All the anti-AXL sdAbs exhibited Papp values similar to the negative controls, indicating no significant penetrability of the in vitro BBB, except for NRC-sdAb004 and NRC-sdAb005 antibodies which show low Papp values (of about 2-fold) relative to their respective controls. The grey line at the bottom of the chart indicates Lower Level of Quantification (LLOQ). The asterisk shown in the chart for NRC-sdAb006-hIgG1 indicates leaky insert AOR1 data was removed.

Table 20 provides the Papp data, and shows the statistical analysis of the Papp values for the test articles compared to A20.1 (negative control).

TABLE 20

Papp Values and Statistical Significance

| Test Ab | Papp of Test Ab | Papp of A20.1 | p-value (Test vs. A20.1) |
| --- | --- | --- | --- |
| FC5hFc | 175.8 ± 26.3 | 11.9 ± 0.8 | p < 0.001 |
| NRC-sdAb001-hIgG1 | 9.56 ± 1.52 | 10.7 ± 2.6 | ns |

TABLE 20-continued

Papp Values and Statistical Significance

| Test Ab | Papp of Test Ab | Papp of A20.1 | p-value (Test vs. A20.1) |
| --- | --- | --- | --- |
| NRC-sdAb001-hIgG1 | 7.02 ± 1.04 | 14.1 ± 2.2 | ns |
| NRC-sdAb002-hIgG1 | 5.22 ± 0.0 | 9.15 ± 0.0 | ns |
| NRC-sdAb003-hIgG1 | 9.17 ± 0.21 | 12.5 ± 0.3 | ns |
| NRC-sdAb004-hIgG1 | 17.1 ± 8.3 | 9.75 ± 1.25 | p = 0.01 |
| NRC-sdAb005-hIgG1 | 24.3 ± 10.2 | 10.9 ± 0.2 | p = 0.01 |
| NRC-sdAb006-hIgG1 | 11.4 ± 3.3 | 11.8 ± 2.9 | ns |
| NRC-sdAb008-hIgG1 | 13.6 ± 0.0 | 12.5 ± 0.0 | ns |

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

Sequences

A consolidated list of sequences referenced here is found in Table 21.

TABLE 21

Consolidate List of Sequences

| SEQ ID NO: | Sequence | Description |
| --- | --- | --- |
| 1 | KSSQSLLNX$_1$RTRKX$_2$YLA, X$_1$ = S or T; X$_2$ = I or N | CDR L1-B consensus |
| 2 | WASTRX$_1$X$_2$, where X$_1$ = E, H or Q and X$_2$ = S or T | CDR L2-B consensus |
| 3 | GX$_1$TFX$_2$X$_3$X$_4$X$_5$X$_6$X$_7$, X$_1$ = F or Y; X$_2$ = I, S or T; X$_3$ = S, N or K; X$_4$ = F or Y; X$_5$ = G or W; X$_6$ = I or M; X$_7$ = N, S or H | CDR H1-B consensus |
| 4 | NIX$_1$PX$_2$SX$_3$SX$_4$X$_5$YNEKFKX$_6$, X$_1$ = F, N, or Y; X$_2$ = G, N, or D; X$_3$ = S or T; X$_4$ = A or T; X$_5$ = N or D; X$_6$ = S or R | CDR H2-B consensus |
| 5 | DX$_1$YGGSPDY, X$_1$ = T or Y | CDR H3-B consensus |
| 6 | WASTRX$_1$S, X$_1$ = E or Q | CDR L2-B consensus (2) |
| 7 | GYTFTSX$_1$WIN, X$_1$ = F or Y | CDR H1-B consensus (2) |
| 8 | NIX$_1$PX$_2$SSSTNYNEKFKS, X$_1$ = F or Y and X$_2$ = G or D | CDR H2-B consensus (2) |

TABLE 21-continued

Consolidate List of Sequences

| SEQ ID NO: | Sequence | Description |
|---|---|---|
| 9 | KSSQSLLNSRTRKIYLA | F107-7H5 CDR L1-B |
| 10 | WASTRQS | F107-7H5 CDR L2-B |
| 11 | KQSYNLWT | F107-7H5/F107 & 8D12 CDR L3-B |
| 12 | GYTFTSYWIN | F107-7H5 CDR H1-B |
| 13 | NIYPDSSSTNYNEKFKS | F107-7H5 CDR H2-B |
| 14 | DTYGGSPDY | F107-7H5 CDR H3-B |
| 15 | KSSQSLLNTRTRKNYLA | F107-8D12 CDR L1-B |
| 16 | WASTRES | F107-8D12 CDR L2-B |
| 17 | GYTFISFWIN | F107-8D12 CDR H1-B |
| 18 | NIFPGSSSTNYNEKFKS | F107-8D12 CDR H2-B |
| 19 | DYYGGSPDY | F107-8D12 CDR H3-B |
| 20 | RASQDINNYLN | F111-5E9 CDR L1-B |
| 21 | YISRLHS | F111-5E9 CDR L2-B |
| 22 | QQGNTLPFT | F111-5E9 CDR L3-B |
| 23 | KYGMN | F111-5E9 CDR H1-B |
| 24 | WINTYTGEPTYADDFKG | F111-5E9 CDR H2-B |
| 25 | GGYYSNPIYPMDY | F111-5E9 CDR H3-B |
| 26 | SASSSVSYMY | F111-3C8 CDR L1-B |
| 27 | RTSNLAS | F111-3C8 CDR L2-B |
| 28 | QQYHNYPPT | F111-3C8 CDR L3-B |
| 29 | GYTFTSYVVMH | F111-3C8 CDR H1-B |
| 30 | NINPNSTSADYNEKFKR | F111-3C8 CDR H2-B |
| 31 | PLMGPYVVYFDV | F111-3C8 CDR H3-B |
| 32 | KASQDVTTAVA | F107-10G1 CDR L1-B |
| 33 | WASTRHT | F107-10G1 CDR L2-B |
| 34 | QQHFTTPLT | F107-10G1 CDR L3-B |
| 35 | NYGMS | F107-10G1 CDR H1-B |
| 36 | SISGGGGRTYYLDNVKG | F107-10G1 CDR H2-B |
| 37 | GARASYFAMDY | F107-10G1 CDR H3-B |
| 38 | DIVMSQSPSSLAVSAGEKVTMSCKSSQSLLNSRTRKIYLAWYQQKPGQSPKLLIYWASTRQSGVPDRFTGSGSGTDFTLTISSVQAEDLAVYYCKQSYNLWTFGGGTKLEIK | F107-7H5 VL |
| 39 | QVQLQQPGAELVKPGASVKLSCKASGYTFTSYWINWVKQRPGQGLEWIGNIYPDSSSTNYNEKFKSKATLTVDKSSTTAYIQFSSLTSEDSAVYYCTRDTYGGSPDYWGQGTTLTVSS | F107-7H5 VH |
| 40 | DIVMSQSPSSLAVSAGERVTMSCKSSQSLLNTRTRKNYLAWYQQKPGQSPKLLIYWASTRESGVPDRFTGSGSGTDFTLTISSVQAEDLAVYYCKQSYNLWTFGGGTKLEIK | F107-8D12 VL |
| 41 | QVQLQQPGAELVKPGASVQLSCKASGYTFISFWINWVKQRPGQGLEWMGNIFPGSSSTNYNEKFKSKATLTVDKSSSTAYMQLSSLTSEDSAVYFCARDYYGGSPDYWGQGTTLTVSS | F107-8D12 VH |

TABLE 21-continued

Consolidate List of Sequences

| SEQ ID NO: | Sequence | Description |
|---|---|---|
| 42 | QIVLTQSPAIMSASPGEKVTISCSAS<u>SSVSY</u>MYWYQQKPGSSP KPWIY<u>RTS</u>NLASGVPARFSGSGSGTSYSLTISSMEAEDAATYY C<u>QQYHNYPPT</u>FGGGTKLEIK | F111-3C8 VL |
| 43 | QVQLQQPGAELGKPGTSVKLSCKAS<u>GYTFTSYWMH</u>WVKRVP GQGLEWIGN<u>INPNSTSA</u>DYNEKFKRKATLTVDKSSSTAYMQLS TLTSEDSAVYYC<u>TRPLMGPYWYFDV</u>WGTGTTVTSS | F111-3C8 VH |
| 44 | DIQMTQTTSSLSASLGDRVTISCRAS<u>QDINNYL</u>NWYQQKPDGT VKLLIY<u>YIS</u>RLHSGVPSRFSGSGSGTDYSLTISNLELEDVATYFC <u>QQGNTLPFT</u>FGSGTKLEIK | F111-5E9 VL |
| 45 | QIQLVQSGPELKKPGETVKISCKAS<u>GYTFTKYGMN</u>WVKQAPGK GLKWMGW<u>INTYTGEPT</u>YADDFKGRFAFSLETSASTAYLQINNL TTEDMVTYFC<u>AKGGYYSNPIYPMDY</u>WGQGTSVTVSS | F111-5E9 VH |
| 46 | VIVMTQSHKFMSTSVGDRVSITCKAS<u>QDVTTA</u>VAWYQQKPGQ SPKLLIY<u>WAS</u>TRHTGVPDRFTGSGSGTDYSLTISNVQTEDLAFY YC<u>QQHFTTPLT</u>FGAGTKLELK | F107-10G1 VL |
| 47 | EVNLVESGGGVVKPGASLKLSCEAS<u>GFTFSNYGMS</u>WVRQTSD KRLEWVAS<u>ISGGGGRT</u>YYLDNVKGRFIISRENAKNTLYLQMSSL KSEDTALFYC<u>ARGARASYFAMDY</u>WGQGSSVTVSS | F107-10G1 VH |
| 48 | DIVMSQSPSSLAVSAGEKVTMSCKSSQSLLNSRTRKIYLAWYQ QKPGQSPKLLIYWASTRQSGVPDRFTGSGSGTDFTLTISSVQA EDLAVYYCKQSYNLVVTFGGGTKLEIKRTVAAPSVFIFPPSDEQL KSGTASVVCLLNNFYPREAKVQWKVDNALQSGNSQESVTEQD SKDSTYSLSSTLTLSKADYEKHKVYACEVTHQGLSSPVTKSFN RGEC | Chimeric F107-7H5 light chain |
| 49 | QVQLQQPGAELVKPGASVKLSCKASGYTFTSYWINWVKQRPG QGLEWIGNIYPDSSSTNYNEKFKSKATLTVDKSSTTAYIQFSSLT SEDSAVYYCTRDTYGGSPDYWGQGTTLTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPELLGGPSVFLFPPKPKDTLMISRTPEV TCVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSRDELTKNQVSLTCLVKGFYPSDIAVEWESNGQPE NNYKTTPPVLDSDGSFFLYSKLTVDKSRWQQGNVFSCSVMHE ALHNHYTQKSLSLSPG | Chimeric F107-7H5 heavy chain |
| 50 | DIVMSQSPSSLAVSAGERVTMSCKSSQSLLNTRTRKNYLAWYQ QKPGQSPKLLIYWASTRESGVPDRFTGSGSGTDFTLTISSVQA EDLAVYYCKQSYNLWTFGGGTKLEIKRTVAAPSVFIFPPSDEQL KSGTASVVCLLNNFYPREAKVQWKVDNALQSGNSQESVTEQD SKDSTYSLSSTLTLSKADYEKHKVYACEVTHQGLSSPVTKSFN RGEC | Chimeric F107-8D12 light chain |
| 51 | QVQLQQPGAELVKPGASVQLSCKASGYTFISFWINWVKQRPG QGLEWMGNIFPGSSSTNYNEKFKSKATLTVDKSSSTAYMQLSS LTSEDSAVYFCARDYYGGSPDYWGQGTTLTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVDK KVEPKSCDKTHTCPPCPAPELLGGPSVFLFPPKPKDTLMISRTP EVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVM HEALHNHYTQKSLSLSPG | Chimeric F107-8D12 heavy chain |
| 52 | QIVLTQSPAIMSASPGEKVTISCSASSSVSYMYWYQQKPGSSP KPWIYRTSNLASGVPARFSGSGSGTSYSLTISSMEAEDAATYY CQQYHNYPPTFGGGTKLEIKRTVAAPSVFIFPPSDEQLKSGTAS VVCLLNNFYPREAKVQWKVDNALQSGNSQESVTEQDSKDSTY SLSSTLTLSKADYEKHKVYACEVTHQGLSSPVTKSFNRGEC | Chimeric F111-3C8 light chain |
| 53 | QVQLQQPGAELGKPGTSVKLSCKASGYTFTSYWMHWVKRVP GQGLEWIGNINPNSTSADYNEKFKRKATLTVDKSSSTAYMQLS TLTSEDSAVYYCTRPLMGPYWYFDVWGTGTTVTVSSASTKGP SVFPLAPSSKSTSGGTAALGCLVKDYFPEPVTVSWNSGALTSG VHTFPAVLQSSGLYSLSSVVTVPSSSLGTQTYICNVNHKPSNTK VDKKVEPKSCDKTHTCPPCPAPELLGGPSVFLFPPKPKDTLMIS | Chimeric F111-3C8 heavy chain |

TABLE 21-continued

Consolidate List of Sequences

| SEQ ID NO: | Sequence | Description |
|---|---|---|
|  | RTPEVTCVVVDVSHEDPEVKFNWYVDGVEVHNAKTKPREEQY NSTYRVVSVLTVLHQDWLNGKEYKCKVSNKALPAPIEKTISKAK GQPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPG |  |
| 54 | DIQMTQTTSSLSASLGDRVTISCRASQDINNYLNWYQQKPDGT VKLLIYYISRLHSGVPSRFSGSGSGTDYSLTISNLELEDVATYFC QQGNTLPFTFGSGTKLEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC | Chimeric F111-5E9 light chain |
| 55 | QIQLVQSGPELKKPGETVKISCKASGYTFTKYGMNWVKQAPGK GLKWMGWINTYTGEPTYADDFKGRFAFSLETSASTAYLQINNL TTEDMVTYFCAKGGYYSNPIYPMDYWGQGTSVTVSSASTKGP SVFPLAPSSKSTSGGTAALGCLVKDYFPEPVTVSWNSGALTSG VHTFPAVLQSSGLYSLSSVVTVPSSSLGTQTYICNVNHKPSNTK VDKKVEPKSCDKTHTCPPCPAPELLGGPSVFLFPPKPKDTLMIS RTPEVTCVVVDVSHEDPEVKFNWYVDGVEVHNAKTKPREEQY NSTYRVVSVLTVLHQDWLNGKEYKCKVSNKALPAPIEKTISKAK GQPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPG | Chimeric F111-5E9 heavy chain |
| 56 | VIVMTQSHKFMSTSVGDRVSITCKASQDVTTAVAWYQQKPGQ SPKLLIYWASTRHTGVPDRFTGSGSGTDYSLTISNVQTEDLAFY YCQQHFTTPLTFGAGTKLELKRTVAAPSVFIFPPSDEQLKSGTA SVVCLLNNFYPREAKVQWKVDNALQSGNSQESVTEQDSKDST YSLSSTLTLSKADYEKHKVYACEVTHQGLSSPVTKSFNRGEC | Chimeric F107-10G1 light chain |
| 57 | EVNLVESGGGVVKPGASLKLSCEASGFTFSNYGMSWVRQTSD KRLEWVASISGGGGRTYYLDNVKGRFIISRENAKNTLYLQMSSL KSEDTALFYCARGARASYFAMDYWGQGSSVTVSSASTKGPSV FPLAPSSKSTSGGTAALGCLVKDYFPEPVTVSWNSGALTSGVH TFPAVLQSSGLYSLSSVVTVPSSSLGTQTYICNVNHKPSNTKVD KKVEPKSCDKTHTCPPCPAPELLGGPSVFLFPPKPKDTLMISRT PEVTCVVVDVSHEDPEVKFNWYVDGVEVHNAKTKPREEQYNS TYRVVSVLTVLHQDWLNGKEYKCKVSNKALPAPIEKTISKAKGQ PREPQVYTLPPSRDELTKNQVSLTCLVKGFYPSDIAVEWESNG QPENNYKTTPPVLDSDGSFFLYSKLTVDKSRWQQGNVFSCSV MHEALHNHYTQKSLSLSPG | Chimeric F107-10G1 heavy chain |
| 58 | MAWRCPRMGRVPLAWCLALCGWACMAPRGTQAEESPFVGN PGNITGARGLTGTLRCQLQVQGEPPEVHWLRDGQILELADSTQ TQVPLGEDEQDDWIVVSQLRITSLQLSDTGQYQCLVFLGHQTF VSQPGYVGLEGLPYFLEEPEDRTVAANTPFNLSCQAQGPPEPV DLLWLQDAVPLATAPGHGPQRSLHVPGLNKTSSFSCEAHNAK GVTTSRTATITVLPQQPRNLHLVSRQPTELEVAWTPGLSGIYPL THCTLQAVLSDDGMGIQAGEPDPPEEPLTSQASVPPHQLRLGS LHPHTPYHIRVACTSSQGPSSWTHWLPVETPEGVPLGPPENIS ATRNGSQAFVHWQEPRAPLQGTLLGYRLAYQGQDTPEVLMDI GLRQEVTLELQGDGSVSNLTVCVAAYTAAGDGPWSLPVPLEA WRPGQAQPVHQLVKEPSTPAFSWPWWGSGGGSSTG | rhAXL-ECD |
| 59 | MVLQTQVFISLLLWISGAYG | Light chain signal sequence |
| 60 | MDWTWRILFLVAAATGTHA | Heavy chain signal sequence |
| 61 | gacattgtgatgtcacagtctccatcctccctggctgtgtcagcaggagagaaggtcacta tgagctgcaaatccagtcagagtctgctcaacagtagaacccgaaagatctacttggtt ggtaccagcagaaaccaggtcagtctcctaaactgctgatctattgggcatccactaggc aatctggggtccctgatcgcttcacaggcagtggatctgggacagatttcactctcaccatc agcagtgtgcaggctgaagacctggcagtttattactgcaagcaatcttataatctgtggac gttcggtggaggcaccaagctggaaatcaaacgg | F107-7H5 VL sequence |
| 62 | caggtccaactgcagcagcctggggctgagcttgtgaagcctggggcttcagtgaaact gtcctgcaaggcttctggctacactttcaccagctactggataaactgggtgaagcagag gcctggacaaggccttgagtggattggaaatatttatcctgatagtagtagtactaactaca atgagaagttcaagagcaaggccacactgactgtagacaagtcctccaccacagccta catacagttcagcagcctgacatctgaggactctgcggtctattattgtacaagagatacct atggtggtagccctgactactggggccaaggcaccactctcacagtctcctca | F107-7H5 VH sequence |

TABLE 21-continued

Consolidate List of Sequences

| SEQ ID NO: | Sequence | Description |
|---|---|---|
| 63 | gacattgtgatgtcacagtctccatcctccctggctgtgtcagcaggagagagggtcacta tgagctgcaaatccagtcagagtctgctcaacactagaacccgaaagaactacttggctt ggtaccagcagaaaccagggcagtctcctaaactgctgatctactgggcatccactagg gaatctggggtccctgatcgcttcacaggcagtggatctgggacagatttcactctcaccat cagcagtgtgcaggctgaagacctggcagtttattactgcaagcaatcttataatctgtgga cgttcggtggaggcaccaagctggaaatcaaa | F107-8D12 VL sequence |
| 64 | caggtccaactgcagcagcctggggctgagcttgtgaagcctggggcttcagtgcagct gtcctgcaaggcttctggctacacctttatcagcttctggataaactgggtgaagcagagg cctggacaaggccttgagtggatgggaaatattttcctggtagtagtagtacgaactaca atgagaagttcaagagcaaggccacactgactgtagacaaatcctccagcacagcta catgcagctcagcagcctgacatctgaggactctgcggtctattttgtgcaagagattact atggtggtagccctgactactggggccaaggcaccactctcacagtytcctca | F107-8D12 VH sequence |
| 65 | gatatccagatgacacagactacatcctccctgtctgcctctctgggagacagagtcacc atcagttgcagggcaagtcaggacattaacaattattttaaactggtatcagcagaaacca gatggaactgttaaactcctgatctactacatatcaagattacactcaggagtcccatcaa ggttcagtggcagtgggtctggaacagattattctctcaccattagcaacctggagctaga agatgttgccacttactttgccaacaggtaatacgcttccattcacgttcggctcggggac aaagttggaaataaaa | F111-5E9 VL sequence |
| 66 | cagatccagttggtgcagtctggacctgagctgaagaagcctggagagacagtcaagat ctcctgcaaggcttctgggtataccttcacaaaatatggaatgaactgggtaaagcaggct ccaggaaagggttaaagtggatgggctggataaacacctacactgggagagccaacat atgctgatgacttcaagggacggtttgccttctcttggaaacctctgccagcactgcctattt gcagatcaacaacctcacaactgaggacatggtcacatatttctgtgcaaaaggggggt attatagtaaccctatctatcctatggactactggggtcaaggaacctcagtcaccgtctcct ca | F111-5E9 VH sequence |
| 67 | caaattgttctcacccagtctccagcaatcatgtctgcatctccaggggagaaggtcacca tatcctgcagtgccagctcaagtgtaagttacatgtattggtaccagcagaagccaggatc ctcccccaaaccctggatttatcgcacatccaacctggcttctggagtccctgctcgcttca gtggcagtgggtctgggacctcttactctctcacaatcagcagcatggaggctgaagatg ctgccacttattactgccagcagtatcataattacccacccacgttcggagggggaccaa agctggaaataaaacgg | F111-3C8 VL sequence |
| 68 | caggtccaactgcagcagcctggggctgaactgggcaagcctggggacatcagtgaag ctgtcctgcaaggcttctggctacaccttcaccagctattggatgcactgggtgaagcgggt gcctggacaaggccttgagtggattggaaatattaatcctaatagtactagtgctgactac aatgagaagttcaagaggaaggccacattgactgtagacaaatcctccagcacagcct acatgcagctcagcaccctgacatctgaggactctgcggtctactactgtacaagacccc taatgggtccttactggtacttcgatgtctggggcacagggaccacggtcaccgtctcctca | F111-3C8 VH sequence |
| 69 | gtcattgtgatgacccagtctcacaaattcatgtccacatcagtaggagacagggtcagta tcacctgcaaggccagtcaggatgtgactactgctgtagcctggtatcaacaaaaacca gggcaatctcctaaactactgatttactgggcatccacccggcacactggagtccctgatc gcttcacaggcagtggatctgggacagattattctctcaccatcagcaatgtgcagactga agacctggcattttattactgtcagcaacattttaccactcctctcacgttcggtgctgggacc aagttggagctgaaa | F107-10G1 VL sequence |
| 70 | gaagtgaacctggtggagtctgggggaggcgtagtgaagcctggagcgtctctgaaact ctcctgtgaagcctctggattcactttcagtaactatggcatgtcttgggttcgccagcttca gacaagaggctggagtgggtcgcatccattagtggtggtggtagaacctactatcta gacaatgtaaagggccgattcatcatctccagagagaatgccaagaacaccctgtacct gcaaatgagtagtctgaagtctgaggacacggccttgttttactgtgcaagaggagctcg ggcctcttactttgctatggactactgggtcaaggaagttcagtcaccgtctcctca | F107-10G1 VH sequence |
| 71 | MAWRCPRMGRVPLAWCLALCGWACMAPRGTQAEESPFVGN PGNITGARGLTGTLRCQLQVQGEPPEVHWLRDGQILELADSTQ TQVPLGEDEQDDWIVVSQLRITSLQLSDTGQYQCLVFLGHQTF VSQPGYVGLEGLPYFLEEPEDRTVAANTPFNLSCQAQGPPEPV DLLWLQDAVPLATAPGHGPQRSLHVPGLNKTSSFSCEAHNAK GVTTSRTATITVLPQQPRNLHLVSRQPTELEVAWTPGLSGIYPL THCTLQAVLSDDGMGIQAGEPDPPEEPLTSQASVPPHQLRLGS LHPHTPYHIRVACTSSQGPSSWTHWLPVETPEGVPLGPPENIS ATRNGSQAFVHWQEPRAPLQGTLLGYRLAYQGQDTPEVLMDI GLRQEVTLELQGDGSVSNLTVCVAAYTAAGDGPWSLPVPLEA WRPGQAQPVHQLVKEPSTPAFSWPWWGSGGGSSTGHHHHH HHHG | (rh)AXL-ECD His8 |
| 72 | MAWRCPRMGRVPLAWCLALCGWACMAPRGTQAEESPFVGN PGNITGARGLTGTLRCQLQVQGEPPEVHWLRDGQILELADSTQ TQVPLGEDEQDDWIVVSQLRITSLQLSDTGQYQCLVFLGHQTF VSQPGYVGLEGLPYFLEEPEDRTVAANTPFNLSCQAQGPPEPV | AXL-full length His6 |

TABLE 21-continued

Consolidate List of Sequences

| SEQ ID NO: | Sequence | Description |
|---|---|---|
| | DLLWLQDAVPLATAPGHGPQRSLHVPGLNKTSSFSCEAHNAK GVTTSRTATITVLPQQPRNLHLVSRQPTELEVAWTPGLSGIYPL THCTLQAVLSDDGMGIQAGEPDPPEEPLTSQASVPPHQLRLGS LHPHTPYHIRVACTSSQGPSSWTHWLPVETPEGVPLGPPENIS ATRNGSQAFVHWQEPRAPLQGTLLGYRLAYQGQDTPEVLMDI GLRQEVTLELQGDGSVSNLTVCVAAYTAAGDGPWSLPVPLEA WRPGQAQPVHQLVKEPSTPAFSWPWWYVLLGAVVAAACVLIL ALFLVHRRKKETRYGEVFEPTVERGELVVRYRVRKSYSRRTTE ATLNSLGISEELKEKLRDVMVDRHKVALGKTLGEGEFGAVMEG QLNQDDSILKVAVKTMKIAICTRSELEDFLSEAVCMKEFDHPNV MRLIGVCFQGSERESFPAPVVILPFMKHGDLHSFLLYSRLGDQP VYLPTQMLVKFMADIASGMEYLSTKRFIHRDLAARNCMLNENM SVCVADFGLSKKIYNGDYYRQGRIAKMPVKWIAIESLADRVYTS KSDVWSFGVTMWEIATRGQTPYPGVENSEIYDYLRRGNRLKQ PADCLDGLYALMSRCWELNPQDRPSFTELREDLENTLKALPPA QEPDEILYVNMDEGGGYPEPPGAAGGADPPTQPDPKDSCSCL TAAEVHPAGRYVLCPSTTPSPAQPADRGSPAAPGQEDGAYLE CGRYASHHHHH | |
| 73 | QVQLQQPGTELVKPGASVKLSCKAS<u>GYIFTNFW</u>INWVKQRPG QGLEWIG<u>NIFPGSNSS</u>NYNEKFKNKATLTVDKSSTAYMHLSSL TSEDSAVYYC<u>VRDYYGGSPDY</u>WGQGTTLTVSS | F155-3C7 VH |
| 74 | DIVMSQSPSSLAVSAGEKVTMSCKSS<u>QSLLNSKTRKNY</u>LAWYQ QKPGQSPKLLIY<u>WAS</u>TRESGVPARFTGSGSGTDFTLTISSVQA EDLAIYYC<u>KHSYNLWT</u>FGGGTKLEIR | F155-3C7 VL |
| 75 | QIQLVQSGPELKKPGETVKISCKTS<u>GYTFTYYG</u>INWVKQAPGK GLEWMGW<u>INTYLGEP</u>TYADDFKGRFAFSLETSASTAYLQINNL RDEDMATYFC<u>TRGTMSYSFDY</u>WGQGTALTVSS | F149-4G4 VH |
| 76 | QNVLTQSPAIMSASPGEEVTMTCRA<u>SSSVSSSY</u>LHWYQQKSG ASPKLWIY<u>STS</u>KLASGVPARFSGSGSGTSYSLTISSVEAEDAAT YYC<u>HQYSGDPLT</u>FGSGTKLEVK | F149-4G4 VL |
| 77 | GFTFSNYG | F107-10G1 CDR H1-A |
| 78 | ISGGGGRT | F107-10G1 CDR H2-A |
| 79 | ARGARASYFAMDY | F107-10G1 CDR H3-A |
| 80 | QDVTTA | F107-10G1 CDR L1-A |
| 81 | WAS | F107-10G1 CDR L2-A |
| 82 | QQHFTTPLT | F107-10G1 CDR L3-A |
| 83 | GYTFTKYG | F111-5E9 CDR H1-A |
| 84 | INTYTGEP | F111-5E9 CDR H2-A |
| 85 | AKGGYYSNPIYPMDY | F111-5E9 CDR H3-A |
| 86 | QDINNY | F111-5E9 CDR L1-A |
| 87 | YIS | F111-5E9 CDR L2-A |
| 88 | QQGNTLPFT | F111-5E9 CDR L3-A |
| 89 | GYTFISFW | F107-8D12 CDR H1-A |
| 90 | IFPGSSST | F107-8D12 CDR H2-A |
| 91 | ARDYYGGSPDY | F107-8D12 CDR H3-A |
| 92 | QSLLNTRTRKNY | F107-8D12 CDR L1-A |
| 93 | WAS | F107-8D12 CDR L2-A |
| 94 | KQSYNLWT | F107-8D12 CDR L3-A |
| 95 | GYTFTSYW | F107-7H5 CDR H1-A |
| 96 | IYPDSSST | F107-7H5 CDR H2-A |

TABLE 21-continued

Consolidate List of Sequences

| SEQ ID NO: | Sequence | Description |
|---|---|---|
| 97 | TRDTYGGSPDY | F107-7H5 CDR H3-A |
| 98 | QSLLNSRTRKIY | F107-7H5 CDR L1-A |
| 99 | WAS | F107-7H5 CDR L2-A |
| 100 | KQSYNLWT | F107-7H5 CDR L3-A |
| 101 | GYIFTNFW | F155-307 CDR H1-A |
| 102 | IFPGSNSS | F155-307 CDR H2-A |
| 103 | VRDYYGGSPDY | F155-307 CDR H3-A |
| 104 | QSLLNSKTRKNY | F155-307 CDR L1-A |
| 105 | WAS | F155-307 CDR L2-A |
| 106 | KHSYNLWT | F155-307 CDR L3-A |
| 107 | GYTFTSYW | F111-308 CDR H1-A |
| 108 | INPNSTSA | F111-3C8 CDR H2-A |
| 109 | TRPLMGPYVVYFDV | F111-3C8 CDR H3-A |
| 110 | SSVSY | F111-308 CDR L1-A |
| 111 | RTS | F111-3C8 CDR L2-A |
| 112 | QQYHNYPPT | F111-308 CDR L3-A |
| 113 | GYTFTYYG | F149-4G4 CDR H1-A |
| 114 | INTYLGEP | F149-4G4 CDR H2-A |
| 115 | TRGTMSYSFDY | F149-4G4 CDR H3-A |
| 116 | SSSVSSSY | F149-4G4 CDR L1-A |
| 117 | STS | F149-4G4 CDR L2-A |
| 118 | HQYSGDPLT | F149-4G4 CDR L3-A |
| 119 | QVKLEESGGGLVQAGGSLRLSCTAS_ASISSFDIM_GWYRQAPGK QRELVAA_ITTLDIAN_YRDSVKGRFTISRDNAKNTVYLQMDSLKP EDTARYHC_AAFQSDQNY_WGQGTQVTVSS | NRC-sdAb001 |
| 120 | QVQLVDSGGGLVQAGGSLRLSCATS_TRTVSSAVM_AWFRQAPE KVRDFVGF_ITNSGNI_LYDDSVKGRFTISRDNAQNTVYLQMNSLK PEDTAVYYC_AAKWSFSSGYGDLRRAAMYDY_WGQGTQVTVSS | NRC-sdAb002 |
| 121 | QVQLVESGGGLVQAGGSLRLSCAASGVTLDYTAIGWFRQAPG KERELVAAITSGGNTDYAESAKGRFRISRDNSKNTIYLQMNSLK PEDTGVYYCAARRGGARGEYDYWDQGTQVTVSS | NRC-sdAb003 |
| 122 | QVQLVESGGGVVQAGGSLRLSCAFS_RGAFDTYE_IGWFRQAPG KEREFVAA_VTRNGDSV_VYADSLKARFTASRNNAVNTAYLHMNI LQPEDTATYYC_AANWRPLRTSSGADDYAD_WGQGTQVTVSS | NRC-sdAb004 |
| 123 | QVKLEESGGGLAQAGGSLRLSCAASG_SISSINT_IGWFRQAPGK QRELVAA_SDSGANRN_YADSVKGRFTISRDNAKNTVYLQMNNLK PEDTAIYYC_RAWGTGTISTMY_WGQGTQVTVSS | NRC-sdAb005 |
| 124 | QVKLEESGGGLVQAGASLRLSCVAS_ESIFGFNTM_GWYRQAPG NERELVAS_ISNSKRTM_YADSVKGRFTISRDNAKNTVNLQMNNL KPEDTAVYYC_RAWGIITSATVY_WGQGTQVTVSS | NRC-sdAb006 |
| 125 | QVKLEESGGGLVQAGGSLRLSCATS_TRTVSSAVM_AWFRQAPE KERDFVGF_ISNSGSV_YYDDSVKGRFTISRDNAQNTVYLQMNSL KPEDTAVYYC_AIIWRTSDLTGRFNT_WGQGTQVTVSS | NRC-sdAb007 |

TABLE 21-continued

Consolidate List of Sequences

| SEQ ID NO: | Sequence | Description |
|---|---|---|
| 126 | QVKLEESGGGLVQAGGSLRLSCAAS<u>GSSGMINT</u>MGWYRQAP GKQRELVAR<u>RSTGGTT</u>NYADSVKGRFTISRDDANNTVYLQMN SLKPEDTAVYYC<u>AIIWRTSDLTGRFNT</u>WGQGTQVTVSS | NRC-sdAb008 |
| 127 | ASISSFDI | NRC-sdAb001 CDR1-A |
| 128 | ITTLDIA | NRC-sdAb001 CDR2-A |
| 129 | AAFQSDQNY | NRC-sdAb001 CDR3-A |
| 130 | TRTVSSAV | NRC-sdAb002 CDR1-A |
| 131 | ITNSGNI | NRC-sdAb002 CDR2-A |
| 132 | AAKWSFSSGYGDLRRAAMYDY | NRC-sdAb002 CDR3-A |
| 133 | GVTLDYTA | NRC-sdAb003 CDR1-A |
| 134 | ITSGGNT | NRC-sdAb003 CDR2-A |
| 135 | AARRGGARGEYDY | NRC-sdAb003 CDR3-A |
| 136 | RGAFDTYE | NRC-sdAb004 CDR1-A |
| 137 | VTRNGDSV | NRC-sdAb004 CDR2-A |
| 138 | AANWRPLRTSSGADDYAD | NRC-sdAb004 CDR3-A |
| 139 | GSISSINT | NRC-sdAb005 CDR1-A |
| 140 | SDSGANR | NRC-sdAb005 CDR2-A |
| 141 | RAWGTGTISTMY | NRC-sdAb005 CDR3-A |
| 142 | ESIFGFNT | NRC-sdAb006 CDR1-A |
| 143 | ISNSKRT | NRC-sdAb006 CDR2-A |
| 144 | RAWGIITSATVY | NRC-sdAb006 CDR3-A |
| 145 | TRTVSSAV | NRC-sdAb007 CDR1-A |
| 146 | ISNSGSV | NRC-sdAb007 CDR2-A |
| 147 | AIIWRTSDLTGRFNT | NRC-sdAb007 CDR3-A |
| 148 | GSSGMINT | NRC-sdAb008 CDR1-A |
| 149 | RSTGGTT | NRC-sdAb008 CDR2-A |
| 150 | AIIWRTSDLTGRFNT | NRC-sdAb008 CDR3-A |
| 151 | NFWIN | F155-3C7 CDR H1-B |
| 152 | NIFPGSNSSNYNEKFKN | F155-307 CDR H2-B |
| 153 | DYYGGSPDY | F155-307 CDR H3-B |
| 154 | KSSQSLLNSKTRKNYLA | F155-307 CDR L1-B |
| 155 | WASTRES | F155-307 CDR L2-B |
| 156 | KHSYNLWT | F155-307 CDR L3-B |
| 157 | YYGIN | F149-4G4 CDR H1-B |
| 158 | WINTYLGEPTYADDFKG | F149-4G4 CDR H2-B |
| 159 | GTMSYSFDY | F149-4G4 CDR H3-B |
| 160 | RASSSVSSSYLH | F149-4G4 CDR L1-B |
| 161 | STSKLAS | F149-4G4 CDR L2-B |

TABLE 21-continued

Consolidate List of Sequences

| SEQ ID NO: | Sequence | Description |
|---|---|---|
| 162 | HQYSGDPLT | F149-4G4 CDR L3-B |
| 163 | FDIMG | NRC-sdAb001 CDR1-B |
| 164 | AITTLDIANYRDSVKG | NRC-sdAb001 CDR2-B |
| 165 | FQSDQNY | NRC-sdAb001 CDR3-B |
| 166 | SAVMA | NRC-sdAb002 CDR1-B |
| 167 | FITNSGNILYDDSVKG | NRC-sdAb002 CDR2-B |
| 168 | KWSFSSGYGDLRRAAMYDY | NRC-sdAb002 CDR3-B |
| 169 | YTAIG | NRC-sdAb003 CDR1-B |
| 170 | AITSGGNTDYAESAKG | NRC-sdAb003 CDR2-B |
| 171 | RRGGARGEYDY | NRC-sdAb003 CDR3-B |
| 172 | TYEIG | NRC-sdAb004 CDR1-B |
| 173 | AVTRNGDSVVYADSLKA | NRC-sdAb004 CDR2-B |
| 174 | NWRPLRTSSGADDYAD | NRC-sdAb004 CDR3-B |
| 175 | ASDSGANRNYADSVKG | NRC-sdAb005 CDR1-B |
| 176 | ASDSGANRNYADSVKG | NRC-sdAb005 CDR2-B |
| 177 | WGTGTISTMY | NRC-sdAb005 CDR3-B |
| 178 | FNTMG | NRC-sdAb006 CDR1-B |
| 179 | SISNSKRTMYADSVKG | NRC-sdAb006 CDR2-B |
| 180 | WGIITSATVY | NRC-sdAb006 CDR3-B |
| 181 | SAVMA | NRC-sdAb007 CDR1-B |
| 182 | FISNSGSVYYDDSVKG | NRC-sdAb007 CDR2-B |
| 183 | IWRTSDLTGRFNT | NRC-sdAb007 CDR3-B |
| 184 | INTMG | NRC-sdAb008 CDR1-B |
| 185 | RRSTGGTTNYADSVKG | NRC-sdAb008 CDR2-B |
| 186 | IWRTSDLTGRFNT | NRC-sdAb008 CDR3-B |
| 187 | TTPPVLDSDGSFFLYSK | Fc peptide |
| 188 | EFVAAGSSTGR | A20.1 peptide |

Note-
CDR sequences descriptions followed by "-A" indicates IMGT CDR convention.
CDR sequences descriptions followed by "-B" indicates Kabat CDR convention.

REFERENCES

All publications referred to herein are hereby incorporated by reference.

International Patent Publication WO2016/005593 A1 (Breij et al.)

U.S. Patent Application Publication US 2014/0227283 A1 (Robert et al.)

Asiedu M K, Beauchamp-Perez F D, Ingle J N, Behrens M D, Radisky D C, Knutson K L. (2014) AXL induces epithelial-to-mesenchymal transition and regulates the function of breast cancer stem cells. Oncogene. 33(10): 1316-24.

Baral et al. (2013) Single-domain antibodies and their utility. Curr Protoc Immunol. 2013 Nov. 18; 103:Unit 2.17.

Feneyrolles c, Spenlinhauer A, Guiet L, Fauvel B, Daydé-Cazals B, Warnault P, Chevé G, Ysri A. (2014) AXL Kinase as a Key Target for Oncology: Focus on Small Molecule Inhibitors. Mol. Cancer Ther. 13; 2141-2148.

Gjerdrum C, Tiron C, Høsiby T, Stefansson I, Haugen H, Sandal T, Collett K, Li S, McCormack E, Gjertsen B T, Micklem D R, Akslen L A, Glackin C, Lorens J B (2010) AXL is an essential epithelial-to-mesenchymal transition-induced regulator of breast cancer metastasis and patient survival. Proc Natl Acad Sci USA. 107(3):1124-9.

Gonzales N R, DePascalis R, Schlom J, Kashmiri S V S (2005) Minimizing the Immunogenicity of Antibodies for Clinical Application. Tumor Biol 26, 31-43.

Henry et al., 2016, "Isolation of TGF-β-neutralizing single-domain antibodies of predetermined epitope specificity using next-generation DNA sequencing", Protein Engineering, Design and Selection, pp. 1-5, 2016-09-08 (PEDS)

Holland S J, Powell M J, Franci C, Chan E W, Friera A M, Atchison R E, McLaughlin J, Swift S E, Pali E S, Yam G, Wong S, Lasaga J, Shen M R, Yu S, Xu W, Hitoshi Y, Bogenberger J, Nor J E, Payan D G, Lorens J B. (2005) Multiple roles for the receptor tyrosine kinase AXL in tumor formation. Cancer Res. 65(20):9294-303.

Holland S J, Pan A, Franci C, Hu Y, Chang B, Li W, Duan M, Torneros A, Yu J, Heckrodt T J, Zhang J, Ding P, Apatira A, Chua J, Brandt R, Pine P, Goff D, Singh R, Payan D G, Hitoshi Y. R428, a selective small molecule inhibitor of AXL kinase blocks tumor spread and prolongs survival in models of metastatic breast cancer. Cancer Res. 2010 Feb. 15; 70(4):1544-54.

Jones P T, Dear P H, Foote J, Neuberger M S, Winter G (1986) Replacing the complementarity-determining regions in a human antibody with those from a mouse. Nature 321, 522-525.

Kitagawa D, Yokota K, Gouda M, Narumi Y, Ohmoto H, Nishiwaki E, Akita K, Kirii Y. (2013) Activity-based kinase profiling of approved tyrosine kinase inhibitors. Genes Cells. 18(2):110-22.

Leconet et al., (2014) Preclinical validation of AXL receptor as a target for antibody-based pancreatic cancer immunotherapy. Oncogene 33, 5405-5414 (20 Nov. 2014).

Lee H J, Jeng Y M, Chen Y L, Chung L, Yuan R H. (2014) Gas6/AXL pathway promotes tumor invasion through the transcriptional activation of Slug in hepatocellular carcinoma. Carcinogenesis. 35:769-775.

Li Y, Ye X, Tan C, Hongo J A, Zha J, Liu J, Kallop D, Ludlam M J, Pei L. (2009) AXL as a potential therapeutic target in cancer: role of AXL in tumor growth, metastasis and angiogenesis. Oncogene. 28:3442-3455.

Li J Y, Perry S R, Muniz-Medina V, Wang X, Wetzel L K, Rebelatto M C, Hinrichs M J, Bezabeh B Z, Fleming R L, Dimasi N, Feng H, Toader D, Yuan A Q, Xu L, Lin J, Gao C, Wu H, Dixit R, Osbourn J K, Coats S R. A Biparatopic HER2-Targeting Antibody-Drug Conjugate Induces Tumor Regression in Primary Models Refractory to or Ineligible for HER2-Targeted Therapy. Cancer Cell. 2016 Jan. 11; 29(1):117-29.

Linger R M, Keating A K, Earp H S, Graham D K (2008) TAM receptor tyrosine kinases: Biologic functions, signaling, and potential therapeutic targeting in human cancer. Adv Cancer Res 100:35-83.

Meyer A S, Miller M A, Gertler F B, Lauffenburger D A. (2013) The receptor AXL diversifies EGFR signaling and limits the response to EGFR-targeted inhibitors in triple-negative breast cancer cells. Sci Signal. 6(287).

O'Bryan J P, Frye R A, Cogswell P C, Neubauer A, Kitch B, Prokop C, Espinosa R, 3rd, Le Beau M M, Earp H S, Liu E T. (1991) AXL, a transforming gene isolated from primary human myeloid leukemia cells, encodes a novel receptor tyrosine kinase. Mol Cell Biol. 11:5016-5031.

Paccez J D, Vogelsang M, Parker M I, Zerbini L F. (2014) The receptor tyrosine kinase AXL in cancer: biological functions and therapeutic implications. Int J Cancer. 134 (5):1024-33.

Padlan E A (1991) A possible procedure for reducing the immunogenicity of antibody variable domains while preserving their ligand-binding properties. Mol Immunol 28, 489-498.

Queen C, Schneider W P, Selick H E, Payne P W, Landolfi N F, Duncan J F, Avdalovic N M, Levitt M, Junghans R P, Waldmann T A (1989) A humanized antibody that binds to the interleukin 2 receptor. Proc Natl Acad Sci USA 86, 10029-10033.

Raymond et al. (2015) Production of α2,6-sialylated IgG1 in CHO cells. MAbs 7(3):571-583.

Rankin E B, Fuh K C, Castellini L, Viswanathan K, Finger E C, Diep A N, LaGory E L, Kariolis M S, Chan A, Lindgren D, Axelson H, Miao Y R, Krieg A J, Giaccia A J. (2014) Direct regulation of GAS6/AXL signaling by HIF promotes renal metastasis through SRC and MET. Proc Natl Acad Sci USA. 111(37):13373-8.

Riechmann L, Clark M, Waldmann H, Winter G (1988) Reshaping human antibodies for therapy. Nature 332, 323-327.

Strop P, Ho W H, Boustany L M, Abdiche Y N, Lindquist K C, Farias S E, Rickert M, Appah C T, Pascua E, Radcliffe T, Sutton J, Chaparro-Riggers J, Chen W, Casas M G, Chin S M, Wong O K, Liu S H, Vergara G, Shelton D, Rajpal A, Pons J. Generating bispecific human IgG1 and IgG2 antibodies from any antibody pair. J Mol Biol 2012; 420(3): 204-219.

Tempest P R, Bremmer P, Lambert M, Taylor G, Furze J M, Carr F J, Harris W J (1991) Reshaping a human monoclonal antibody to inhibit human respiratory syncytial virus infection in vivo. Biotechnology 9, 266-271.

Thomson S, Petti F, Sujka-Kwok I, Mercado P, Bean J, Monaghan M, Seymour S L, Argast G M, Epstein D M, Haley J D. (2011) A systems view of epithelial-mesenchymal transition signaling states. Clin Exp Metastasis. 28(2):137-55.

Tsurushita N, Hinton, R P, Kumar S (2005) Design of humanized antibodies: From anti-Tac to Zenapax. Methods 36, 69-83.

Vincke C, et al., General strategy to humanize a camelid single-domain antibody and identification of a universal humanized nanobody scaffold. J Biol Chem. 2009 Jan. 30; 284(5):3273-84.

Yakes F M, Chen J, Tan J, Yamaguchi K, Shi Y C, Yu P W, Qian F, Chu F L, Bentzien F, Cancilla B, Orf J, You A, Laird A D, Engst S, Lee L, Lesch J, et al. (2011) Cabozantinib (XL184), a Novel MET and VEGFR2 Inhibitor, Simultaneously Suppresses Metastasis, Angiogenesis, and Tumor Growth. Molecular cancer therapeutics. 10:2298-2308.

Zhang et al., 2009, Transient expression and purification of chimeric heavy chain antibodies. Protein Expression and Purification, May; 65(1):77-82.

Zhou et al., 2010, J Mol Biol, November 19; 404(1):88-99 Internalizing cancer antibodies from phage libraries selected on tumor cells and yeast displayed tumor antigen.

What is claimed is:

1. An isolated or purified antibody that specifically binds to an epitope in an immunoglobulin-like (IgL) domain of human AXL ectodomain (ECD) wherein said antibody comprises:
   Variable light chain (VL) CDR1, CDR2, and CDR3 sequences according to SEQ ID NOs: 80, 81, and 82, respectively; and
   Variable heavy chain (VH) CDR1, CDR2, and CDR3 sequences according to SEQ ID NOs: 77, 78, and 79, respectively.

2. The antibody of claim 1, which is a monoclonal antibody, a humanized antibody, a chimeric antibody, a bispecific antibody, or an AXL-binding antibody fragment thereof.

3. The antibody of claim 2, wherein the chimeric antibody comprises framework regions from human IgG1.

4. The antibody of claim 3, wherein the chimeric antibody comprises framework regions from human kappa light chain and human IgG heavy chain.

5. The antibody of claim 2, wherein the bispecific antibody is biparatopic.

6. The antibody of claim 1, comprising:
   a VL sequence according to SEQ ID NO: 46; and
   a VH sequence according to SEQ ID NO: 47.

7. The antibody of claim 1 comprising:
   a VL sequence having at least 90% sequence identity to SEQ ID NO: 46; and
   a VH sequence having at least 90% sequence identity to SEQ ID NO: 47.

8. The antibody according to claim 7, wherein the VL sequence has at least 95% sequence identity to SEQ ID NO: 46 and the VH sequence has at least 95% sequence identity to SEQ ID NO: 47.

9. The antibody or fragment of claim 7, wherein the VL sequence has at least 98% sequence identity to SEQ ID NO: 46 and the VH sequence has at least 98% sequence identity to SEQ ID NO: 47.

10. An antibody drug conjugate (ADC) comprising the antibody of claim 1, linked to a drug.

11. The antibody drug conjugate of claim 10, wherein the drug is an anti-cancer drug.

12. A pharmaceutical composition comprising the ADC of claim 10 and a pharmaceutically acceptable excipient.

13. The antibody of claim 1, wherein the antibody comprises human IgG1 Fc.

14. A nucleic acid molecule encoding the antibody of claim 1.

15. A vector comprising the nucleic acid molecule of claim 14.

16. A host cell comprising the vector of claim 15.

17. A host cell that produces the antibody of claim 1, wherein the host cell comprises a vector comprising a nucleic acid molecule that encodes the antibody.

18. The antibody of claim 1, wherein the antibody is immobilized onto a surface.

19. A conjugate comprising the antibody of claim 1, wherein the antibody is linked to a cargo molecule selected from the group consisting of detectable agent, a drug, an enzyme, a growth factor, a cytokine, a receptor trap or an antibody thereof, a carbohydrate moiety, a DNA-based molecule, a cytotoxic agent, and a viral vector.

20. The conjugate of claim 19, wherein:
   the DNA-based molecule comprises an anti-sense oligonucleotide, microRNA, siRNA, or a plasmid; or
   the viral vector is adenoviral, lentiviral or retroviral.

21. The conjugate of claim 19, wherein the molecule is from about 1 kDa to about 500 kDa in size.

22. The conjugate of claim 19, wherein the molecule is loaded in one or more liposome or nanocarrier.

23. The conjugate of claim 22, wherein the nanocarrier comprises a nanoparticle, nanowire, nanotube, or quantum dots.

* * * * *